(12) United States Patent
Kim et al.

(10) Patent No.: US 10,125,144 B2
(45) Date of Patent: Nov. 13, 2018

(54) RHO KINASE INHIBITORS

(71) Applicant: Kadmon Corporation, LLC, New York, NY (US)

(72) Inventors: Ji-in Kim, Princeton, NJ (US); Kevin Liu, West Windsor, NJ (US); Masha Poyurovsky, New York, NY (US); Dan Lu, Montvale, NJ (US); Zhenping Zhu, Woodcliff Lake, NJ (US)

(73) Assignee: KADMON CORPORATION, LLC, New York, NY (US)

( * ) Notice: Subject to any disclaimer, the term of this patent is extended or adjusted under 35 U.S.C. 154(b) by 0 days.

(21) Appl. No.: 15/027,975

(22) PCT Filed: Oct. 7, 2014

(86) PCT No.: PCT/US2014/059572
§ 371 (c)(1),
(2) Date: Apr. 7, 2016

(87) PCT Pub. No.: WO2015/054317
PCT Pub. Date: Apr. 16, 2015

(65) Prior Publication Data
US 2016/0237095 A1  Aug. 18, 2016

Related U.S. Application Data

(60) Provisional application No. 61/887,935, filed on Oct. 7, 2013.

(51) Int. Cl.
| | |
|---|---|
| *C07D 403/14* | (2006.01) |
| *C07D 495/04* | (2006.01) |
| *C07D 401/14* | (2006.01) |
| *C07D 471/04* | (2006.01) |
| *C07D 487/04* | (2006.01) |
| *C07D 491/048* | (2006.01) |
| *C07D 491/052* | (2006.01) |
| *A61K 31/506* | (2006.01) |
| *A61K 31/519* | (2006.01) |
| *A61K 39/395* | (2006.01) |
| *C07K 16/28* | (2006.01) |

(52) U.S. Cl.
CPC .......... *C07D 495/04* (2013.01); *A61K 31/506* (2013.01); *A61K 31/519* (2013.01); *A61K 39/3955* (2013.01); *C07D 401/14* (2013.01); *C07D 403/14* (2013.01); *C07D 471/04* (2013.01); *C07D 487/04* (2013.01); *C07D 491/048* (2013.01); *C07D 491/052* (2013.01); *C07K 16/2863* (2013.01); *C07K 2317/76* (2013.01)

(58) Field of Classification Search
CPC .............. A61K 31/506; A61K 31/519; A61K 39/3955; C07D 401/14; C07D 403/14; C07D 471/04; C07D 487/04; C07D 491/048; C07D 491/052; C07D 495/04

USPC ......... 544/323, 324, 326, 328; 514/256, 275
See application file for complete search history.

(56) References Cited

U.S. PATENT DOCUMENTS

| | | | | |
|---|---|---|---|---|
| 5,750,531 | A * | 5/1998 | Lee ...................... | C07D 495/04 514/256 |
| 6,352,993 | B1 * | 3/2002 | Lee ...................... | C07D 401/04 514/272 |
| 6,638,926 | B2 * | 10/2003 | Davies ................. | C07D 231/12 514/217.05 |
| 9,890,152 | B2 | 2/2018 | Bryan | |
| 2003/0078271 | A1 | 4/2003 | Blackburn et al. | |
| 2003/0171359 | A1 * | 9/2003 | Dahmann ............ | C07D 231/12 514/217.06 |
| 2004/0092570 | A1 | 5/2004 | Blackburn | |
| 2007/0161637 | A1 | 7/2007 | Bankthavatchalam et al. | |
| 2007/0185075 | A1 * | 8/2007 | Bell ..................... | C07D 239/48 514/210.2 |
| 2009/0306038 | A1 * | 12/2009 | Carceller Gonzalez ..................... | C07D 239/50 514/210.2 |
| 2010/0035863 | A1 * | 2/2010 | Raphy ................. | C07D 401/14 514/218 |
| 2011/0092474 | A1 * | 4/2011 | Cai ...................... | A61K 31/44 514/210.2 |

(Continued)

FOREIGN PATENT DOCUMENTS

| | | |
|---|---|---|
| CN | 1826328 A | 8/2006 |
| CN | 103626741 A | 3/2014 |

(Continued)

OTHER PUBLICATIONS

Lee et al., Selective ROCK2 inhibition in focal cerebral ischemia, Annals of Clinical and Translational Neurology, 1(1), pp. 2-14, (2014).*

(Continued)

*Primary Examiner* — Deepak R Rao
(74) *Attorney, Agent, or Firm* — Fox Rothschild LLP

(57) ABSTRACT

The invention provides novel inhibitors of ROCK1 and/or ROCK2. Also provided are methods of treating diseases and disorders involving inhibiting ROCK1 and/or ROCK2. The present invention includes pharmaceutical compositions comprising the compounds of the invention and a pharmaceutically acceptable carrier and/or diluents. The present invention includes compositions comprising a substantially pure compound of the invention and a pharmaceutically acceptable salt, steroisomer, or hydrate thereof: and a pharmaceutically acceptable excipient and/or diluents.

8 Claims, 23 Drawing Sheets

Specification includes a Sequence Listing.

US 10,125,144 B2
Page 2

(56) References Cited

U.S. PATENT DOCUMENTS

| | | | | |
|---|---|---|---|---|
| 2011/0224233 | A1* | 9/2011 | Xu | C07D 239/48 514/256 |
| 2012/0015940 | A1* | 1/2012 | Iwama | C07D 471/04 514/230.5 |
| 2012/0094999 | A1 | 4/2012 | Gray et al. | |

FOREIGN PATENT DOCUMENTS

| | | |
|---|---|---|
| CN | 103664908 A | 3/2014 |
| CN | 104955824 A | 9/2015 |
| JP | H08-500841 A | 1/1996 |
| JP | H09-509188 A | 9/1997 |
| JP | 2000-513014 A | 10/2000 |
| JP | 2004-509113 A | 3/2004 |
| JP | 2004-524350 A | 8/2004 |
| JP | 2006-524636 A | 11/2006 |
| JP | 2006-528640 A | 12/2006 |
| JP | 2009-504759 A | 2/2009 |
| JP | 2009-507896 A | 2/2009 |
| JP | 2009-520019 A | 5/2009 |
| JP | 2012-521427 A | 9/2012 |
| KR | 10-2013-0100587 A | 9/2013 |
| WO | 1994/014795 A1 | 7/1994 |
| WO | 1996/05177 A1 | 2/1996 |
| WO | 1998/043968 A1 | 10/1998 |
| WO | 01/40215 A1 | 6/2001 |
| WO | 2001/047921 A1 | 7/2001 |
| WO | 2002/022601 A1 | 3/2002 |
| WO | WO 02/060392 A2 * | 8/2002 |
| WO | 2002/076976 A2 | 10/2002 |
| WO | 2003/059913 A1 | 7/2003 |
| WO | 2004/014307 A2 | 2/2004 |
| WO | 2004/014376 A1 | 2/2004 |
| WO | 2004/096810 A1 | 11/2004 |
| WO | 2005/009980 A1 | 2/2005 |
| WO | 2007/022280 A1 | 2/2007 |
| WO | 2007/031529 A1 | 3/2007 |
| WO | 2007/072163 A2 | 6/2007 |
| WO | 2008/054599 A2 | 5/2008 |
| WO | 2009/152325 A1 | 12/2009 |
| WO | 2010/019392 A1 | 2/2010 |
| WO | 2010/065721 A1 | 6/2010 |
| WO | 2010/085246 A1 | 7/2010 |
| WO | 2010/111057 A1 | 9/2010 |
| WO | 2012/048222 A1 | 4/2012 |
| WO | 2012135697 A2 | 4/2012 |
| WO | 2012/112674 A2 | 8/2012 |
| WO | WO 2012/135697 A2 * | 10/2012 |
| WO | WO 2014/081718 A1 * | 5/2014 |
| WO | 2015/157556 A1 | 10/2015 |

OTHER PUBLICATIONS

Simone, Oncology: Introduction, Cecil Textbook of Medicine, 20th Edition, vol. 1, pp. 1004-101 O, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Douglas, Jr., Introduction to Viral Diseases, Cecil Textbook of Medicine, 20th Edition, vol. 2, pp. 1739-1747, 1996.*
Bergman, H, et al., "Identification of a Potent, State-Dependent Inhibitor of Nav1.7 with Oral Efficacy in the Formalin Model Persistent Pain", Journal of Medicinal Chemistry (2011) vol. 54:13, pp. 4427-4445.
Oh, K. et al., "Cardiovascular Effects of a Novel Selective Rho Kinase Inhibitor, 2-(1H-indazole-5-yl)amino-4-methoxy-6-piperzaino Triazine (DW1865)", European Journal of Pharmacology (2013); vol. 702; pp. 218-226.

Oh, K. et al., "Discovery of Novel Scaffolds for Rho Kinase 2 Inhibitor Through TR_FRET-Based High Throughput Screening Assay"; Combinatorianl Chemistry & High Throughput Screening (2013); vol. 16; pp. 37-46.
Yang, Z. et al., "Replacement of Amide with Bioisosteres led to a new Series of Potent Adenosine A2A Receptor Antagonists"; Bioorganic & Medicinal Chemistry Letters (2014); vol. 24:1; pp. 152-155.
Meng, J. et aL, "Optimization of 6-Heterocyclic-2-(1H-pyrazol-1-yl)-N-(pyridin-2-yl)primidin-4-amine as Potent Adenosine A2A Receptor Antagonists for the Treatment of Parkinson's Disease"; ACS Chemical Neuroscience (2014); vol. 5:8; pp. 674-682.
Office Action dated Jun. 26, 2018 in counterpart Japanese Patent Application No. 2016-521259, 18 pgs.
Citation No. 27 from Office Action dated Jun. 26, 2018 in counterpart Japanese Application No. 2016-521259: RN 884269-90-3, et al, Registry, Database Registry [Online] Retrieved from STN, May 15, 2006, Searching date: May 23, 2018, 2 pgs.
Citation No. 28 from Office Action dated Jun. 26, 2018 in counterpart Japanese Application No. 2016-521259:RN 884747-66-4, et al., Registry, Database, Registry [Online] Retrieved from STN, May 18, 2006, Searching date: May 23, 2018; 1 pg.
Citation No. 29 from Office Action dated Jun. 26, 2018 in counterpart Japanese Application No. 2016-521259: RN 884906-30-3, et al., Registry, Database Registry [Online] Retrieved from STN, May 19, 2006, Searching date: May 23, 2018 , 8 pgs.
Citation No. 30 from Office Action dated Jun. 26, 2018 in counterpart Japanese Application No. 2016-521259: RN 887978-70-3, et al., Database Registry [Online] Retrieved from STN, Jun. 16, 2006, Searching date: May 23, 2018, 1 pg.
Citation No. 31 from Office Action dated Jun. 26, 2018 in counterpart Japanese Application No. 2016-521259: RN 888083-74-7, et al., Registry, Database Registry [Online] Retrieved from STN, Jun. 18, 2006, Searching date May 23, 2018, 1 pg.
Citation No. 32 from Office Action dated Jun. 26, 2018 in counterpart Japanese Application No. 2016-521259: RN 888232-54-0, et al, Registry, Database Registry [Online] Retrieved from STN, Jun. 19, 2016, Searching date: May 23, 2018, pgs.
Citation No. 33 from Office Action dated Jun. 26, 2018 in counterpart Japanese Application No. 2016-521259: RN 888857-44-1, et al., 5 Registry, Database Registry [Online] Retrieved from STN, Jun. 22, 2006, Searching date: May 23, 2018, 2 pgs.
Citation No. 34 from Office Action dated Jun. 26, 2018 in counterpart Japanese Application No. 2016-521259: RN 889260-81-5, et al., Registry, Database, Registry [Online] Retrieved from STN, Jun. 25, 2006, Searching date: May 23, 2018, 1 pg.
Citation No. 35 from Office Action dated Jun. 26, 2018 in counterpart Japanese Application No. 2016-521259: RN 956159-12-9 Registry, Database Registry [Online] Retrieved from STN, Nov. 28, 2007, Searching date: May 23, 2018, 1 pg.
Citation No. 36 from Office Action dated Jun. 26, 2018 in counterpart Japanese Application No. 2016-521259: RN 1027575-40-1 Registry, Database Registry [Online] Retrieved from STN, Jun. 12, 2008, Searching date: May 23, 2018, 1 pg.
Citation No. 37 from Office Action dated Jun. 26, 2018 in counterpart Japanese Application No. 2016-521259: RN 1111675-29-6, et al., Registry, Database Registry [Online] Retrieved from STN, Feb. 25, 2009, Searching date: May 23, 2018, 21 pgs.
Citation No. 38 from Office Action dated Jun. 26, 2018 in counterpart Japanese Application No. 2016-521259: RN 1111950-96-9, et al., Registry, Database Registry [Online] Retrieved from STN, Feb. 26, 2009, Searching date: May 23, 2018, 1 pg.
Citation No. 39 from Office Action dated Jun. 26, 2018 in counterpart Japanese Application No. 2016-521259: RN 1225147-32-9, et al., Registry, Database Registry [Online] Retrieved from STN, May 26, 2010, Searching date: May 23, 2018, 1 pg.
Citation No. 40 from Office Action dated Jun. 26, 2018 in counterpart Japanese Application No. 2016-521259: RN 1239727-17-3, et al., 1239767-34-0, 1239777-53-7 Registry, Database Registry [Online], Retrieved from STN, Sep. 1, 2010, Searching date: May 23, 2018, 2 pgs.
Citation No. 41 from Office Action dated Jun. 26, 2018 in counterpart Japanese Application No. 2016-521259: RN 1239838-21-1

(56) References Cited

OTHER PUBLICATIONS

Registry, Database Registry [Online] Retrieved from STN, Sep. 2, 2010, Searching date: May 23, 2018, 1 pg.

Citation No. 42 from Office Action dated Jun. 26, 2018 in counterpart Japanese Application No. 2016-521259: RN 1241707-74-3 Registry, Database Registry [Online] Retrieved from STN, Sep. 16, 2010, Searching date: May 23, 2018, 1 pg.

Citation No. 43 from Office Action dated Jun. 26, 2018 in counterpart Japanese Application No. 2016-521259: RN 1363824-35-4, et al., Registry, Database Registry [Online], Retrieved from STN, Mar. 30, 2012, Searching date: May 23, 2018, 1 pg.

Citation No. 44 from Office Action dated Jun. 26, 2018 in counterpart Japanese Application No. 2016-521259: RN 1505436-75-8 Registry, Database Registry [Online] Retrieved from STN, Dec. 2013, Searching date: May 23, 2018, 1 pg.

* cited by examiner

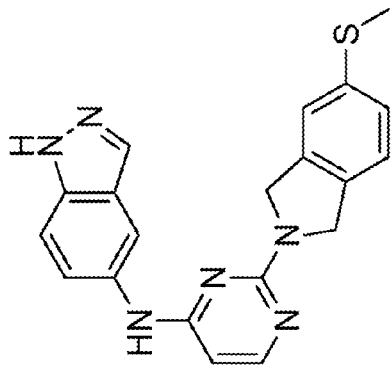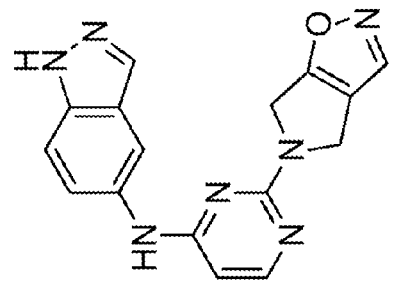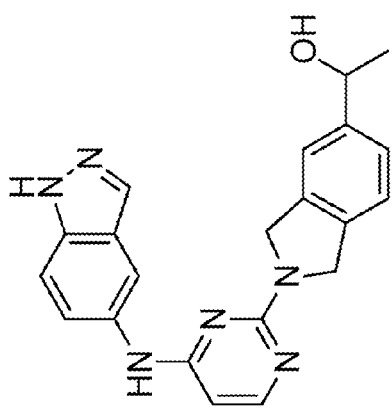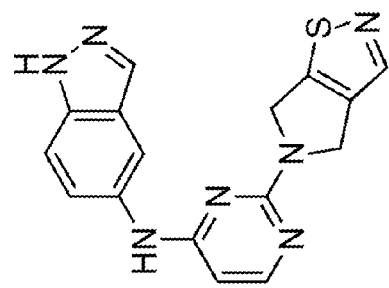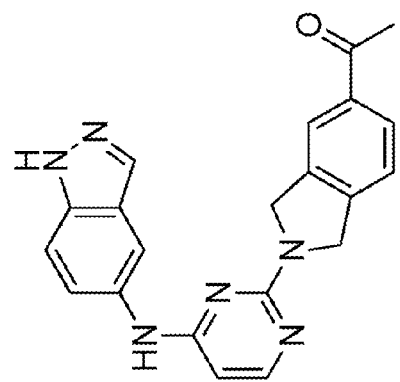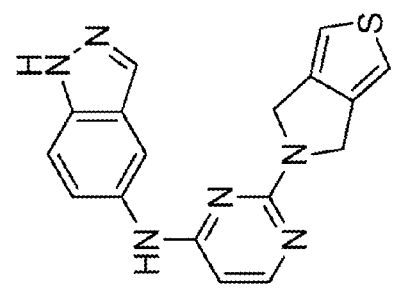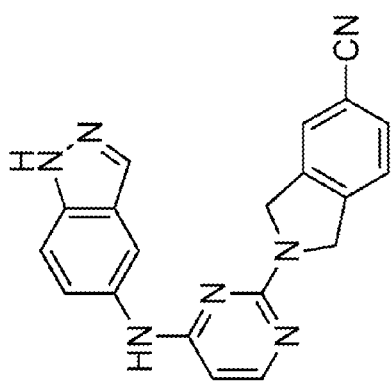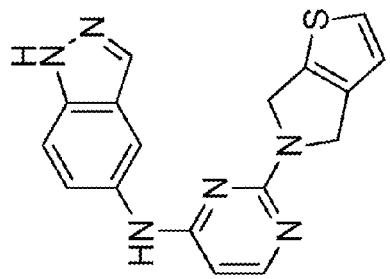
FIG.1 (continued)

B.
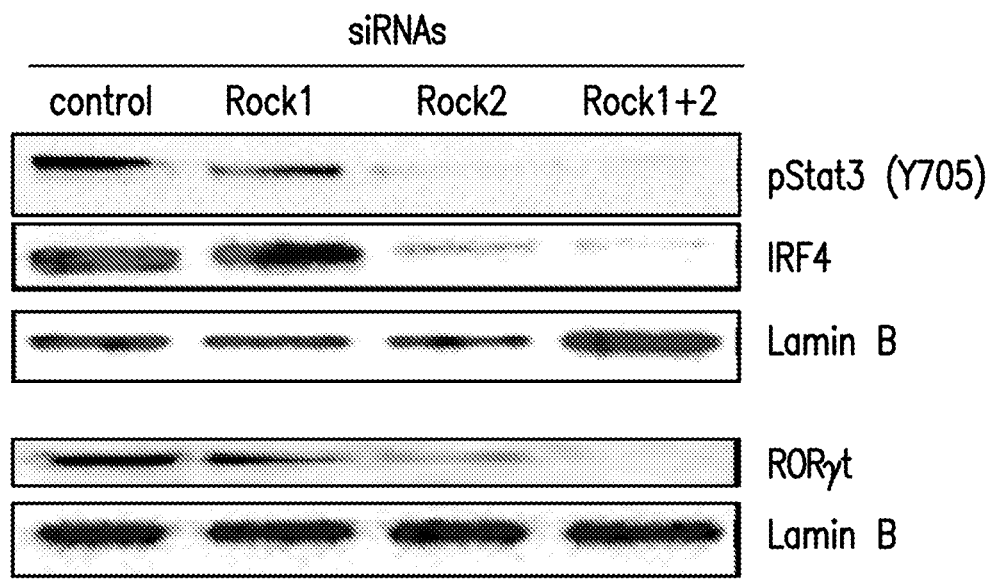
C.
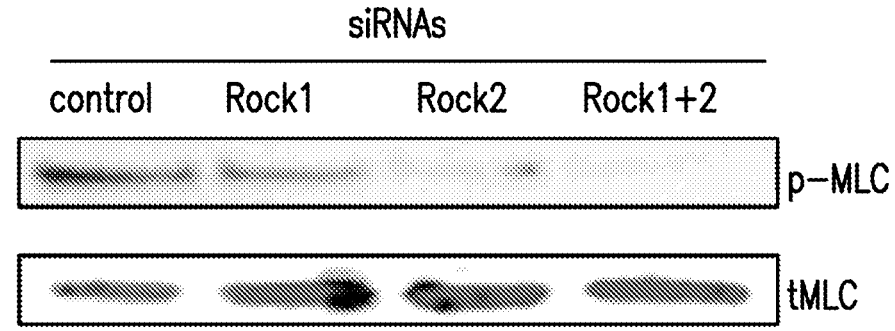
FIG. 2 (continued)

```
Kabat
No.        1234567890123456789012345 67890123456789012345AB 67890123 4
SEQ ID NO.
4          EVQLLESGGGLVQPGGSLRLSCAAS GFTFSWYVMG--          WVRQAPGK
12         EVQLLESGGGLVQPGGSLRLSCAAS GFTFSWYIML--          WVRQAPGK Kabat                                        5                                      7
No.        456789 012ABC345678901 2345 67890123456789012ABC
SEQ ID NO.
4          GLEWVS SIYP--SGGATNYADSVKG RFTISRDNSKNTLYLQMNSL
12         GLEWVS SIGS--SGGFTDYADSVKG RFTISRDNSKNTLYLQMNSL Kabat                          9                     10                         1
No.        345678901234  567890ABCDEFGHIJK12                345678901 0
                                                                     23
SEQ ID NO.
4          RAEDTAVYYCAR  GNYF-----------DY                   WGQGTLVTVSS
12         RAEDTAVYYCAR  GLAAP----------RS                   WGRGTLVTVSS
```

FIG.4A

| Kabat No. | | 1 | 2 | 3 | 4 | 5 | 6 | 7 | 8 | 9 | 10 | 1 | 2 | 3 | 4 | 5 | 6 | 7 | 8 | 9 | 20 | 1 | 2 | 3 | 24 | 5 | 6 | 7 | A | B | C | D | E | F | 8 | 9 | 30 | 1 | 2 | 3 | 4 | 35 | 6 | 7 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| SEQ ID NO. 8 | | Q | S | V | L | T | Q | D | P | A | – | V | S | V | A | L | G | Q | T | V | R | I | T | C | Q | G | D | S | L | | | | | | | | R | S | Y | Y | A | S | W | Y | Q |
| 24 | | Q | S | A | L | T | Q | P | P | S | – | V | S | V | S | P | G | Q | T | A | S | I | T | C | S | G | D | K | L | | | | | | | | G | D | E | Y | A | S | W | Y | Q |
| 28 | | Q | S | Y | E | L | T | Q | P | P | S | V | S | V | S | P | G | Q | T | A | S | I | T | C | S | G | D | N | L | | | | | | | | R | H | E | Y | S | S | W | Y | Q |
| 32 | | Q | S | V | L | T | Q | P | P | S | – | V | S | V | S | P | G | Q | T | A | S | I | T | C | S | G | E | K | L | | | | | | | | G | D | E | Y | A | S | W | Y | Q |
| 36 | | Q | S | E | L | T | Q | P | P | S | – | V | S | V | S | P | G | Q | T | A | T | I | T | C | S | G | E | K | L | | | | | | | | G | D | E | Y | A | S | W | Y | Q |
| 40 | | Q | S | A | L | T | Q | P | P | S | – | V | S | V | S | P | G | Q | T | A | T | I | T | C | T | G | D | Q | I | | | | | | | | G | D | Q | F | A | S | W | Y | Q |
| 44 | | Q | S | Y | E | L | T | Q | P | P | S | V | S | V | S | P | G | Q | T | A | I | I | T | C | S | G | D | A | L | | | | | | | | G | E | R | S | A | S | W | Y | Q |
| 48 | | Q | S | A | L | T | Q | P | P | S | – | V | S | V | A | P | G | Q | T | V | T | I | S | C | S | G | S | T | S | N | | | | | | | G | N | N | Y | A | S | I | Y | Q |
| 16 | | Q | S | V | L | T | Q | P | P | S | – | V | S | E | A | P | G | T | T | V | T | I | S | C | S | G | S | S | S | N | | | | | | | I | G | N | N | A | V | H | W | Y | Q |
| 20 | | Q | S | A | L | T | Q | P | P | S | – | V | S | G | T | P | G | Q | R | V | T | I | S | C | T | G | S | S | S | N | | | | | | | I | G | T | Y | P | V | N | W | Y | Q |
| 52 | | Q | S | A | L | T | Q | P | P | S | – | V | S | E | A | P | G | Q | T | V | T | I | S | C | T | G | S | S | S | N | | | | | | | I | G | T | N | T | L | N | W | Y | Q |
| 56 | | Q | S | Y | E | L | T | Q | P | A | S | V | S | G | S | R | G | Q | S | V | S | I | H | C | S | G | S | S | S | N | | | | | | | L | G | S | N | T | V | N | W | Y | Q |
| 60 | | Q | S | V | L | T | Q | P | D | S | – | V | S | G | G | P | G | Q | S | I | H | I | H | C | T | G | S | S | S | D | | | | | | | I | E | S | Y | D | Y | V | S | W | Y | Q |
| 64 | | Q | S | A | L | T | Q | P | A | S | – | V | S | M | S | G | P | G | Q | S | I | H | I | S | C | A | G | T | S | S | H | D | | | | | | V | G | A | Y | D | Y | V | S | W | Y | K |
| 68 | | Q | S | V | L | T | Q | P | D | S | – | V | S | G | S | P | G | Q | S | I | H | I | S | C | T | G | S | S | S | H | D | | | | | | H | G | S | Y | D | Y | V | S | W | Y | K |
| 72 | | Q | S | V | L | T | Q | P | D | S | – | V | S | G | G | P | G | Q | S | I | T | I | S | C | T | G | S | S | S | H | D | | | | | | H | G | S | Y | D | Y | V | S | W | Y | K |
| 76 | | Q | S | A | L | T | Q | P | A | S | – | V | S | G | S | P | G | Q | S | I | T | I | S | C | T | G | S | S | S | H | D | | | | | | I | G | A | Y | D | Y | V | S | W | Y | K |
| 80 | | Q | S | V | V | T | Q | P | Y | S | – | V | S | G | G | P | G | Q | S | I | T | I | S | C | T | G | S | S | S | H | D | | | | | | H | G | A | Y | D | Y | V | S | W | Y | K |
| 84 | | Q | S | V | L | T | Q | P | D | S | – | V | S | G | G | P | G | Q | S | I | T | I | S | C | T | G | S | S | S | H | D | | | | | | I | G | A | Y | D | Y | V | S | W | Y | K |
| 88 | | Q | S | A | L | T | Q | P | A | S | – | V | S | G | S | P | G | Q | S | I | T | I | S | C | T | G | S | S | S | H | D | | | | | | H | G | A | Y | D | Y | V | S | W | Y | K |
| 92 | | Q | S | V | L | T | Q | P | D | S | – | V | S | G | S | P | G | Q | S | I | T | I | S | C | T | G | S | S | S | H | D | | | | | | I | G | A | Y | D | Y | V | S | W | Y | K |
| 96 | | Q | S | E | L | T | Q | P | D | S | – | V | S | G | S | P | G | Q | S | I | T | I | S | C | T | G | S | S | S | H | D | | | | | | I | G | A | Y | D | Y | V | S | W | Y | K |

| Kabat No. | 8 9 0 | 4 1 2 3 | 4 5 | 6 7 | 8 9 | 7 0 1 2 3 4 5 | 6 7 8 9 0 | 6 1 2 3 | 4 5 6 | 7 8 9 0 1 2 3 | 4 5 6 7 8 9 0 | 7 1 2 3 4 5 6 7 8 9 0 | 8 0 |
|---|---|---|---|---|---|---|---|---|---|---|---|---|---|
| SEQ ID NO: | | | | | | | | | | | | | |
| 8 | QKPG | QSPL | VI | HY | QDTN | KRPS | GI | PE | RF | SGSNSGNT | ATLTIS | ETQA | A |
| 24 | QKPG | QSPV | LI | HY | QDDN | KRPS | GI | PE | RF | SGSNSGNT | ATLTIS | ETQA | A |
| 28 | QKPG | QSPV | LI | HY | QDDS | KRPS | GI | PE | RF | SGSNSGNT | ATLTIS | GTQA | A |
| 32 | QRPG | QSPV | LI | HY | QDDN | KRPS | GI | PE | RF | SGSNSGNT | ATLTIS | GTQA | A |
| 36 | QKPG | QSPV | PI | LY | QDDN | KRPS | GI | PD | RF | SGSNSGNT | ATLTIS | GAQA | A |
| 40 | QKPG | QSPV | VI | LY | QNDS | QRPS | GI | PE | RF | SGSDSGNT | ATLTIS | ETQA | S |
| 44 | HKPG | QSPA | PI | LY | YDDT | KRPS | GI | PE | RF | SGSHSGNT | AALTIS | GLQA | T |
| 48 | QRPG | QSPA | AP | VY | SDDQ | LLPS | GV | PD | RF | SGSSSKSGNT | ASLTIS | GTQA | A |
| 16 | QKPG | QSPK | AP | LY | ANNQ | QLPS | GV | PD | RF | SGSLSGNT | SSLAIS | GLQA | S |
| 20 | QLPG | QTPA | KP | VY | YDDT | KRPS | GV | PA | RF | SGSFSGTS | ASLTIT | ETQA | T |
| 52 | QLPG | QTPA | RK | VF | TNND | QRPS | GV | PD | RF | SGSSKSGNT | ASLTIS | GLQA | S |
| 56 | QLPG | KAPK | LK | FI | DVYN | NRPS | GV | PD | RF | SGSKSGNT | ASLTIS | GLQR | S |
| 60 | QLPG | KAPK | LL | FL | DVYN | NRPS | GV | AD | RF | SGSQSGNT | ASLTIS | GLQA | P |
| 64 | QLPG | KAPK | KL | HI | DVYN | NRPS | GV | SD | RF | SGSKSGNT | ASLTIS | GLQA | P |
| 68 | YHPG | KAPK | LL | HI | DVYY | NRPS | GV | SD | RF | SGSKSGNT | ASLTIS | GLQA | P |
| 72 | HLPG | NAPK | LL | LY | DVYN | NRPS | GV | SD | RF | SGSKSGNT | ASLTIS | GLQA | P |
| 76 | HLPG | NAPK | FI | HY | DVYN | NRPS | GV | SD | RF | SGSKSGNT | ASLTIS | GLQA | P |
| 80 | HLPG | NAPK | FI | HY | DVYN | RRPS | GV | SD | RF | SGSKSGNT | ASLTIS | GLQA | P |
| 84 | HLPG | NAPK | FI | LY | DVYN | RRPS | GV | SD | RF | SGSKSGNT | ASLTIS | GLQA | P |
| 88 | HLPG | NAPK | FI | LY | DVYN | RRPS | GV | SD | RF | SGSKSGNT | ASLTIS | GLQA | P |
| 92 | HLPG | NAPK | FI | LY | DVYN | RRPS | GV | SD | RF | SGSKSGNT | ASLTIS | GLQA | P |
| 96 | HLPG | NAPK | FI | LY | DVYN | RRPS | GV | SD | RF | SGSKSGNT | ASLTIS | GLQA | P |

FIG.4B3

| SEQ ID NO: | 1 | 2 | 3 | 4 | 5 | 6 | 7 | 8 | 89 | 90 | 91 | 92 | 93 | 94 | 95 | 95A | 95B | 95C | 95D | 95E | 95F | 96 | 97 | 98 | 99 | 100 | 101 | 102 | 103 | 104 | 105 | 106 | 106A | 107 | 108 | 109 |
|---|---|---|---|---|---|---|---|---|---|---|---|---|---|---|---|---|---|---|---|---|---|---|---|---|---|---|---|---|---|---|---|---|---|---|---|---|
| 8  | M | D | E | A | D | Y | Y | C | Q | A | W | D | S | N | T |   |   |   |   |   |   | A | V | F | G | G | G | T | K | L | T | V | L | G | Q | P |
| 24 | M | D | E | A | D | Y | Y | C | Q | A | W | D | S | S | T |   |   |   |   |   |   | V | V | F | G | G | G | T | K | L | T | V | L | G | Q | P |
| 28 | L | D | E | A | D | Y | Y | C | Q | A | W | G | S | S | T |   |   |   |   |   |   | V | V | F | G | G | G | T | K | L | T | V | L | G | R | Q | P |
| 32 | M | D | E | A | D | Y | Y | C | Q | A | W | D | S | S | T |   |   |   |   |   |   | L | L | F | G | G | G | T | K | L | T | V | L | G | Q | P |
| 36 | M | D | E | A | D | Y | Y | C | Q | A | W | D | S | S | T |   |   |   |   |   |   | L | L | F | G | G | G | T | K | L | T | V | L | G | Q | P |
| 40 | M | D | E | A | H | Y | Y | C | Q | A | W | D | F | S | S |   |   |   |   |   |   | A | L | F | G | G | G | T | K | V | T | V | L | G | S | Q | P |
| 44 | I | D | E | A | D | Y | Y | C | Q | T | W | D | T | S |   |   |   |   |   |   |   | I | L | F | G | A | G | T | K | L | T | V | L | G | Q | P |
| 48 | M | D | E | A | D | Y | Y | C | Q | T | W | D | R | N | T | P |   |   |   |   |   | Y | V | F | G | G | G | T | K | L | T | V | L | G | R | Q | P |
| 16 | E | D | E | A | D | Y | Y | C | A | S | W | D | D | N | L | N | G |   |   |   |   | P | L | F | G | G | G | T | K | L | T | V | L | G | Q | P |
| 20 | M | D | E | A | D | Y | Y | C | Q | A | W | D | D | S | T |   |   |   |   |   |   | V | V | F | G | G | G | T | K | L | T | V | L | G | S | Q | P |
| 52 | E | D | E | A | D | Y | Y | C | A | T | W | D | D | S | L | I | G |   |   |   |   | P | L | F | G | G | G | T | K | L | T | V | L | G | R | Q | P |
| 56 | E | D | E | A | D | Y | Y | C | A | A | W | D | D | N | L | N | G |   |   |   |   | W | V | F | G | G | G | T | K | L | T | V | L | G | Q | P |
| 60 | E | D | E | A | D | Y | Y | C | A | A | W | D | D | S | L | S | G |   |   |   |   | V | V | F | G | G | G | T | R | R | V | T | V | L | S | Q | P |
| 64 | D | D | E | A | D | Y | F | C | M | S | W | D | T | H | T |   |   |   |   |   |   | L | L | F | G | T | G | T | R | R | V | T | V | L | S | Q | P |
| 68 | D | D | E | A | D | Y | F | C | M | S | Y | D | T | H | T |   |   |   |   |   |   | L | L | F | G | T | G | T | R | R | V | T | V | L | S | Q | P |
| 72 | D | D | E | A | D | Y | F | C | M | S | Y | D | T | H | T |   |   |   |   |   |   | L | L | F | G | T | G | T | R | R | V | T | V | L | S | Q | P |
| 76 | D | D | E | A | D | Y | F | C | M | S | Y | D | T | H | T |   |   |   |   |   |   | L | L | F | G | T | G | T | R | R | V | T | V | L | S | Q | P |
| 80 | D | D | E | A | D | Y | F | C | M | S | Y | D | T | H | T |   |   |   |   |   |   | L | L | F | G | T | G | T | R | R | V | T | V | L | S | Q | P |
| 84 | D | D | E | A | D | Y | F | C | M | S | Y | D | T | H | T |   |   |   |   |   |   | L | L | F | G | T | G | T | R | R | V | T | V | L | S | Q | P |
| 88 | D | D | E | A | D | Y | F | C | M | S | Y | D | T | H | T |   |   |   |   |   |   | L | L | F | G | T | G | T | R | R | V | T | V | L | S | Q | P |
| 92 | D | D | E | A | D | Y | F | C | M | S | Y | D | T | H | T |   |   |   |   |   |   | L | L | F | G | T | G | T | R | R | V | T | V | L | S | Q | P |
| 96 | D | D | E | A | D | Y | F | C | M | S | Y | D | T | H | T |   |   |   |   |   |   | L | L | F | G | T | G | T | R | R | V | T | V | L | S | Q | P |

FIG.4C1

| Kabat No. | 1234567890 | 1234 | 5 | 67890ABCDEF | 0123 | 4 | 567 | 7 |
|---|---|---|---|---|---|---|---|---|
| SEQ ID NO: | | | | | | | | |
| 100 | DIQMTQSPGS | LSLS | P | GERATLSCRAS | QS    VSSSY | L | AWY | Q |
| 104 | DIQMTQSPGT | LSLS | V | LPGERATLSCRA | SERH ISSNY | M | AWY | Q |
| 108 | DIQMTQSPGT | LSLS | P | GERATLSCRAS | QS    HSSNY | L | AWF | Q |
| 112 | DIQMTQSPAT | LSLS | P | GERATLSCRAS | QS    RSSGY | L | AWY | Q |
| 116 | DIQMTQSPGT | LSLS | P | GERATLSCRAS | QS    VSSNY | L | AWY | Q |
| 120 | DIQMTQSPGT | LSLS | P | GERATLSCRAS | QS    VSSSY | L | AWY | Q |
| 124 | DIQMTQSPGT | LSLS | P | GERATLSCRAS | QS    VSSNY | L | AWY | Q |
| 128 | DIQMTQSPGT | LSLS | P | GERATLSCRAS | QN    VSSWY | L | AWY | Q |
| 132 | DIQMTQSPGT | LSLS | P | GERATLSCRAS | QS    VGSSY | L | AWY | Q |
| 136 | DIQMTQSPGT | LSLS | P | GERATLSCRAS | QS    VSSSY | L | AWY | Q |
| 140 | DIQMTQSPGT | LSLS | P | GERATLSCRAS | QS    VSSSY | L | AWY | Q |
| 144 | DIQMTQSPGT | LSLS | P | GERATLSCRAS | QS    VSSNY | F | GWY | Q |
| 148 | DIQMTQSPGT | LSLS | P | GDRATLSCRAS | QS    VSSSY | L | AWY | Q |
| 152 | DIQMTQSPGT | LSLS | P | GERAATLSCRA | SQS   VSSNY | L | AWY | Q |
| 156 | DIQMTQSPGT | LSLS | P | GERATLSCRAS | QS    LNNNY | L | AWY | Q |
| 160 | DIQMTQSPGT | LSLS | P | GERATLSCRAS | QH    VSSDY | L | AWY | Q |
| 164 | DIQMTQSPAT | LSLS | V | SPGERATLSCRA | SHS   VSSDY | L | AWY | Q |
| 168 | DIQMTQSPAT | LSLS | P | GERATLSCRAS | HS    VSSDY | L | AWY | Q |
| 172 | DIQMTQSPDT | LSLS | L | SPGERATLSCRA | SHS   VSSDY | L | AWY | Q |

FIG. 4C2

| SEQ ID NO | 80-89 | 90-99 | CDR (100-106) | 107-... |
|---|---|---|---|---|
| 100 | QKPGQAPRLL | MYGASSRAT | (boxed) | GTGIPDRFSGSGSGTDFSLTISRLEP |
| 104 | QKPGQAPRLL | MYGASSIRST | GHPDRFSGESGTDFTLTISRLEP | |
| 108 | QRPGQAPRLL | IYGASSRAT | GTPDRFSGSGSGTDFTLTISRLEP | |
| 112 | QKPGQAPRLL | LYGASSRAT | GTPDARFSGSGSGTDFTLTISRLEP | |
| 116 | QKPGQAPRLL | LYGASSTRAT | GHPDRFSGSGSGTDFTLTISRLEP | |
| 120 | QKPGQAPRLL | LYGASSRAT | GIPDRFSGSGSGTDFTLTISRLEP | |
| 124 | QKPGQAPRLL | LYGASSRAT | GIPDRFSGSGSGTDFTLTISRLEP | |
| 128 | QKPGQAPRLL | MYGASNRAT | GFPDRFSGSGSGTDFTLTISRLEP | |
| 132 | QKPGQAPRLL | MYGASSRAT | GIPDRFSGSGSGTDFTLTISRLEP | |
| 136 | QKPGQAPRLL | IYGASARAT | GHPDRFSGSGSGTDFTLTISRLEP | |
| 140 | QKPGQAPRLL | LYGASSRAT | GFPDRFSGSGSGTDFTLTISRVEP | |
| 144 | QKPGQAPRLL | LYGASSRAT | GHPDRFSGSGSGTDFYLTISRLSQ | |
| 148 | QKPGQAPRLL | MYGASSRAT | GIPDARFSGSGSGTDFTLTISRLEP | |
| 152 | QKPGQAPRLL | MYGASSTRAT | GHPDRFSGSGSGTDEFTLTVSRLEQ | |
| 156 | QKPGQAPRLL | IYGASSRAT | GIPDRFSGSGSGTDFTLTISRLEP | |
| 160 | QKPGQAPRLL | IYGASSTRAT | GHPDRFSGSGSGTDFTLTISRLEP | |
| 164 | QKPGQAPRLL | LYGASARAT | GFPDRFSGSGSGTDFTLTINRLEP | |
| 168 | QKPGRAPRLV | MYGASSRAT | GIPDRFSGSGSGTDFSLTISRLEP | |
| 172 | QKPGRAPRLL | IYGASSTRAT | GHPDRFTGSGSGTDFTLTISRLEP | |
| 176 | QKPGRAPRLL | MYGASSRAT | GFPDRFSGSGSGTDFSLTISRLEP | |
| 180 | QKPGRAPRLL | LYGASSRAT | GFPDRFSGSGSGTDFSLTISRLEP | |
| 184 | QKPGRAPRLL | MYGASSRAT | GFPDRFSGSGSGTDFSLTISRLEP | |

| Kabat No. | 81-88 | CDR (89–97, incl. 95A–F) | 98–108 |
|---|---|---|---|
| SEQ ID NO: | 1 2 3 4 5 6 7 8 | 9 9 0 1 2 3 4 5 A B C D E F 6 7 | 8 9 0 1 2 3 4 5 6 7 8 |
| 100 | EDFAVYYC | QQFDSSP       T | FGGGTKVEIKR |
| 104 | EDFAVYYC | QQYDYSP      LT | FGGGTKVEMKKR |
| 108 | EDFAVYYC | QQFDTLP      HT | FGGGTRLDEIKR |
| 112 | EDFAIYFC | QQYGSSTP     IT | FGHGQTRLLEIKR |
| 116 | EDFAVYYC | QQFDNLP      VT | FGGGTRVDEIKR |
| 120 | EDSAVYYC | QQFDTSP      LT | FGGGTKVEEIKR |
| 124 | EDFAVYYC | QQFDSSP      LT | FGGGTKVEEIKR |
| 128 | EDFAVYYC | QQFDSSP      PT | FGGGTKVEEIKR |
| 132 | EDFAVYYC | QQFDSSP      PT | FGGGTKVKLEIKR |
| 136 | EDFAIYYC | QQFDSSPP     YT | FGGGTKVEEIKR |
| 140 | EDSAVYYC | QQFDGSSNWP   WT | FGGGTKVEEIKR |
| 144 | EDFAVYYC | QQFDSSP      LT | FGGGTKVEEIKR |
| 148 | EDSAVYYC | QQFDSSP      LS | FGGGTKVEEIKR |
| 152 | EDFAIYYC | QQFDSSP      PT | FGGGTKVEEIKR |
| 156 | EDFAVYYC | QQFDSSP      PT | FGGGTKVEEIKR |
| 160 | EDFAMYYC | QQFDSSP      PT | FGGGTKVEEIKR |
| 164 | EDFAVYYC | QQFDSSP      PT | FGGGTKVEEIKR |
| 168 | EDFAVYYC | QQFDSSP      PT | FGGGTKVEEIKR |
| 172 | EDFAMYYC | QQFDSSP      PT | FGGGTKVEEIKR |
| 176 | EDFAVYYC | QQFDSSP      PT | FGGGTKVEEIKR |
| 180 | EDFAVYYC | QQFDSSP      PT | FGGGTKVEEIKR |
| 184 | EDFAVYYC | QQFDSSP      PT | FGGGTRIDEIKR |

| Kabat No. | | | | | | | | | | 1 | | | | | | | | | | 2 | | | | | | | | | | 3 | | | | | | | | | | 4 | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | A | B | 6 | 7 | 8 | 9 | 0 | 1 | 2 | 3 |
| SEQ ID NO. 4 | E | V | Q | L | L | E | S | G | G | G | L | V | Q | P | G | G | S | L | R | L | S | C | A | A | S | G | F | T | F | S | W | Y | Y | V | M | G | – | – | W | V | R | Q | A | P | G | K |
| 188 | E | V | Q | L | L | E | S | G | G | G | L | V | Q | P | G | G | S | L | R | L | S | C | A | A | S | G | F | T | F | S | W | Y | V | V | M | G | – | – | W | V | R | Q | A | P | G | K |
| 196 | E | V | Q | L | L | E | S | G | G | G | L | V | Q | P | G | G | S | L | R | L | S | C | A | A | S | G | F | T | F | S | W | Y | V | V | M | S | – | – | W | V | R | Q | A | P | G | K |
| 204 | E | V | Q | L | L | E | S | G | G | G | L | V | Q | P | G | G | S | L | R | L | S | C | A | A | S | G | F | T | F | S | W | Y | V | V | M | G | – | – | W | V | R | Q | A | P | G | K |
| 212 | E | V | Q | L | L | E | S | G | G | G | L | V | Q | P | G | G | S | L | R | L | S | C | A | A | S | G | F | T | F | S | W | Y | V | V | M | G | – | – | W | V | R | Q | A | P | G | K |
| 220 | E | V | Q | L | L | E | S | G | G | G | L | V | Q | P | G | G | S | L | R | L | S | C | A | A | S | G | F | T | F | S | W | Y | V | V | M | G | – | – | W | V | R | Q | A | P | G | K |

| Kabat No. | | | | | 5 | | | | | | | | | | | | 6 | | | | | | | | | | 7 | | | | | | | | | | 8 | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| | 4 | 5 | 6 | 7 | 8 | 9 | 0 | 1 | 2 | A | B | C | 3 | 4 | 5 | 6 | 7 | 8 | 9 | 0 | 1 | 2 | 3 | 4 | 5 | 6 | 7 | 8 | 9 | 0 | 1 | 2 | A | B | C | 3 | 4 | 5 | 6 | 7 |
| SEQ ID NO. 4 | G | L | E | W | V | S | S | I | Y | P | – | – | S | G | G | A | T | N | Y | A | D | S | V | K | G | R | F | T | I | S | R | D | N | S | K | N | T | L | Y | L |
| 188 | G | L | E | W | V | S | S | I | Y | P | – | – | Q | G | G | A | T | S | Y | A | D | S | V | K | G | R | F | T | I | S | R | D | N | S | K | N | T | L | Y | L |
| 196 | G | L | E | W | V | S | S | I | Y | P | – | – | Q | G | G | A | T | N | Y | A | D | S | V | K | G | R | F | T | I | S | R | D | N | S | K | N | T | L | Y | L |
| 204 | G | L | E | W | V | S | S | I | Y | P | – | – | S | G | G | A | T | N | Y | A | D | S | V | K | G | R | F | T | I | S | R | D | N | S | K | N | T | L | Y | L |
| 212 | G | L | E | W | V | S | S | I | Y | P | – | – | S | G | G | A | T | N | Y | A | D | S | V | K | G | R | F | T | I | S | R | D | N | S | K | N | T | L | Y | L |
| 220 | G | L | E | W | V | S | S | I | Y | P | – | – | S | G | G | A | T | N | Y | A | D | S | V | K | G | R | F | T | I | S | R | D | N | S | K | N | T | L | Y | L |

| Kabat No. | | | | | | 9 | | | | | | | | | 10 | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | |
| | 8 | 9 | 0 | 1 | 2 | 3 | 4 | 5 | 6 | 7 | 8 | 9 | 0 | A | B | C | D | E | F | G | H | I | J | K | 1 | 2 | 3 | 4 | 5 | 6 | 7 | 8 | 9 | 0 | 1 | 2 | 3 |
| SEQ ID NO. 4 | Q | M | N | S | L | R | A | E | D | T | A | V | Y | Y | C | A | R | G | N | Y | F | – | – | – | – | – | – | – | – | – | – | – | – | D | Y | W | G | Q | G | T | L | V | T | V | S | S |
| 188 | Q | M | N | S | L | R | A | E | D | T | A | V | Y | Y | C | A | R | G | N | Y | F | – | – | – | – | – | – | – | – | – | – | – | – | D | Y | W | G | Q | G | T | L | V | T | V | S | S |
| 196 | Q | M | N | S | L | R | A | E | D | T | A | V | Y | Y | C | A | R | G | N | Y | F | – | – | – | – | – | – | – | – | – | – | – | – | D | Y | W | G | Q | G | T | L | V | T | V | S | S |
| 204 | Q | M | N | S | L | R | A | E | D | T | A | V | Y | Y | C | A | R | G | N | Y | L | – | – | – | – | – | – | – | – | – | – | – | – | D | Y | W | G | Q | G | T | L | V | T | V | S | S |
| 212 | Q | M | N | S | L | R | A | E | D | T | A | V | Y | Y | C | A | R | G | P | Y | L | – | – | – | – | – | – | – | – | – | – | – | – | D | Y | W | G | Q | G | T | L | V | T | V | S | S |
| 220 | Q | M | N | S | L | R | A | E | D | T | A | V | Y | Y | C | A | R | G | S | Y | L | – | – | – | – | – | – | – | – | – | – | – | – | D | Y | W | G | Q | G | T | L | V | T | V | S | S |

| Kabat No. | | | | | | | | | | 1 | | | | | | | | | | 2 | | | | | | | | | | 3 | | | | | | | | | | | | | | | | | | | | 5 | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | A | B | C | D | E | F | 8 | 9 | 0 | 1 | 2 | 3 | 4 | 5 | 6 | 7 |
| SEQ ID NO: | | | | | | | | | | | | | | | | | | | | | | | | | | | | | | | | | | | | | | | | | | | |
| 160 | D | I | Q | M | T | Q | S | P | G | T | L | S | L | S | P | G | E | G | A | T | L | S | C | R | A | S | Q | S | | | | | | V | S | S | N | Y | F | G | W | Y | Q |
| 192 | D | I | Q | M | T | Q | S | P | G | T | L | S | L | S | P | G | E | G | A | T | L | S | C | R | A | S | Q | S | | | | | | V | S | S | N | Y | F | G | W | Y | Q |
| 200 | D | I | H | M | T | Q | S | P | G | T | L | S | L | S | P | G | E | G | A | T | L | S | C | R | A | S | Q | S | | | | | | V | S | S | N | Y | F | G | W | Y | Q |
| 208 | D | I | Q | M | T | Q | S | P | G | T | L | S | L | S | P | G | E | G | A | T | L | S | C | R | A | S | Q | S | | | | | | V | S | S | N | Y | F | G | W | Y | Q |
| 216 | D | I | Q | M | T | Q | S | P | G | T | L | S | L | S | P | G | E | G | A | T | L | S | C | R | A | S | Q | S | | | | | | V | S | S | N | Y | F | G | W | Y | Q |
| 224 | D | I | Q | M | T | Q | S | P | G | T | L | S | L | S | P | G | E | G | A | T | L | S | C | R | A | S | Q | S | | | | | | V | S | S | N | Y | F | G | W | Y | Q |

| Kabat No. | | | | | | | | | | | | | | | | | 6 | | | | | | | | | | 7 | | | | | | | | | | 8 | 0 |
|---|---|---|---|---|---|---|---|---|---|---|---|---|---|---|---|---|---|---|---|---|---|---|---|---|---|---|---|---|---|---|---|---|---|---|---|---|---|
| | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | 0 | | | | |
| SEQ ID NO: | | | | | | | | | | | | | | | | | | | | | | | | | | | | | | | | | | | | | |
| 160 | Q | K | P | G | Q | A | P | R | R | L | L | I | Y | G | A | S | S | R | A | T | G | I | P | D | R | F | S | G | S | G | S | G | T | D | F | T | L |
| 192 | Q | K | P | G | Q | A | P | R | R | L | L | I | Y | G | A | S | S | R | A | T | G | I | P | D | R | F | S | G | S | G | S | G | T | D | F | T | L |
| 200 | Q | K | P | G | Q | A | P | R | R | L | L | I | Y | G | A | S | S | R | A | T | G | I | P | D | R | F | S | G | S | G | S | G | T | D | F | T | L |
| 208 | Q | K | P | G | Q | A | P | R | R | L | L | I | Y | G | A | S | S | R | A | T | G | I | P | D | R | F | S | G | S | G | S | G | T | D | F | T | L |
| 216 | Q | K | P | G | Q | A | P | R | R | L | L | I | Y | G | A | S | S | R | A | T | G | I | P | D | R | F | S | G | S | G | S | G | T | D | F | T | L |
| 224 | Q | K | P | G | Q | A | P | R | R | L | L | I | Y | G | A | S | S | R | A | T | G | I | P | D | R | F | S | G | S | G | S | G | T | D | F | T | L |

| Kabat No. | | | | | | | | | 9 | | | | | | A | B | C | D | E | F | 6 | 7 | | | | | | | | 1 0 | | | | | | | | |
|---|---|---|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 0 | 1 | 2 | 3 | 4 | 5 | | | | | | 6 | 7 | 8 | 9 | 0 | 1 | 2 | 3 | 4 | 5 | 6 | 7 | 8 | | | | | |
| SEQ ID NO: | | | | | | | | | | | | | | | | | | | | | | | | | | | | | | | | | | | | | | |
| 160 | T | I | S | R | L | E | P | E | D | S | A | V | Y | Y | C | Q | Q | F | D | S | S | P | L | T | F | G | G | G | T | K | V | E | I | K | R | R | | |
| 192 | T | I | S | R | L | E | P | E | D | S | A | V | Y | Y | C | Q | Q | F | D | S | L | P | L | T | F | G | G | G | T | K | V | E | I | K | R | R | | |
| 200 | T | I | S | R | L | E | P | E | D | S | A | V | Y | Y | C | Q | Q | H | D | S | S | P | L | S | F | G | G | G | T | K | V | E | I | K | R | R | | |
| 208 | T | I | S | R | L | E | P | E | D | S | A | V | Y | Y | C | Q | Q | F | D | S | S | P | L | S | F | G | G | G | T | K | V | E | I | K | R | R | | |
| 216 | T | I | S | R | L | E | P | E | D | S | A | V | Y | Y | C | Q | Q | F | D | S | S | P | L | T | F | G | G | G | T | K | V | E | I | K | R | R | | |
| 224 | T | I | S | R | L | E | P | E | D | S | A | V | Y | Y | C | Q | Q | F | D | S | S | P | P | T | F | G | G | G | T | K | V | E | I | K | R | R | | |

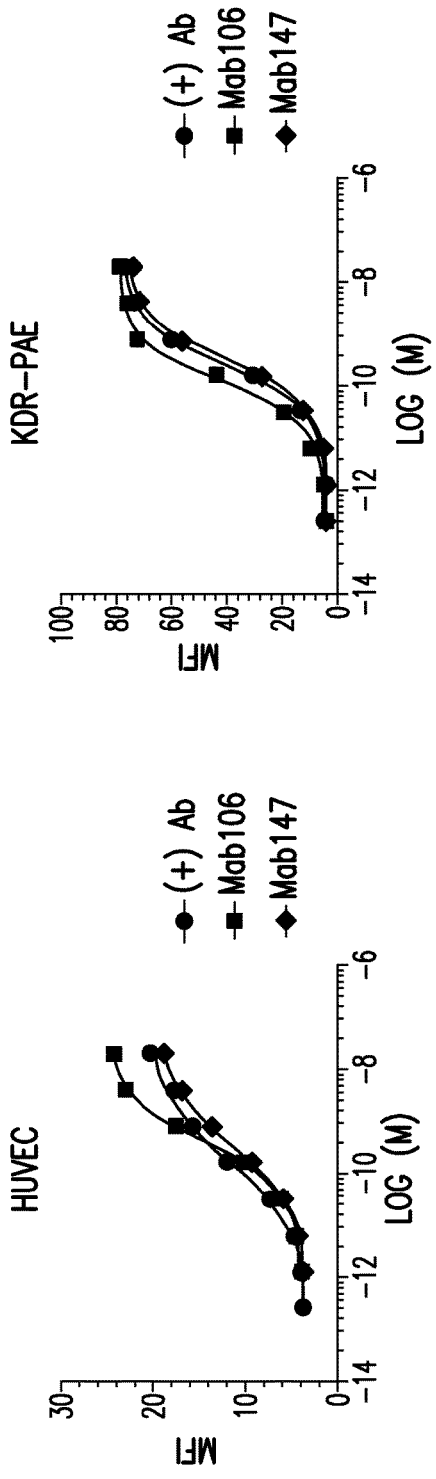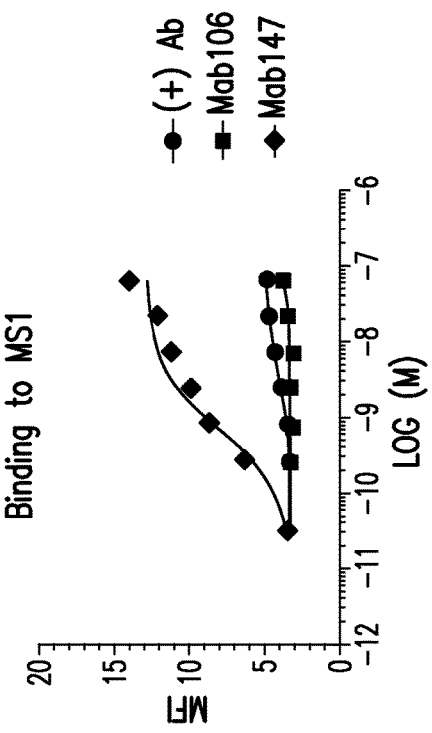
FIG. 8

SEQUENCE LISTING

<160> NUMBER OF SEQ ID NOS: 236

<210> SEQ ID NO 1
<211> LENGTH: 7
<212> TYPE: PRT
<213> ORGANISM: Artificial Sequence
<220> FEATURE:
<223> OTHER INFORMATION: Human antibody library

<400> SEQUENCE: 1

Gly Phe Thr Phe Ser Trp Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: Human antibody library

<400> SEQUENCE: 2

Ile Tyr Pro Ser Gly Gly Ala
1               5

<210> SEQ ID NO 3
<211> LENGTH: 6
<212> TYPE: PRT
<213> ORGANISM: Artificial Sequence
<220> FEATURE:
<223> OTHER INFORMATION: Human antibody library

<400> SEQUENCE: 3

Gly Asn Tyr Phe Asp Tyr
1               5

<210> SEQ ID NO 4
<211> LENGTH: 115
<212> TYPE: PRT
<213> ORGANISM: Artificial Sequence
<220> FEATURE:
<223> OTHER INFORMATION: Human antibody library

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Gly Trp Val Arg Gln Ala Pro Gly Lys Gly Leu Glu Trp Val
        35                  40                  45

Ser Ser Ile Tyr Pro Ser Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Tyr Phe Asp Tyr Trp Gly Gln Gly Thr Leu Val Thr
            100                 105                 110

Val Ser Ser
        115

<210> SEQ ID NO 5
<211> LENGTH: 11
<212> TYPE: PRT

-continued

```
<213> ORGANISM: Artificial Sequence
<220> FEATURE:
<223> OTHER INFORMATION: Human antibody library

<400> SEQUENCE: 5

Gln Gly Asp Ser Leu Arg Ser Tyr Tyr Ala Ser
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Human antibody library

<400> SEQUENCE: 6

Gln Asp Thr Asn Arg Pro Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Human antibody library

<400> SEQUENCE: 7

Gln Ala Trp Asp Ser Asn Thr Ala Val
1               5

<210> SEQ ID NO 8
<211> LENGTH: 109
<212> TYPE: PRT
<213> ORGANISM: Artificial Sequence
<220> FEATURE:
<223> OTHER INFORMATION: Human antibody library

<400> SEQUENCE: 8

Gln Ser Val Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ser Pro Leu Val Val Ile Tyr
        35                  40                  45

Gln Asp Thr Asn Arg Pro Ser Gly Ile Pro Glu Arg Phe Ser Gly Ser
    50                  55                  60

Asn Ser Gly Asn Thr Ala Thr Leu Thr Ile Ser Glu Thr Gln Ala Met
65                  70                  75                  80

Asp Glu Ala Asp Tyr Tyr Cys Gln Ala Trp Asp Ser Asn Thr Ala Val
                85                  90                  95

Phe Gly Gly Gly Thr Lys Leu Thr Val Leu Gly Gln Pro
                100                 105

<210> SEQ ID NO 9
<211> LENGTH: 7
<212> TYPE: PRT
<213> ORGANISM: Artificial Sequence
<220> FEATURE:
<223> OTHER INFORMATION: Human antibody library

<400> SEQUENCE: 9

Gly Phe Thr Phe Ser Trp Tyr
1               5
```

<210> SEQ ID NO 10
<211> LENGTH: 6
<212> TYPE: PRT
<213> ORGANISM: Artificial Sequence
<220> FEATURE:
<223> OTHER INFORMATION: Human antibody library

<400> SEQUENCE: 10

Gly Ser Ser Gly Gly Phe
1               5

<210> SEQ ID NO 11
<211> LENGTH: 7
<212> TYPE: PRT
<213> ORGANISM: Artificial Sequence
<220> FEATURE:
<223> OTHER INFORMATION: Human antibody library

<400> SEQUENCE: 11

Gly Leu Ala Ala Pro Arg Ser
1               5

<210> SEQ ID NO 12
<211> LENGTH: 116
<212> TYPE: PRT
<213> ORGANISM: Artificial Sequence
<220> FEATURE:
<223> OTHER INFORMATION: Human antibody library

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ile Met Leu Trp Val Arg Gln Ala Pro Gly Lys Gly Leu Glu Trp Val
        35                  40                  45

Ser Ser Ile Gly Ser Ser Gly Phe Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Ala Ala Pro Arg Ser Trp Gly Arg Gly Thr Leu Val
            100                 105                 110

Thr Val Ser Ser
        115

<210> SEQ ID NO 13
<211> LENGTH: 13
<212> TYPE: PRT
<213> ORGANISM: Artificial Sequence
<220> FEATURE:
<223> OTHER INFORMATION: Human antibody library

<400> SEQUENCE: 13

Ser Gly Ser Thr Ser Asn Ile Gly Asn Asn Ala Val Ile
1               5                   10

<210> SEQ ID NO 14
<211> LENGTH: 7
<212> TYPE: PRT
<213> ORGANISM: Artificial Sequence
<220> FEATURE:

```
<223> OTHER INFORMATION: Human antibody library

<400> SEQUENCE: 14

Tyr Asp Asp Leu Leu Pro Ser
1               5

<210> SEQ ID NO 15
<211> LENGTH: 11
<212> TYPE: PRT
<213> ORGANISM: Artificial Sequence
<220> FEATURE:
<223> OTHER INFORMATION: Human antibody library

<400> SEQUENCE: 15

Ala Ser Trp Asp Asp Asn Leu Asn Gly Pro Leu
1               5                   10

<210> SEQ ID NO 16
<211> LENGTH: 113
<212> TYPE: PRT
<213> ORGANISM: Artificial Sequence
<220> FEATURE:
<223> OTHER INFORMATION: Human antibody library

<400> SEQUENCE: 16

Gln Ser Ala Leu Thr Gln Pro Pro Ser Val Ser Glu Ala Pro Gly Gln
1               5                   10                  15

Arg Val Thr Ile Ser Cys Ser Gly Ser Thr Ser Asn Ile Gly Asn Asn
            20                  25                  30

Ala Val Ile Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Gly Ser Leu Ala Ile Ser Gly Leu Gln
65                  70                  75                  80

Ser Glu Asp Glu Ala Asp Tyr Tyr Cys Ala Ser Trp Asp Asp Asn Leu
                85                  90                  95

Asn Gly Pro Leu Phe Gly Gly Gly Thr Lys Leu Thr Val Leu Arg Gln
            100                 105                 110

Pro

<210> SEQ ID NO 17
<211> LENGTH: 13
<212> TYPE: PRT
<213> ORGANISM: Artificial Sequence
<220> FEATURE:
<223> OTHER INFORMATION: Human antibody library

<400> SEQUENCE: 17

Ser Gly Ser Ser Ser Asn Ile Gly Thr Tyr Pro Val Asn
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Human antibody library

<400> SEQUENCE: 18

Ser Thr Asp Gln Arg Pro Ser
1               5
```

```
<210> SEQ ID NO 19
<211> LENGTH: 9
<212> TYPE: PRT
<213> ORGANISM: Artificial Sequence
<220> FEATURE:
<223> OTHER INFORMATION: Human antibody library

<400> SEQUENCE: 19

Gln Ala Trp Asp Ser Ser Thr Val Val
1               5

<210> SEQ ID NO 20
<211> LENGTH: 111
<212> TYPE: PRT
<213> ORGANISM: Artificial Sequence
<220> FEATURE:
<223> OTHER INFORMATION: Human antibody library

<400> SEQUENCE: 20

Gln Ser Ala Leu Thr Gln Pro Pro Ser Ala Ser Gly Thr Pro Gly Gln
1               5                   10                  15

Arg Val Thr Ile Ser Cys Ser Gly Ser Ser Asn Ile Gly Thr Tyr
            20                  25                  30

Pro Val Asn Trp Tyr Gln Gln Leu Pro Gly Ala Ala Pro Lys Leu Leu
        35                  40                  45

Ile Tyr Ser Thr Asp Gln Arg Pro Ser Gly Val Pro Asp Arg Phe Ser
    50                  55                  60

Gly Ser Asn Ser Gly Asn Thr Ala Thr Leu Thr Ile Ser Gly Thr Gln
65                  70                  75                  80

Ala Met Asp Glu Ala Asp Tyr Tyr Cys Gln Ala Trp Asp Ser Ser Thr
                85                  90                  95

Val Val Phe Gly Gly Gly Thr Lys Leu Thr Val Leu Gly Gln Pro
            100                 105                 110

<210> SEQ ID NO 21
<211> LENGTH: 11
<212> TYPE: PRT
<213> ORGANISM: Artificial Sequence
<220> FEATURE:
<223> OTHER INFORMATION: Human antibody library

<400> SEQUENCE: 21

Ser Gly Asp Lys Leu Gly Asp Glu Tyr Ala Ser
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Human antibody library

<400> SEQUENCE: 22

Gln Asp Asn Lys Arg Pro Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Human antibody library

<400> SEQUENCE: 23
```

```
Gln Ala Trp Asp Ser Ser Thr Val Val
1               5

<210> SEQ ID NO 24
<211> LENGTH: 109
<212> TYPE: PRT
<213> ORGANISM: Artificial Sequence
<220> FEATURE:
<223> OTHER INFORMATION: Human antibody library

<400> SEQUENCE: 24

Gln Ser Ala Leu Thr Gln Pro Pro Ser Val Ser Val Ser Pro Gly Gln
1               5                   10                  15

Thr Ala Ser Ile Thr Cys Ser Gly Asp Lys Leu Gly Asp Glu Tyr Ala
            20                  25                  30

Ser Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu Gly Gln Pro
            100                 105

<210> SEQ ID NO 25
<211> LENGTH: 11
<212> TYPE: PRT
<213> ORGANISM: Artificial Sequence
<220> FEATURE:
<223> OTHER INFORMATION: Human antibody library

<400> SEQUENCE: 25

Ser Gly Asp Asn Leu Arg His Glu Tyr Ser Ser
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Human antibody library

<400> SEQUENCE: 26

Gln Asp Ser Lys Arg Pro Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Human antibody library

<400> SEQUENCE: 27

Gln Ala Trp Gly Ser Ser Thr Val Val
1               5

<210> SEQ ID NO 28
<211> LENGTH: 109
<212> TYPE: PRT
<213> ORGANISM: Artificial Sequence
```

<220> FEATURE:
<223> OTHER INFORMATION: Human antibody library

<400> SEQUENCE: 28

Gln Tyr Glu Leu Thr Gln Pro Pro Ser Val Ser Val Ser Pro Gly Gln
1               5                   10                  15

Thr Ala Ser Ile Thr Cys Ser Gly Asp Asn Leu Arg His Glu Tyr Ser
            20                  25                  30

Ser Trp Tyr Gln Gln Arg Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Gly Ser Ser Thr Val Val
                85                  90                  95

Phe Gly Gly Gly Thr Lys Leu Thr Val Leu Arg Gln Pro
            100                 105

<210> SEQ ID NO 29
<211> LENGTH: 11
<212> TYPE: PRT
<213> ORGANISM: Artificial Sequence
<220> FEATURE:
<223> OTHER INFORMATION: Human antibody library

<400> SEQUENCE: 29

Ser Gly Glu Lys Leu Gly Asp Glu Tyr Ala Ser
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Human antibody library

<400> SEQUENCE: 30

Gln Asp Asn Lys Arg Pro Ser
1               5

<210> SEQ ID NO 31
<211> LENGTH: 9
<212> TYPE: PRT
<213> ORGANISM: Artificial Sequence
<220> FEATURE:
<223> OTHER INFORMATION: Human antibody library

<400> SEQUENCE: 31

Gln Ala Trp Asp Ser Ser Thr Leu Leu
1               5

<210> SEQ ID NO 32
<211> LENGTH: 109
<212> TYPE: PRT
<213> ORGANISM: Artificial Sequence
<220> FEATURE:
<223> OTHER INFORMATION: Human antibody library

<400> SEQUENCE: 32

Gln Ser Val Leu Thr Gln Pro Pro Ser Val Ser Val Ser Pro Gly Gln
1               5                   10                  15

Thr Ala Ser Ile Thr Cys Ser Gly Glu Lys Leu Gly Asp Glu Tyr Ala

```
                20                  25                  30

Ser Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Leu Leu
                85                  90                  95

Phe Gly Gly Gly Thr Lys Leu Thr Val Leu Gly Gln Pro
            100                 105

<210> SEQ ID NO 33
<211> LENGTH: 11
<212> TYPE: PRT
<213> ORGANISM: Artificial Sequence
<220> FEATURE:
<223> OTHER INFORMATION: from human Fab library

<400> SEQUENCE: 33

Ser Gly Glu Lys Leu Gly Asp Glu Tyr Ala Ser
1               5                   10

<210> SEQ ID NO 34
<211> LENGTH: 7
<212> TYPE: PRT
<213> ORGANISM: Artificial Sequence
<220> FEATURE:
<223> OTHER INFORMATION: from human Fab library

<400> SEQUENCE: 34

Gln Asp Asn Lys Arg Pro Ser
1               5

<210> SEQ ID NO 35
<211> LENGTH: 9
<212> TYPE: PRT
<213> ORGANISM: Artificial Sequence
<220> FEATURE:
<223> OTHER INFORMATION: from human Fab library

<400> SEQUENCE: 35

Gln Ala Trp Asp Ser Ser Thr Leu Leu
1               5

<210> SEQ ID NO 36
<211> LENGTH: 109
<212> TYPE: PRT
<213> ORGANISM: Artificial Sequence
<220> FEATURE:
<223> OTHER INFORMATION: from human Fab library

<400> SEQUENCE: 36

Gln Ser Glu Leu Thr Gln Pro Pro Ser Val Ser Val Ser Pro Gly Gln
1               5                   10                  15

Thr Ala Ser Ile Thr Cys Ser Gly Glu Lys Leu Gly Asp Glu Tyr Ala
            20                  25                  30

Ser Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
```

```
                65                  70                  75                  80
Asp Glu Ala Asp Tyr Tyr Cys Gln Ala Trp Asp Ser Ser Thr Leu Leu
                    85                  90                  95
Phe Gly Gly Gly Thr Lys Leu Thr Val Leu Gly Gln Pro
                100                 105
```

<210> SEQ ID NO 37
<211> LENGTH: 11
<212> TYPE: PRT
<213> ORGANISM: Artificial Sequence
<220> FEATURE:
<223> OTHER INFORMATION: Human antibody library

<400> SEQUENCE: 37

```
Thr Gly Asp Lys Leu Gly Asp Gln Phe Ala Ser
1               5                   10
```

<210> SEQ ID NO 38
<211> LENGTH: 7
<212> TYPE: PRT
<213> ORGANISM: Artificial Sequence
<220> FEATURE:
<223> OTHER INFORMATION: Human antibody library

<400> SEQUENCE: 38

```
Gln Asn Asp Lys Arg Pro Ser
1               5
```

<210> SEQ ID NO 39
<211> LENGTH: 9
<212> TYPE: PRT
<213> ORGANISM: Artificial Sequence
<220> FEATURE:
<223> OTHER INFORMATION: Human antibody library

<400> SEQUENCE: 39

```
Gln Ala Trp Asp Phe Ser Ser Ala Leu
1               5
```

<210> SEQ ID NO 40
<211> LENGTH: 109
<212> TYPE: PRT
<213> ORGANISM: Artificial Sequence
<220> FEATURE:
<223> OTHER INFORMATION: Human antibody library

<400> SEQUENCE: 40

```
Gln Tyr Glu Leu Thr Gln Pro Pro Ser Val Ser Val Ser Pro Gly Gln
1               5                   10                  15
Thr Ala Thr Ile Thr Cys Thr Gly Asp Lys Leu Gly Asp Gln Phe Ala
                20                  25                  30
Ser Trp Tyr Gln His Lys Pro Gly Gln Ser Pro Ile Leu Leu Ile Tyr
            35                  40                  45
Gln Asn Asp Lys Arg Pro Ser Gly Ile Pro Asp Arg Phe Ser Gly Ser
        50                  55                  60
Asp Ser Gly Asn Thr Ala Thr Leu Thr Ile Ser Gly Thr Gln Ala Met
65                  70                  75                  80
Asp Glu Ala His Tyr Tyr Cys Gln Ala Trp Asp Phe Ser Ser Ala Leu
                85                  90                  95
Phe Gly Gly Gly Thr Lys Leu Thr Val Leu Gly Gln Pro
                100                 105
```

```
<210> SEQ ID NO 41
<211> LENGTH: 11
<212> TYPE: PRT
<213> ORGANISM: Artificial Sequence
<220> FEATURE:
<223> OTHER INFORMATION: Human antibody library

<400> SEQUENCE: 41

Ser Gly Gln Ile Leu Gly Glu Arg Ser Ala Ser
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Human antibody library

<400> SEQUENCE: 42

Gln Ser Ser Gln Arg Pro Ser
1               5

<210> SEQ ID NO 43
<211> LENGTH: 8
<212> TYPE: PRT
<213> ORGANISM: Artificial Sequence
<220> FEATURE:
<223> OTHER INFORMATION: Human antibody library

<400> SEQUENCE: 43

Gln Thr Trp Asp Thr Ser Ile Leu
1               5

<210> SEQ ID NO 44
<211> LENGTH: 108
<212> TYPE: PRT
<213> ORGANISM: Artificial Sequence
<220> FEATURE:
<223> OTHER INFORMATION: Human antibody library

<400> SEQUENCE: 44

Gln Ser Ala Leu Thr Gln Pro Pro Ser Val Ser Val Ser Pro Gly His
1               5                   10                  15

Thr Ala Thr Ile Thr Cys Ser Gly Gln Ile Leu Gly Glu Arg Ser Ala
                20                  25                  30

Ser Trp Tyr Gln Gln Arg Pro Gly Gln Ala Pro Val Leu Val Leu Tyr
            35                  40                  45

Gln Ser Ser Gln Arg Pro Ser Gly Ile Pro Glu Arg Phe Ser Gly Ser
        50                  55                  60

Ile Ser Gly Asn Thr Ala Thr Leu Thr Ile Ser Gly Ala Gln Ser Ile
65                  70                  75                  80

Asp Glu Ala Asp Tyr Tyr Cys Gln Thr Trp Asp Thr Ser Ile Leu Phe
                85                  90                  95

Gly Gly Gly Thr Lys Leu Thr Val Leu Ser Gln Pro
            100                 105

<210> SEQ ID NO 45
<211> LENGTH: 11
<212> TYPE: PRT
<213> ORGANISM: Artificial Sequence
<220> FEATURE:
<223> OTHER INFORMATION: Human antibody library

<400> SEQUENCE: 45
```

```
Ser Gly Asp Ala Leu Gly Asn Asn Tyr Ala Ser
1               5                   10
```

<210> SEQ ID NO 46
<211> LENGTH: 7
<212> TYPE: PRT
<213> ORGANISM: Artificial Sequence
<220> FEATURE:
<223> OTHER INFORMATION: Human antibody library

<400> SEQUENCE: 46

```
Gln Asp Thr Lys Arg Pro Ser
1               5
```

<210> SEQ ID NO 47
<211> LENGTH: 10
<212> TYPE: PRT
<213> ORGANISM: Artificial Sequence
<220> FEATURE:
<223> OTHER INFORMATION: Human antibody library

<400> SEQUENCE: 47

```
Gln Thr Trp Asp Arg Asn Thr Pro Tyr Val
1               5                   10
```

<210> SEQ ID NO 48
<211> LENGTH: 110
<212> TYPE: PRT
<213> ORGANISM: Artificial Sequence
<220> FEATURE:
<223> OTHER INFORMATION: Human antibody library

<400> SEQUENCE: 48

```
Gln Ser Ala Leu Thr Gln Pro Pro Ser Val Ser Val Ser Pro Gly Gln
1               5                   10                  15

Thr Ala Ile Ile Thr Cys Ser Gly Asp Ala Leu Gly Asn Asn Tyr Ala
            20                  25                  30

Ser Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Ser Ser Gly Asn Thr Ala Thr Leu Thr Ile Ser Glu Thr Gln Thr Met
65                  70                  75                  80

Asp Glu Ala Asp Tyr Tyr Cys Gln Thr Trp Asp Arg Asn Thr Pro Tyr
                85                  90                  95

Val Phe Gly Ala Gly Thr Lys Val Thr Val Leu Gly Gln Pro
            100                 105                 110
```

<210> SEQ ID NO 49
<211> LENGTH: 13
<212> TYPE: PRT
<213> ORGANISM: Artificial Sequence
<220> FEATURE:
<223> OTHER INFORMATION: Human antibody library

<400> SEQUENCE: 49

```
Ser Gly Ser Ser Ser Asn Ile Gly Thr Asn Thr Leu Asn
1               5                   10
```

<210> SEQ ID NO 50
<211> LENGTH: 7
<212> TYPE: PRT
<213> ORGANISM: Artificial Sequence
<220> FEATURE:

<223> OTHER INFORMATION: Human antibody library

<400> SEQUENCE: 50

Ala Asn Asn Gln Arg Pro Ser
1               5

<210> SEQ ID NO 51
<211> LENGTH: 11
<212> TYPE: PRT
<213> ORGANISM: Artificial Sequence
<220> FEATURE:
<223> OTHER INFORMATION: Human antibody library

<400> SEQUENCE: 51

Ala Thr Trp Asp Asp Ser Leu Ile Gly Pro Val
1               5                   10

<210> SEQ ID NO 52
<211> LENGTH: 113
<212> TYPE: PRT
<213> ORGANISM: Artificial Sequence
<220> FEATURE:
<223> OTHER INFORMATION: Human antibody library

<400> SEQUENCE: 52

Gln Ser Ala Leu Thr Gln Pro Pro Ser Val Ser Gly Thr Pro Gly Gln
1               5                   10                  15

Arg Val Thr Ile Ser Cys Ser Gly Ser Ser Asn Ile Gly Thr Asn
            20                  25                  30

Thr Leu Asn Trp Tyr Gln Gln Leu Pro Gly Thr Ala Pro Lys Leu Leu
        35                  40                  45

Ile Tyr Ala Asn Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Asp Asp Glu Ala Asp Tyr Tyr Cys Ala Thr Trp Asp Asp Ser Leu
                85                  90                  95

Ile Gly Pro Val Phe Gly Gly Gly Thr Lys Leu Thr Val Leu Gly Gln
            100                 105                 110

Pro

<210> SEQ ID NO 53
<211> LENGTH: 13
<212> TYPE: PRT
<213> ORGANISM: Artificial Sequence
<220> FEATURE:
<223> OTHER INFORMATION: from human Fab library

<400> SEQUENCE: 53

Ser Gly Ser Thr Ser Asn Ile Gly Asn Asn Ala Val Ile
1               5                   10

<210> SEQ ID NO 54
<211> LENGTH: 7
<212> TYPE: PRT
<213> ORGANISM: Artificial Sequence
<220> FEATURE:
<223> OTHER INFORMATION: from human Fab library

<400> SEQUENCE: 54

Tyr Asp Asp Leu Leu Pro Ser
1               5

<210> SEQ ID NO 55
<211> LENGTH: 11
<212> TYPE: PRT
<213> ORGANISM: Artificial Sequence
<220> FEATURE:
<223> OTHER INFORMATION: from human Fab library

<400> SEQUENCE: 55

Ala Ser Trp Asp Asp Asn Leu Asn Gly Pro Leu
1               5                   10

<210> SEQ ID NO 56
<211> LENGTH: 113
<212> TYPE: PRT
<213> ORGANISM: Artificial Sequence
<220> FEATURE:
<223> OTHER INFORMATION: from human Fab library

<400> SEQUENCE: 56

Gln Tyr Glu Leu Thr Gln Pro Pro Ser Val Ser Glu Ala Pro Gly Gln
1               5                   10                  15

Arg Val Thr Ile Ser Cys Ser Gly Ser Thr Ser Asn Ile Gly Asn Asn
            20                  25                  30

Ala Val Ile Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Gly Ser Leu Ala Ile Ser Gly Leu Gln
65                  70                  75                  80

Ser Glu Asp Glu Ala Asp Tyr Tyr Cys Ala Ser Trp Asp Asp Asn Leu
                85                  90                  95

Asn Gly Pro Leu Phe Gly Gly Gly Thr Lys Leu Thr Val Leu Arg Gln
            100                 105                 110

Pro

<210> SEQ ID NO 57
<211> LENGTH: 13
<212> TYPE: PRT
<213> ORGANISM: Artificial Sequence
<220> FEATURE:
<223> OTHER INFORMATION: Human antibody library

<400> SEQUENCE: 57

Ser Gly Ser Ser Ser Asn Leu Gly Ser Asn Thr Val Asn
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Human antibody library

<400> SEQUENCE: 58

Thr Asn Ser Gln Arg Pro Ser
1               5

<210> SEQ ID NO 59
<211> LENGTH: 11
<212> TYPE: PRT
<213> ORGANISM: Artificial Sequence
<220> FEATURE:
<223> OTHER INFORMATION: Human antibody library

<400> SEQUENCE: 59

Ala Ala Trp Asp Asp Ser Leu Asn Gly Trp Val
1               5                   10

<210> SEQ ID NO 60
<211> LENGTH: 113
<212> TYPE: PRT
<213> ORGANISM: Artificial Sequence
<220> FEATURE:
<223> OTHER INFORMATION: Human antibody library

<400> SEQUENCE: 60

Gln Ser Glu Leu Thr Gln Pro Pro Ser Ala Ser Gly Thr Pro Gly Gln
1               5                   10                  15

Arg Val Thr Ile Ser Cys Ser Gly Ser Ser Asn Leu Gly Ser Asn
            20                  25                  30

Thr Val Asn Trp Tyr Gln Gln Leu Pro Gly Thr Ala Pro Lys Leu Leu
        35                  40                  45

Ile Tyr Thr Asn Ser Gln Arg Pro Ser Gly Val Pro Asp Arg Phe Ser
    50                  55                  60

Gly Leu Gln Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Ser Gln
            100                 105                 110

Pro

<210> SEQ ID NO 61
<211> LENGTH: 13
<212> TYPE: PRT
<213> ORGANISM: Artificial Sequence
<220> FEATURE:
<223> OTHER INFORMATION: Human antibody library

<400> SEQUENCE: 61

Ser Gly Ser Ser Ser Asn Ile Glu Ser Asn Tyr Val Tyr
1               5                   10

<210> SEQ ID NO 62
<211> LENGTH: 7
<212> TYPE: PRT
<213> ORGANISM: Artificial Sequence
<220> FEATURE:
<223> OTHER INFORMATION: Human antibody library

<400> SEQUENCE: 62

Thr Asn Asn Gln Arg Pro Ser
1               5

<210> SEQ ID NO 63
<211> LENGTH: 11
<212> TYPE: PRT
<213> ORGANISM: Artificial Sequence
<220> FEATURE:
<223> OTHER INFORMATION: Human antibody library

<400> SEQUENCE: 63

Ala Ser Trp Asp Asp Ser Leu Ser Gly Val Val
1               5                   10

<210> SEQ ID NO 64
<211> LENGTH: 113
<212> TYPE: PRT
<213> ORGANISM: Artificial Sequence
<220> FEATURE:
<223> OTHER INFORMATION: Human antibody library

<400> SEQUENCE: 64

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Glu Ser Asn
            20                  25                  30

Tyr Val Tyr Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Gly Val Val Phe Gly Gly Gly Thr Lys Leu Thr Val Leu Arg Gln
            100                 105                 110

Pro

<210> SEQ ID NO 65
<211> LENGTH: 14
<212> TYPE: PRT
<213> ORGANISM: Artificial Sequence
<220> FEATURE:
<223> OTHER INFORMATION: Human antibody library

<400> SEQUENCE: 65

Thr Gly Ser Ser Asn Asp Ile Gly Ser Tyr Asp Tyr Val Ser
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Human antibody library

<400> SEQUENCE: 66

Asp Val Asn Asn Arg Pro Ser
1               5

<210> SEQ ID NO 67
<211> LENGTH: 9
<212> TYPE: PRT
<213> ORGANISM: Artificial Sequence
<220> FEATURE:
<223> OTHER INFORMATION: Human antibody library

<400> SEQUENCE: 67

Met Ser Tyr Thr Ile Thr Ala Leu Leu
1               5

<210> SEQ ID NO 68
<211> LENGTH: 112
<212> TYPE: PRT
<213> ORGANISM: Artificial Sequence
<220> FEATURE:
<223> OTHER INFORMATION: Human antibody library

<400> SEQUENCE: 68

Gln Ser Glu Leu Thr Gln Pro Asp Ser Val Ser Gly Ser Pro Gly Gln
1               5                   10                  15

Ser Ile Thr Ile Ser Cys Thr Gly Ser Ser Asn Asp Ile Gly Ser Tyr
            20                  25                  30

Asp Tyr Val Ser Trp Tyr Gln Gln His Pro Gly Arg Ala Pro Lys Phe
        35                  40                  45

Ile Leu Tyr Asp Val Asn Asn Arg Pro Ser Gly Val Ala Asp Arg Phe
    50                  55                  60

Ser Gly Phe Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Ala Leu Leu Phe Gly Gly Gly Thr Arg Val Thr Val Leu Gly Gln Pro
            100                 105                 110

<210> SEQ ID NO 69
<211> LENGTH: 14
<212> TYPE: PRT
<213> ORGANISM: Artificial Sequence
<220> FEATURE:
<223> OTHER INFORMATION: Human antibody library

<400> SEQUENCE: 69

Thr Gly Ser Ser His Asp Ile Gly Ser Tyr Asp Tyr Val Ser
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Human antibody library

<400> SEQUENCE: 70

Asp Val Asn Asn Arg Pro Ser
1               5

<210> SEQ ID NO 71
<211> LENGTH: 9
<212> TYPE: PRT
<213> ORGANISM: Artificial Sequence
<220> FEATURE:
<223> OTHER INFORMATION: Human antibody library

<400> SEQUENCE: 71

Met Ser Tyr Thr Ile Thr Thr Leu Leu
1               5

<210> SEQ ID NO 72
<211> LENGTH: 112
<212> TYPE: PRT
<213> ORGANISM: Artificial Sequence
<220> FEATURE:
<223> OTHER INFORMATION: Human antibody library

<400> SEQUENCE: 72

Gln Ser Ala Leu Thr Gln Pro Asp Ser Val Ser Gly Ser Pro Gly Gln
1               5                   10                  15

Ser Ile Thr Ile Ser Cys Thr Gly Ser Ser His Asp Ile Gly Ser Tyr
            20                  25                  30

Asp Tyr Val Ser Trp Tyr Gln Tyr His Pro Gly Lys Ala Pro Lys Phe

```
                35                  40                  45
Ile Leu Tyr Asp Val Asn Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 73
<211> LENGTH: 14
<212> TYPE: PRT
<213> ORGANISM: Artificial Sequence
<220> FEATURE:
<223> OTHER INFORMATION: Human antibody library

<400> SEQUENCE: 73

Ala Gly Thr Ser Ser Asp Val Gly Ala Tyr Asp Tyr Val Ser
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Human antibody library

<400> SEQUENCE: 74

Asp Val Tyr Asn Arg Pro Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Human antibody library

<400> SEQUENCE: 75

Met Ser Tyr Thr Ile Thr Thr Leu Leu
1               5

<210> SEQ ID NO 76
<211> LENGTH: 112
<212> TYPE: PRT
<213> ORGANISM: Artificial Sequence
<220> FEATURE:
<223> OTHER INFORMATION: Human antibody library

<400> SEQUENCE: 76

Gln Ser Ala Leu Thr Gln Pro Ala Ser Met Ser Gly Ser Arg Gly Gln
1               5                   10                  15

Ser Ile Thr Ile Ser Cys Ala Gly Thr Ser Ser Asp Val Gly Ala Tyr
            20                  25                  30

Asp Tyr Val Ser Trp Tyr Lys His Leu Pro Gly Asn Ala Pro Lys Phe
        35                  40                  45

Ile Leu Tyr Asp Val Tyr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
```

```
                    85                  90                  95

Thr Leu Phe Gly Thr Gly Thr Arg Val Thr Val Leu Ser Gln Pro
            100                 105                 110

<210> SEQ ID NO 77
<211> LENGTH: 14
<212> TYPE: PRT
<213> ORGANISM: Artificial Sequence
<220> FEATURE:
<223> OTHER INFORMATION: Human antibody library

<400> SEQUENCE: 77

Thr Gly Ser Ser His Asp Ile Gly Ala Tyr Asp Tyr Val Ser
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Human antibody library

<400> SEQUENCE: 78

Asp Val Tyr Asn Arg Pro Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Human antibody library

<400> SEQUENCE: 79

Met Ser Tyr Thr Ile Thr Thr Leu Leu
1               5

<210> SEQ ID NO 80
<211> LENGTH: 112
<212> TYPE: PRT
<213> ORGANISM: Artificial Sequence
<220> FEATURE:
<223> OTHER INFORMATION: Human antibody library

<400> SEQUENCE: 80

Gln Ser Val Leu Thr Gln Pro Asp Ser Val Ser Gly Ser Pro Gly Gln
1               5                   10                  15

Ser Ile Thr Ile Ser Cys Thr Gly Ser Ser His Asp Ile Gly Ala Tyr
            20                  25                  30

Asp Tyr Val Ser Trp Tyr Lys His Leu Pro Gly Asn Ala Pro Lys Phe
        35                  40                  45

Ile Leu Tyr Asp Val Tyr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 81
<211> LENGTH: 14
<212> TYPE: PRT
```

<213> ORGANISM: Artificial Sequence
<220> FEATURE:
<223> OTHER INFORMATION: from human Fab library

<400> SEQUENCE: 81

Thr Gly Ser Ser His Asp Ile Gly Ala Tyr Asp Tyr Val Ser
1               5                   10

<210> SEQ ID NO 82
<211> LENGTH: 7
<212> TYPE: PRT
<213> ORGANISM: Artificial Sequence
<220> FEATURE:
<223> OTHER INFORMATION: from human Fab library

<400> SEQUENCE: 82

Asp Val Tyr Asn Arg Pro Ser
1               5

<210> SEQ ID NO 83
<211> LENGTH: 9
<212> TYPE: PRT
<213> ORGANISM: Artificial Sequence
<220> FEATURE:
<223> OTHER INFORMATION: from human Fab library

<400> SEQUENCE: 83

Met Ser Tyr Thr Ile Thr Thr Leu Leu
1               5

<210> SEQ ID NO 84
<211> LENGTH: 112
<212> TYPE: PRT
<213> ORGANISM: Artificial Sequence
<220> FEATURE:
<223> OTHER INFORMATION: from human Fab library

<400> SEQUENCE: 84

Gln Ser Val Leu Thr Gln Pro Ala Ser Val Ser Gly Ser Pro Gly Gln
1               5                   10                  15

Ser Ile Thr Ile Ser Cys Thr Gly Ser Ser His Asp Ile Gly Ala Tyr
            20                  25                  30

Asp Tyr Val Ser Trp Tyr Lys His Leu Pro Gly Asn Ala Pro Lys Phe
        35                  40                  45

Ile Leu Tyr Asp Val Tyr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 85
<211> LENGTH: 14
<212> TYPE: PRT
<213> ORGANISM: Artificial Sequence
<220> FEATURE:
<223> OTHER INFORMATION: from human Fab library

<400> SEQUENCE: 85

Thr Gly Ser Ser His Asp Ile Gly Ala Tyr Asp Tyr Val Ser
1               5                   10

```
<210> SEQ ID NO 86
<211> LENGTH: 7
<212> TYPE: PRT
<213> ORGANISM: Artificial Sequence
<220> FEATURE:
<223> OTHER INFORMATION: from human Fab library

<400> SEQUENCE: 86

Asp Val Tyr Asn Arg Pro Ser
1               5

<210> SEQ ID NO 87
<211> LENGTH: 9
<212> TYPE: PRT
<213> ORGANISM: Artificial Sequence
<220> FEATURE:
<223> OTHER INFORMATION: from human Fab library

<400> SEQUENCE: 87

Met Ser Tyr Thr Ile Thr Thr Leu Leu
1               5

<210> SEQ ID NO 88
<211> LENGTH: 112
<212> TYPE: PRT
<213> ORGANISM: Artificial Sequence
<220> FEATURE:
<223> OTHER INFORMATION: from human Fab library

<400> SEQUENCE: 88

Gln Ser Val Leu Thr Gln Pro Tyr Ser Val Ser Gly Ser Pro Gly Gln
1               5                   10                  15

Ser Ile Thr Ile Ser Cys Thr Gly Ser Ser His Asp Ile Gly Ala Tyr
            20                  25                  30

Asp Tyr Val Ser Trp Tyr Lys His Leu Pro Gly Asn Ala Pro Lys Phe
        35                  40                  45

Ile Leu Tyr Asp Val Tyr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 89
<211> LENGTH: 14
<212> TYPE: PRT
<213> ORGANISM: Artificial Sequence
<220> FEATURE:
<223> OTHER INFORMATION: Human antibody library

<400> SEQUENCE: 89

Thr Gly Ser Ser His Asp Ile Gly Ala Tyr Asp Tyr Val Ser
1               5                   10

<210> SEQ ID NO 90
<211> LENGTH: 7
<212> TYPE: PRT
<213> ORGANISM: Artificial Sequence
<220> FEATURE:
<223> OTHER INFORMATION: Human antibody library

<400> SEQUENCE: 90
```

```
Asp Val Tyr Asn Arg Pro Ser
1               5

<210> SEQ ID NO 91
<211> LENGTH: 9
<212> TYPE: PRT
<213> ORGANISM: Artificial Sequence
<220> FEATURE:
<223> OTHER INFORMATION: Human antibody library

<400> SEQUENCE: 91

Met Ser Tyr Thr Ile Thr Thr Leu Leu
1               5

<210> SEQ ID NO 92
<211> LENGTH: 112
<212> TYPE: PRT
<213> ORGANISM: Artificial Sequence
<220> FEATURE:
<223> OTHER INFORMATION: Human antibody library

<400> SEQUENCE: 92

Gln Ser Ala Leu Thr Gln Pro Asp Ser Val Ser Gly Ser Pro Gly Gln
1               5                   10                  15

Ser Ile Thr Ile Ser Cys Thr Gly Ser Ser His Asp Ile Gly Ala Tyr
            20                  25                  30

Asp Tyr Val Ser Trp Tyr Lys His Leu Pro Gly Asn Ala Pro Lys Phe
        35                  40                  45

Ile Leu Tyr Asp Val Tyr Asn Arg Pro Ser Gly Val Ser Asp Arg Phe
50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 93
<211> LENGTH: 14
<212> TYPE: PRT
<213> ORGANISM: Artificial Sequence
<220> FEATURE:
<223> OTHER INFORMATION: from human Fab library

<400> SEQUENCE: 93

Thr Gly Ser Ser His Asp Ile Gly Ala Tyr Asp Tyr Val Ser
1               5                   10

<210> SEQ ID NO 94
<211> LENGTH: 7
<212> TYPE: PRT
<213> ORGANISM: Artificial Sequence
<220> FEATURE:
<223> OTHER INFORMATION: from human Fab library

<400> SEQUENCE: 94

Asp Val Tyr Asn Arg Pro Ser
1               5

<210> SEQ ID NO 95
<211> LENGTH: 9
<212> TYPE: PRT
<213> ORGANISM: Artificial Sequence
```

```
<220> FEATURE:
<223> OTHER INFORMATION: from human Fab library

<400> SEQUENCE: 95

Met Ser Tyr Thr Ile Thr Thr Leu Leu
1               5

<210> SEQ ID NO 96
<211> LENGTH: 112
<212> TYPE: PRT
<213> ORGANISM: Artificial Sequence
<220> FEATURE:
<223> OTHER INFORMATION: from human Fab library

<400> SEQUENCE: 96

Gln Ser Glu Leu Thr Gln Pro Asp Ser Val Ser Gly Ser Pro Gly Gln
1               5                   10                  15

Ser Ile Thr Ile Ser Cys Thr Gly Ser Ser His Asp Ile Gly Ala Tyr
            20                  25                  30

Asp Tyr Val Ser Trp Tyr Lys His Leu Pro Gly Asn Ala Pro Lys Phe
        35                  40                  45

Ile Leu Tyr Asp Val Tyr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Pro Asp Asp Glu Ala Asp Tyr Phe Cys Met Ser Tyr Thr Ile Thr
                85                  90                  95

Thr Leu Leu Phe Gly Thr Gly Thr Arg Val Thr Val Leu Ser Gln Pro
            100                 105                 110

<210> SEQ ID NO 97
<211> LENGTH: 12
<212> TYPE: PRT
<213> ORGANISM: Artificial Sequence
<220> FEATURE:
<223> OTHER INFORMATION: Human antibody library

<400> SEQUENCE: 97

Arg Ala Ser Gln Ser Val Ser Ser Ser Tyr Leu Ala
1               5                   10

<210> SEQ ID NO 98
<211> LENGTH: 7
<212> TYPE: PRT
<213> ORGANISM: Artificial Sequence
<220> FEATURE:
<223> OTHER INFORMATION: Human antibody library

<400> SEQUENCE: 98

Gly Ala Ser Ser Arg Ala Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Human antibody library

<400> SEQUENCE: 99

Gln Gln Phe Asp Ser Ser Pro Pro Thr
1               5
```

```
<210> SEQ ID NO 100
<211> LENGTH: 109
<212> TYPE: PRT
<213> ORGANISM: Artificial Sequence
<220> FEATURE:
<223> OTHER INFORMATION: Human antibody library

<400> SEQUENCE: 100

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 101
<211> LENGTH: 12
<212> TYPE: PRT
<213> ORGANISM: Artificial Sequence
<220> FEATURE:
<223> OTHER INFORMATION: Human antibody library

<400> SEQUENCE: 101

Arg Ala Ser Glu Arg Ile Ser Ser Asn Tyr Leu Met
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Human antibody library

<400> SEQUENCE: 102

Gly Ala Ser Ile Arg Ala Thr
1               5

<210> SEQ ID NO 103
<211> LENGTH: 9
<212> TYPE: PRT
<213> ORGANISM: Artificial Sequence
<220> FEATURE:
<223> OTHER INFORMATION: Human antibody library

<400> SEQUENCE: 103

Gln Gln Tyr Tyr Ser Ser Pro Leu Thr
1               5

<210> SEQ ID NO 104
<211> LENGTH: 109
<212> TYPE: PRT
<213> ORGANISM: Artificial Sequence
<220> FEATURE:
<223> OTHER INFORMATION: Human antibody library

<400> SEQUENCE: 104
```

```
Asp Ile Gln Met Thr Gln Ser Pro Gly Thr Leu Ser Val Leu Pro Gly
1               5                   10                  15

Glu Arg Ala Thr Leu Ser Cys Arg Ala Ser Gln Arg Ile Ser Ser Asn
            20                  25                  30

Tyr Leu Met Trp Tyr Gln Gln Lys Pro Gly Gln Ala Pro Arg Leu Leu
        35                  40                  45

Met Tyr Gly Ala Ser Ile Arg Ala Thr Gly Ile Pro Asp Arg Phe Ser
    50                  55                  60

Gly Ser Glu Ser Gly Thr Asp Phe Thr Leu Thr Ile Ser Arg Val Glu
65                  70                  75                  80

Pro Glu Asp Phe Ala Val Tyr Tyr Cys Gln Gln Tyr Tyr Ser Ser Pro
                85                  90                  95

Leu Thr Phe Gly Gly Gly Thr Lys Val Glu Met Lys Arg
                100                 105
```

<210> SEQ ID NO 105
<211> LENGTH: 12
<212> TYPE: PRT
<213> ORGANISM: Artificial Sequence
<220> FEATURE:
<223> OTHER INFORMATION: Human antibody library

<400> SEQUENCE: 105

```
Arg Ala Ser Gln Ser Ile Ser Ser Asn Tyr Leu Ala
1               5                   10
```

<210> SEQ ID NO 106
<211> LENGTH: 7
<212> TYPE: PRT
<213> ORGANISM: Artificial Sequence
<220> FEATURE:
<223> OTHER INFORMATION: Human antibody library

<400> SEQUENCE: 106

```
Gly Ala Ser Ser Arg Ser Thr
1               5
```

<210> SEQ ID NO 107
<211> LENGTH: 9
<212> TYPE: PRT
<213> ORGANISM: Artificial Sequence
<220> FEATURE:
<223> OTHER INFORMATION: Human antibody library

<400> SEQUENCE: 107

```
Gln Gln Phe Asp Thr Leu Pro Ile Thr
1               5
```

<210> SEQ ID NO 108
<211> LENGTH: 109
<212> TYPE: PRT
<213> ORGANISM: Artificial Sequence
<220> FEATURE:
<223> OTHER INFORMATION: Human antibody library

<400> SEQUENCE: 108

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Asn
            20                  25                  30

Tyr Leu Ala Trp Tyr Gln Gln Arg Pro Gly Gln Ala Pro Arg Leu Leu
        35                  40                  45
```

```
Ile Tyr Gly Ala Ser Ser Arg Ser Thr Gly Thr Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Ile Tyr Tyr Cys Gln Gln Phe Asp Thr Leu Pro
                85                  90                  95
Ile Thr Phe Gly Gln Gly Thr Arg Leu Asp Ile Lys Arg
                100                 105
```

<210> SEQ ID NO 109
<211> LENGTH: 13
<212> TYPE: PRT
<213> ORGANISM: Artificial Sequence
<220> FEATURE:
<223> OTHER INFORMATION: Human antibody library

<400> SEQUENCE: 109

```
Arg Ala Ser Gln Ser Ile Arg Ser Ser Gly Tyr Leu Ser
1               5                   10
```

<210> SEQ ID NO 110
<211> LENGTH: 7
<212> TYPE: PRT
<213> ORGANISM: Artificial Sequence
<220> FEATURE:
<223> OTHER INFORMATION: Human antibody library

<400> SEQUENCE: 110

```
Gly Ala Ser Thr Arg Ala Thr
1               5
```

<210> SEQ ID NO 111
<211> LENGTH: 9
<212> TYPE: PRT
<213> ORGANISM: Artificial Sequence
<220> FEATURE:
<223> OTHER INFORMATION: Human antibody library

<400> SEQUENCE: 111

```
Gln Gln Tyr Gly Ser Ser Thr Ile Thr
1               5
```

<210> SEQ ID NO 112
<211> LENGTH: 110
<212> TYPE: PRT
<213> ORGANISM: Artificial Sequence
<220> FEATURE:
<223> OTHER INFORMATION: Human antibody library

<400> SEQUENCE: 112

```
Asp Ile Gln Met Thr Gln Ser Pro Ala Thr Leu Ser Leu Ser Pro Gly
1               5                   10                  15
Glu Arg Ala Thr Leu Ser Cys Arg Ala Ser Gln Ser Ile Arg Ser Ser
                20                  25                  30
Gly Tyr Leu Ser Trp Phe Gln Gln Lys Pro Gly Gln Ala Pro Arg Leu
                35                  40                  45
Leu Ile Tyr Gly Ala Ser Thr Arg Ala Thr Gly Thr Pro Ala Arg Phe
            50                  55                  60
Ser Gly Ser Gly Ser Gly Thr Asp Phe Thr Leu Thr Ile Asp Arg Leu
65                  70                  75                  80
Glu Ser Glu Asp Phe Ala Val Tyr Phe Cys Gln Gln Tyr Gly Ser Ser
                85                  90                  95
```

```
Thr Ile Thr Phe Gly Gln Gly Thr Arg Leu Glu Ile Lys Arg
            100                 105                 110

<210> SEQ ID NO 113
<211> LENGTH: 12
<212> TYPE: PRT
<213> ORGANISM: Artificial Sequence
<220> FEATURE:
<223> OTHER INFORMATION: Human antibody library

<400> SEQUENCE: 113

Arg Ala Ser Gln Ser Val Ser Ser Asn Tyr Leu Gly
1               5                   10

<210> SEQ ID NO 114
<211> LENGTH: 7
<212> TYPE: PRT
<213> ORGANISM: Artificial Sequence
<220> FEATURE:
<223> OTHER INFORMATION: Human antibody library

<400> SEQUENCE: 114

Gly Ala Ser Ser Arg Ala Thr
1               5

<210> SEQ ID NO 115
<211> LENGTH: 9
<212> TYPE: PRT
<213> ORGANISM: Artificial Sequence
<220> FEATURE:
<223> OTHER INFORMATION: Human antibody library

<400> SEQUENCE: 115

Gln Gln Phe Asp Asn Leu Pro Val Thr
1               5

<210> SEQ ID NO 116
<211> LENGTH: 109
<212> TYPE: PRT
<213> ORGANISM: Artificial Sequence
<220> FEATURE:
<223> OTHER INFORMATION: Human antibody library

<400> SEQUENCE: 116

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Asp Asn Leu Pro
                85                  90                  95

Val Thr Phe Gly Gly Gly Thr Lys Val Glu Met Lys Arg
            100                 105

<210> SEQ ID NO 117
<211> LENGTH: 12
<212> TYPE: PRT
<213> ORGANISM: Artificial Sequence
<220> FEATURE:
```

<223> OTHER INFORMATION: Human antibody library

<400> SEQUENCE: 117

Arg Ala Ser Gln Ser Val Ser Ser Asn Tyr Leu Ala
1               5                   10

<210> SEQ ID NO 118
<211> LENGTH: 7
<212> TYPE: PRT
<213> ORGANISM: Artificial Sequence
<220> FEATURE:
<223> OTHER INFORMATION: Human antibody library

<400> SEQUENCE: 118

Gly Ala Ser Ser Arg Ala Thr
1               5

<210> SEQ ID NO 119
<211> LENGTH: 9
<212> TYPE: PRT
<213> ORGANISM: Artificial Sequence
<220> FEATURE:
<223> OTHER INFORMATION: Human antibody library

<400> SEQUENCE: 119

Gln Gln Phe Asp Thr Ser Pro Leu Thr
1               5

<210> SEQ ID NO 120
<211> LENGTH: 109
<212> TYPE: PRT
<213> ORGANISM: Artificial Sequence
<220> FEATURE:
<223> OTHER INFORMATION: Human antibody library

<400> SEQUENCE: 120

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
                20                  25                  30

Tyr Leu Ala Trp Tyr Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Asp Thr Ser Pro
                85                  90                  95

Leu Thr Ile Gly Gly Gly Thr Arg Val Asp Ile Lys Arg
                100                 105

<210> SEQ ID NO 121
<211> LENGTH: 12
<212> TYPE: PRT
<213> ORGANISM: Artificial Sequence
<220> FEATURE:
<223> OTHER INFORMATION: Human antibody library

<400> SEQUENCE: 121

Arg Ala Ser Gln Ser Val Ser Ser Asn Tyr Leu Ala
1               5                   10

<210> SEQ ID NO 122

<211> LENGTH: 7
<212> TYPE: PRT
<213> ORGANISM: Artificial Sequence
<220> FEATURE:
<223> OTHER INFORMATION: Human antibody library

<400> SEQUENCE: 122

Gly Ala Ser Ser Arg Ala Thr
1               5

<210> SEQ ID NO 123
<211> LENGTH: 9
<212> TYPE: PRT
<213> ORGANISM: Artificial Sequence
<220> FEATURE:
<223> OTHER INFORMATION: Human antibody library

<400> SEQUENCE: 123

Gln Gln Phe Asp Ser Ser Pro Leu Ser
1               5

<210> SEQ ID NO 124
<211> LENGTH: 109
<212> TYPE: PRT
<213> ORGANISM: Artificial Sequence
<220> FEATURE:
<223> OTHER INFORMATION: Human antibody library

<400> SEQUENCE: 124

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Ser Ala Val Tyr Tyr Cys Gln Gln Phe Asp Ser Ser Pro
                85                  90                  95

Leu Ser Phe Gly Gly Gly Thr Lys Val Glu Ile Lys Arg
            100                 105

<210> SEQ ID NO 125
<211> LENGTH: 12
<212> TYPE: PRT
<213> ORGANISM: Artificial Sequence
<220> FEATURE:
<223> OTHER INFORMATION: Human antibody library

<400> SEQUENCE: 125

Arg Ala Ser Gln Ser Val Ser Ser Trp Tyr Leu Ala
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Human antibody library

<400> SEQUENCE: 126

Gly Ala Ser Asn Arg Ala Thr

<210> SEQ ID NO 127
<211> LENGTH: 9
<212> TYPE: PRT
<213> ORGANISM: Artificial Sequence
<220> FEATURE:
<223> OTHER INFORMATION: Human antibody library

<400> SEQUENCE: 127

Gln Gln Phe Asp Ser Ser Pro Leu Thr
1               5

<210> SEQ ID NO 128
<211> LENGTH: 109
<212> TYPE: PRT
<213> ORGANISM: Artificial Sequence
<220> FEATURE:
<223> OTHER INFORMATION: Human antibody library

<400> SEQUENCE: 128

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Trp
            20                  25                  30

Tyr Leu Ala Trp Tyr Gln Gln Lys Pro Gly Gln Ala Pro Arg Leu Leu
        35                  40                  45

Met Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Phe Asp Ser Ser Pro
                85                  90                  95

Leu Thr Ile Gly Gly Gly Thr Lys Val Glu Ile Lys Arg
            100                 105

<210> SEQ ID NO 129
<211> LENGTH: 12
<212> TYPE: PRT
<213> ORGANISM: Artificial Sequence
<220> FEATURE:
<223> OTHER INFORMATION: Human antibody library

<400> SEQUENCE: 129

Arg Ala Ser Gln Asn Val Gly Ser Ser Tyr Leu Ala
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Human antibody library

<400> SEQUENCE: 130

Gly Ala Ser Ser Arg Ala Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Human antibody library

```
<400> SEQUENCE: 131

Gln Gln Phe Asp Ser Ser Pro Pro Thr
1               5

<210> SEQ ID NO 132
<211> LENGTH: 109
<212> TYPE: PRT
<213> ORGANISM: Artificial Sequence
<220> FEATURE:
<223> OTHER INFORMATION: Human antibody library

<400> SEQUENCE: 132

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Asn Val Gly Ser Ser
                20                  25                  30

Tyr Leu Ala Trp Tyr Gln Gln Lys Pro Gly Gln Ala Pro Arg Leu Leu
            35                  40                  45

Met Tyr Gly Ala Ser Ser Arg Ala Thr Gly Phe Pro Asp Arg Phe Ser
        50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 133
<211> LENGTH: 12
<212> TYPE: PRT
<213> ORGANISM: Artificial Sequence
<220> FEATURE:
<223> OTHER INFORMATION: Human antibody library

<400> SEQUENCE: 133

Arg Ala Ser Gln Ser Val Ser Ser Ser Tyr Leu Ala
1               5                   10

<210> SEQ ID NO 134
<211> LENGTH: 7
<212> TYPE: PRT
<213> ORGANISM: Artificial Sequence
<220> FEATURE:
<223> OTHER INFORMATION: Human antibody library

<400> SEQUENCE: 134

Gly Ala Ser Ser Arg Ala Thr
1               5

<210> SEQ ID NO 135
<211> LENGTH: 9
<212> TYPE: PRT
<213> ORGANISM: Artificial Sequence
<220> FEATURE:
<223> OTHER INFORMATION: Human antibody library

<400> SEQUENCE: 135

Gln Gln Phe Asp Ser Ser Pro Pro Thr
1               5

<210> SEQ ID NO 136
<211> LENGTH: 109
```

```
<212> TYPE: PRT
<213> ORGANISM: Artificial Sequence
<220> FEATURE:
<223> OTHER INFORMATION: Human antibody library

<400> SEQUENCE: 136

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 137
<211> LENGTH: 12
<212> TYPE: PRT
<213> ORGANISM: Artificial Sequence
<220> FEATURE:
<223> OTHER INFORMATION: from human antibody library

<400> SEQUENCE: 137

Arg Ala Ser Gln Ser Val Ser Ser Ser Tyr Leu Ala
1               5                   10

<210> SEQ ID NO 138
<211> LENGTH: 7
<212> TYPE: PRT
<213> ORGANISM: Artificial Sequence
<220> FEATURE:
<223> OTHER INFORMATION: from human antibody library

<400> SEQUENCE: 138

Gly Ala Ser Ser Arg Ala Thr
1               5

<210> SEQ ID NO 139
<211> LENGTH: 9
<212> TYPE: PRT
<213> ORGANISM: Artificial Sequence
<220> FEATURE:
<223> OTHER INFORMATION: from human antibody library

<400> SEQUENCE: 139

Gln Gln Phe Asp Ser Ser Pro Pro Thr
1               5

<210> SEQ ID NO 140
<211> LENGTH: 109
<212> TYPE: PRT
<213> ORGANISM: Artificial Sequence
<220> FEATURE:
<223> OTHER INFORMATION: from human antibody library

<400> SEQUENCE: 140

Asp Ile Gln Met Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Arg Ala Pro Arg Leu Leu
            35                  40                  45

Met Tyr Gly Ala Ser Ser Arg Ala Thr Gly Phe Pro Asp Arg Phe Ser
50                      55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Pro Thr Phe Gly Gly Gly Thr Lys Val Glu Ile Lys Arg
            100                 105
```

<210> SEQ ID NO 141
<211> LENGTH: 12
<212> TYPE: PRT
<213> ORGANISM: Artificial Sequence
<220> FEATURE:
<223> OTHER INFORMATION: Human antibody library

<400> SEQUENCE: 141

```
Arg Ala Ser Gln Ser Val Ser Ser Ser Tyr Leu Ala
1               5                   10
```

<210> SEQ ID NO 142
<211> LENGTH: 7
<212> TYPE: PRT
<213> ORGANISM: Artificial Sequence
<220> FEATURE:
<223> OTHER INFORMATION: Human antibody library

<400> SEQUENCE: 142

```
Gly Ala Ser Ser Arg Ala Thr
1               5
```

<210> SEQ ID NO 143
<211> LENGTH: 10
<212> TYPE: PRT
<213> ORGANISM: Artificial Sequence
<220> FEATURE:
<223> OTHER INFORMATION: Human antibody library

<400> SEQUENCE: 143

```
Gln Gln Phe Gly Ser Ser Pro Pro Tyr Thr
1               5                   10
```

<210> SEQ ID NO 144
<211> LENGTH: 110
<212> TYPE: PRT
<213> ORGANISM: Artificial Sequence
<220> FEATURE:
<223> OTHER INFORMATION: Human antibody library

<400> SEQUENCE: 144

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                      60
```

Gly Ser Gly Ser Gly Thr Asp Tyr Thr Leu Thr Ile Asn Arg Leu Glu
65                  70                  75                  80

Pro Glu Asp Phe Ala Val Tyr Tyr Cys Gln Gln Phe Gly Ser Ser Pro
                85                  90                  95

Pro Tyr Thr Phe Gly Gln Gly Thr Lys Leu Glu Ile Lys Arg
            100                 105                 110

<210> SEQ ID NO 145
<211> LENGTH: 12
<212> TYPE: PRT
<213> ORGANISM: Artificial Sequence
<220> FEATURE:
<223> OTHER INFORMATION: Human antibody library

<400> SEQUENCE: 145

Arg Ala Ser Gln Ser Val Ser Ser Ser Tyr Leu Ala
1               5                   10

<210> SEQ ID NO 146
<211> LENGTH: 7
<212> TYPE: PRT
<213> ORGANISM: Artificial Sequence
<220> FEATURE:
<223> OTHER INFORMATION: Human antibody library

<400> SEQUENCE: 146

Gly Ala Ser Thr Arg Ala Thr
1               5

<210> SEQ ID NO 147
<211> LENGTH: 10
<212> TYPE: PRT
<213> ORGANISM: Artificial Sequence
<220> FEATURE:
<223> OTHER INFORMATION: Human antibody library

<400> SEQUENCE: 147

Gln Gln Phe Asp Asn Trp Pro Pro Trp Thr
1               5                   10

<210> SEQ ID NO 148
<211> LENGTH: 110
<212> TYPE: PRT
<213> ORGANISM: Artificial Sequence
<220> FEATURE:
<223> OTHER INFORMATION: Human antibody library

<400> SEQUENCE: 148

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Thr Arg Ala Thr Gly Ile Pro Pro Arg Phe Ser
        50                  55                  60

Gly Ser Gly Ser Gly Thr Glu Phe Thr Leu Thr Ile Ser Ser Val Gln
65                  70                  75                  80

Ser Glu Asp Phe Ala Ile Tyr Tyr Cys Gln Gln Phe Asp Asn Trp Pro
                85                  90                  95

Pro Trp Thr Phe Gly Gln Gly Thr Lys Val Glu Ile Lys Arg
            100                 105                 110

<210> SEQ ID NO 149
<211> LENGTH: 12
<212> TYPE: PRT
<213> ORGANISM: Artificial Sequence
<220> FEATURE:
<223> OTHER INFORMATION: Human antibody library

<400> SEQUENCE: 149

Arg Ala Ser Gln Ser Val Ser Ser Asn Tyr Phe Gly
1               5                   10

<210> SEQ ID NO 150
<211> LENGTH: 7
<212> TYPE: PRT
<213> ORGANISM: Artificial Sequence
<220> FEATURE:
<223> OTHER INFORMATION: Human antibody library

<400> SEQUENCE: 150

Gly Ala Ser Ser Arg Ala Thr
1               5

<210> SEQ ID NO 151
<211> LENGTH: 9
<212> TYPE: PRT
<213> ORGANISM: Artificial Sequence
<220> FEATURE:
<223> OTHER INFORMATION: Human antibody library

<400> SEQUENCE: 151

Gln Gln Phe Asp Ser Ser Pro Leu Thr
1               5

<210> SEQ ID NO 152
<211> LENGTH: 109
<212> TYPE: PRT
<213> ORGANISM: Artificial Sequence
<220> FEATURE:
<223> OTHER INFORMATION: Human antibody library

<400> SEQUENCE: 152

Asp Ile Gln Met Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Asn
            20                  25                  30

Tyr Phe Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Phe Asp Ser Ser Pro
                85                  90                  95

Leu Thr Phe Gly Gly Gly Thr Lys Val Glu Ile Lys Arg
            100                 105

<210> SEQ ID NO 153
<211> LENGTH: 12
<212> TYPE: PRT
<213> ORGANISM: Artificial Sequence
<220> FEATURE:
<223> OTHER INFORMATION: from human antibody library

<400> SEQUENCE: 153

Arg Ala Ser Gln Ser Val Ser Ser Asn Tyr Leu Ala
1               5                   10

<210> SEQ ID NO 154
<211> LENGTH: 7
<212> TYPE: PRT
<213> ORGANISM: Artificial Sequence
<220> FEATURE:
<223> OTHER INFORMATION: Human antibody library

<400> SEQUENCE: 154

Gly Ala Ser Ser Arg Ala Thr
1               5

<210> SEQ ID NO 155
<211> LENGTH: 9
<212> TYPE: PRT
<213> ORGANISM: Artificial Sequence
<220> FEATURE:
<223> OTHER INFORMATION: Human antibody library

<400> SEQUENCE: 155

Gln Gln Phe Asp Ser Ser Pro Leu Ser
1               5

<210> SEQ ID NO 156
<211> LENGTH: 109
<212> TYPE: PRT
<213> ORGANISM: Artificial Sequence
<220> FEATURE:
<223> OTHER INFORMATION: Human antibody library

<400> SEQUENCE: 156

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Ser Ala Val Tyr Tyr Cys Gln Gln Phe Asp Ser Ser Pro
                85                  90                  95

Leu Ser Phe Gly Gly Gly Thr Lys Val Glu Ile Lys Arg
            100                 105

<210> SEQ ID NO 157
<211> LENGTH: 12
<212> TYPE: PRT
<213> ORGANISM: Artificial Sequence
<220> FEATURE:
<223> OTHER INFORMATION: Human antibody library

<400> SEQUENCE: 157

Arg Ala Ser Gln Ser Val Ser Ser Asn Tyr Leu Ala
1               5                   10

<210> SEQ ID NO 158
<211> LENGTH: 7
<212> TYPE: PRT

```
<213> ORGANISM: Artificial Sequence
<220> FEATURE:
<223> OTHER INFORMATION: Human antibody library

<400> SEQUENCE: 158

Gly Ala Ser Thr Arg Ala Thr
1               5

<210> SEQ ID NO 159
<211> LENGTH: 9
<212> TYPE: PRT
<213> ORGANISM: Artificial Sequence
<220> FEATURE:
<223> OTHER INFORMATION: Human antibody library

<400> SEQUENCE: 159

Gln Gln Phe Asp Ser Ser Pro Leu Ser
1               5

<210> SEQ ID NO 160
<211> LENGTH: 109
<212> TYPE: PRT
<213> ORGANISM: Artificial Sequence
<220> FEATURE:
<223> OTHER INFORMATION: Human antibody library

<400> SEQUENCE: 160

Asp Ile Gln Met Thr Gln Ser Pro Gly Thr Leu Ser Leu Ser Pro Gly
1               5                   10                  15

Asp Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Val Leu
        35                  40                  45

Ile Tyr Gly Ala Ser Thr Arg Ala Thr Gly Ile Pro Asp Arg Phe Thr
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Phe Asp Ser Ser Pro
                85                  90                  95

Leu Ser Phe Gly Gly Gly Thr Lys Val Glu Ile Lys Arg
            100                 105

<210> SEQ ID NO 161
<211> LENGTH: 12
<212> TYPE: PRT
<213> ORGANISM: Artificial Sequence
<220> FEATURE:
<223> OTHER INFORMATION: Human antibody library

<400> SEQUENCE: 161

Arg Ala Ser Gln Ser Leu Asn Asn Asn Tyr Leu Ala
1               5                   10

<210> SEQ ID NO 162
<211> LENGTH: 7
<212> TYPE: PRT
<213> ORGANISM: Artificial Sequence
<220> FEATURE:
<223> OTHER INFORMATION: Human antibody library

<400> SEQUENCE: 162

Gly Ala Ser Thr Arg Ala Thr
1               5
```

<210> SEQ ID NO 163
<211> LENGTH: 9
<212> TYPE: PRT
<213> ORGANISM: Artificial Sequence
<220> FEATURE:
<223> OTHER INFORMATION: Human antibody library

<400> SEQUENCE: 163

Gln Gln Phe Asp Ser Ser Pro Pro Thr
1               5

<210> SEQ ID NO 164
<211> LENGTH: 109
<212> TYPE: PRT
<213> ORGANISM: Artificial Sequence
<220> FEATURE:
<223> OTHER INFORMATION: Human antibody library

<400> SEQUENCE: 164

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Leu Asn Asn Asn
            20                  25                  30

Tyr Leu Ala Trp Tyr Gln Lys Pro Gly Gln Ala Pro Arg Leu Leu
        35                  40                  45

Met Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 165
<211> LENGTH: 12
<212> TYPE: PRT
<213> ORGANISM: Artificial Sequence
<220> FEATURE:
<223> OTHER INFORMATION: Human antibody library

<400> SEQUENCE: 165

Arg Ala Ser His Ser Val Ser Ser Asp Tyr Leu Ala
1               5                   10

<210> SEQ ID NO 166
<211> LENGTH: 7
<212> TYPE: PRT
<213> ORGANISM: Artificial Sequence
<220> FEATURE:
<223> OTHER INFORMATION: Human antibody library

<400> SEQUENCE: 166

Gly Ala Ser Ser Arg Ala Thr
1               5

<210> SEQ ID NO 167
<211> LENGTH: 9
<212> TYPE: PRT
<213> ORGANISM: Artificial Sequence
<220> FEATURE:
<223> OTHER INFORMATION: Human antibody library

<400> SEQUENCE: 167

Gln Gln Phe Asp Ser Ser Pro Pro Thr
1               5

<210> SEQ ID NO 168
<211> LENGTH: 109
<212> TYPE: PRT
<213> ORGANISM: Artificial Sequence
<220> FEATURE:
<223> OTHER INFORMATION: Human antibody library

<400> SEQUENCE: 168

Asp Ile Gln Met Thr Gln Ser Pro Ala Thr Leu Ser Leu Ser Pro Gly
1               5                   10                  15

Glu Arg Ala Thr Leu Ser Cys Arg Ala Ser His Ser Val Ser Ser Asp
            20                  25                  30

Tyr Leu Ala Trp Tyr Gln Lys Pro Gly Arg Ala Pro Arg Leu Leu
        35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Met Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 169
<211> LENGTH: 12
<212> TYPE: PRT
<213> ORGANISM: Artificial Sequence
<220> FEATURE:
<223> OTHER INFORMATION: from human antibody library

<400> SEQUENCE: 169

Arg Ala Ser His Ser Val Ser Ser Asp Tyr Leu Ala
1               5                   10

<210> SEQ ID NO 170
<211> LENGTH: 7
<212> TYPE: PRT
<213> ORGANISM: Artificial Sequence
<220> FEATURE:
<223> OTHER INFORMATION: from human antibody library

<400> SEQUENCE: 170

Gly Ala Ser Ser Arg Ala Thr
1               5

<210> SEQ ID NO 171
<211> LENGTH: 9
<212> TYPE: PRT
<213> ORGANISM: Artificial Sequence
<220> FEATURE:
<223> OTHER INFORMATION: from human antibody library

<400> SEQUENCE: 171

Gln Gln Phe Asp Ser Ser Pro Pro Thr
1               5

<210> SEQ ID NO 172
<211> LENGTH: 109
<212> TYPE: PRT
<213> ORGANISM: Artificial Sequence

```
<220> FEATURE:
<223> OTHER INFORMATION: from human antibody library

<400> SEQUENCE: 172

Asp Ile Gln Met Thr Gln Ser Pro Ala Thr Leu Ser Val Ser Pro Gly
1               5                   10                  15

Glu Arg Ala Thr Leu Ser Cys Arg Ala Ser His Ser Val Ser Ser Asp
            20                  25                  30

Tyr Leu Ala Trp Tyr Gln Gln Lys Pro Gly Arg Ala Pro Arg Leu Leu
        35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Met Tyr Tyr Cys Gln Gln Phe Asp Ser Ser Pro
                85                  90                  95

Pro Thr Phe Gly Gly Gly Thr Lys Val Glu Ile Lys Arg
            100                 105

<210> SEQ ID NO 173
<211> LENGTH: 12
<212> TYPE: PRT
<213> ORGANISM: Artificial Sequence
<220> FEATURE:
<223> OTHER INFORMATION: Human antibody library

<400> SEQUENCE: 173

Arg Ala Ser His Ser Val Ser Ser Asp Tyr Leu Ala
1               5                   10

<210> SEQ ID NO 174
<211> LENGTH: 7
<212> TYPE: PRT
<213> ORGANISM: Artificial Sequence
<220> FEATURE:
<223> OTHER INFORMATION: Human antibody library

<400> SEQUENCE: 174

Gly Ala Ser Ser Arg Ala Thr
1               5

<210> SEQ ID NO 175
<211> LENGTH: 9
<212> TYPE: PRT
<213> ORGANISM: Artificial Sequence
<220> FEATURE:
<223> OTHER INFORMATION: Human antibody library

<400> SEQUENCE: 175

Gln Gln Phe Asp Ser Ser Pro Pro Thr
1               5

<210> SEQ ID NO 176
<211> LENGTH: 109
<212> TYPE: PRT
<213> ORGANISM: Artificial Sequence
<220> FEATURE:
<223> OTHER INFORMATION: Human antibody library

<400> SEQUENCE: 176

Asp Ile Gln Met Thr Gln Ser Pro Gly Thr Leu Ser Leu Ser Pro Gly
1               5                   10                  15

Glu Arg Ala Thr Leu Ser Cys Arg Ala Ser His Ser Val Ser Ser Asp
```

```
                20                  25                  30

Tyr Leu Ala Trp Tyr Gln Gln Lys Pro Gly Arg Ala Pro Arg Leu Leu
            35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Pro Thr Phe Gly Gly Gly Thr Lys Val Glu Ile Lys Arg
                100                 105

<210> SEQ ID NO 177
<211> LENGTH: 12
<212> TYPE: PRT
<213> ORGANISM: Artificial Sequence
<220> FEATURE:
<223> OTHER INFORMATION: Human antibody library

<400> SEQUENCE: 177

Arg Ala Ser His Ser Val Ser Ser Asp Tyr Leu Ala
1               5                   10

<210> SEQ ID NO 178
<211> LENGTH: 7
<212> TYPE: PRT
<213> ORGANISM: Artificial Sequence
<220> FEATURE:
<223> OTHER INFORMATION: Human antibody library

<400> SEQUENCE: 178

Gly Ala Ser Ser Arg Ala Thr
1               5

<210> SEQ ID NO 179
<211> LENGTH: 9
<212> TYPE: PRT
<213> ORGANISM: Artificial Sequence
<220> FEATURE:
<223> OTHER INFORMATION: Human antibody library

<400> SEQUENCE: 179

Gln Gln Phe Asp Ser Ser Pro Pro Thr
1               5

<210> SEQ ID NO 180
<211> LENGTH: 111
<212> TYPE: PRT
<213> ORGANISM: Artificial Sequence
<220> FEATURE:
<223> OTHER INFORMATION: from human Fab library

<400> SEQUENCE: 180

Ile Ala Asp Ile Gln Met Thr Gln Ser Pro Asp Thr Leu Ser Leu Ser
1               5                   10                  15

Pro Gly Glu Arg Ala Thr Leu Ser Cys Arg Ala Ser His Ser Val Ser
            20                  25                  30

Ser Asp Tyr Leu Ala Trp Tyr Gln Gln Lys Pro Gly Ala Pro Arg
            35                  40                  45

Leu Leu Met Tyr Gly Ala Ser Ser Arg Ala Thr Gly Phe Pro Asp Arg
    50                  55                  60

Phe Ser Gly Ser Gly Ser Gly Thr Asp Phe Ser Leu Thr Ile Ser Arg
```

65                  70                  75                  80
Leu Glu Pro Glu Asp Phe Ala Val Tyr Tyr Cys Gln Gln Phe Asp Ser
                        85                  90                  95

Ser Pro Pro Thr Phe Gly Gly Gly Thr Lys Val Glu Ile Lys Arg
            100                 105                 110

<210> SEQ ID NO 181
<211> LENGTH: 12
<212> TYPE: PRT
<213> ORGANISM: Artificial Sequence
<220> FEATURE:
<223> OTHER INFORMATION: from human antibody library

<400> SEQUENCE: 181

Arg Ala Ser His Ser Val Ser Ser Asp Tyr Leu Ala
1               5                   10

<210> SEQ ID NO 182
<211> LENGTH: 7
<212> TYPE: PRT
<213> ORGANISM: Artificial Sequence
<220> FEATURE:
<223> OTHER INFORMATION: from human antibody library

<400> SEQUENCE: 182

Gly Ala Ser Ser Arg Ala Thr
1               5

<210> SEQ ID NO 183
<211> LENGTH: 9
<212> TYPE: PRT
<213> ORGANISM: Artificial Sequence
<220> FEATURE:
<223> OTHER INFORMATION: from human antibody library

<400> SEQUENCE: 183

Gln Gln Phe Asp Ser Ser Pro Pro Thr
1               5

<210> SEQ ID NO 184
<211> LENGTH: 109
<212> TYPE: PRT
<213> ORGANISM: Artificial Sequence
<220> FEATURE:
<223> OTHER INFORMATION: from human antibody library

<400> SEQUENCE: 184

Asp Ile Gln Met Thr Gln Ser Pro Asp Thr Leu Ser Leu Ser Pro Gly
1               5                   10                  15

Glu Arg Ala Thr Leu Ser Cys Arg Ala Ser His Ser Val Ser Ser Asp
            20                  25                  30

Tyr Leu Ala Trp Tyr Gln Gln Lys Pro Gly Arg Ala Pro Arg Leu Leu
        35                  40                  45

Met Tyr Gly Ala Ser Ser Arg Ala Thr Gly Phe Pro Asp Arg Phe Ser
    50                  55                  60

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Phe Asp Ser Ser Pro
                85                  90                  95

Pro Thr Phe Gly Gly Gly Thr Arg Ile Asp Ile Lys Arg
            100                 105

```
<210> SEQ ID NO 185
<211> LENGTH: 10
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (8)..(8)
<223> OTHER INFORMATION: residue is V or I
<220> FEATURE:
<221> NAME/KEY: VARIANT
<222> LOCATION: (10)..(10)
<223> OTHER INFORMATION: residue is G or L

<400> SEQUENCE: 185

Gly Phe Thr Phe Ser Trp Tyr Xaa Met Xaa
1               5                   10

<210> SEQ ID NO 186
<211> LENGTH: 17
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (3)..(3)
<223> OTHER INFORMATION: residue is Y or G
<220> FEATURE:
<221> NAME/KEY: VARIANT
<222> LOCATION: (4)..(4)
<223> OTHER INFORMATION: residue is P or S
<220> FEATURE:
<221> NAME/KEY: VARIANT
<222> LOCATION: (8)..(8)
<223> OTHER INFORMATION: residue is A or F
<220> FEATURE:
<221> NAME/KEY: VARIANT
<222> LOCATION: (10)..(10)
<223> OTHER INFORMATION: residue is N or D

<400> SEQUENCE: 186

Ser Ile Xaa Xaa Ser Gly Gly Xaa Thr Xaa Tyr Ala Asp Ser Val Lys
1               5                   10                  15
Gly

<210> SEQ ID NO 187
<211> LENGTH: 11
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (1)..(1)
<223> OTHER INFORMATION: residue is S Q or T
<220> FEATURE:
<221> NAME/KEY: VARIANT
<222> LOCATION: (3)..(3)
<223> OTHER INFORMATION: residue is D E or Q
<220> FEATURE:
<221> NAME/KEY: VARIANT
<222> LOCATION: (4)..(4)
<223> OTHER INFORMATION: residue is K S N I or A
<220> FEATURE:
<221> NAME/KEY: VARIANT
<222> LOCATION: (6)..(6)
<223> OTHER INFORMATION: residue is G or R
<220> FEATURE:
<221> NAME/KEY: VARIANT
<222> LOCATION: (7)..(7)
<223> OTHER INFORMATION: residue is D S H E or N
<220> FEATURE:
```

```
<221> NAME/KEY: VARIANT
<222> LOCATION: (8)..(8)
<223> OTHER INFORMATION: residue is E Y Q R or N
<220> FEATURE:
<221> NAME/KEY: VARIANT
<222> LOCATION: (9)..(9)
<223> OTHER INFORMATION: residue is Y F or S
<220> FEATURE:
<221> NAME/KEY: VARIANT
<222> LOCATION: (10)..(10)
<223> OTHER INFORMATION: residue is A or S

<400> SEQUENCE: 187

Xaa Gly Xaa Xaa Leu Xaa Xaa Xaa Xaa Ser
1               5                   10

<210> SEQ ID NO 188
<211> LENGTH: 13
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (4)..(4)
<223> OTHER INFORMATION: residue is S or T
<220> FEATURE:
<221> NAME/KEY: VARIANT
<222> LOCATION: (7)..(7)
<223> OTHER INFORMATION: residue is I or L
<220> FEATURE:
<221> NAME/KEY: VARIANT
<222> LOCATION: (8)..(8)
<223> OTHER INFORMATION: residue is E or G
<220> FEATURE:
<221> NAME/KEY: VARIANT
<222> LOCATION: (9)..(9)
<223> OTHER INFORMATION: residue is T S or N
<220> FEATURE:
<221> NAME/KEY: VARIANT
<222> LOCATION: (10)..(10)
<223> OTHER INFORMATION: residue is N or Y
<220> FEATURE:
<221> NAME/KEY: VARIANT
<222> LOCATION: (11)..(11)
<223> OTHER INFORMATION: residue is T P A or Y
<220> FEATURE:
<221> NAME/KEY: VARIANT
<222> LOCATION: (12)..(12)
<223> OTHER INFORMATION: residue is V or L
<220> FEATURE:
<221> NAME/KEY: VARIANT
<222> LOCATION: (13)..(13)
<223> OTHER INFORMATION: residue is N I or Y

<400> SEQUENCE: 188

Ser Gly Ser Xaa Ser Asn Xaa Xaa Xaa Xaa Xaa Xaa Xaa
1               5                   10

<210> SEQ ID NO 189
<211> LENGTH: 14
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (1)..(1)
<223> OTHER INFORMATION: residue is A or T
<220> FEATURE:
<221> NAME/KEY: VARIANT
<222> LOCATION: (3)..(3)
<223> OTHER INFORMATION: residue is S or T
<220> FEATURE:
<221> NAME/KEY: VARIANT
```

```
<222> LOCATION: (5)..(5)
<223> OTHER INFORMATION: residue is H S or N
<220> FEATURE:
<221> NAME/KEY: VARIANT
<222> LOCATION: (7)..(7)
<223> OTHER INFORMATION: residue is I or V
<220> FEATURE:
<221> NAME/KEY: VARIANT
<222> LOCATION: (9)..(9)
<223> OTHER INFORMATION: residue is S or A

<400> SEQUENCE: 189

Xaa Gly Xaa Ser Xaa Asp Xaa Gly Xaa Tyr Asp Tyr Val Ser
 1               5                  10

<210> SEQ ID NO 190
<211> LENGTH: 7
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (1)..(1)
<223> OTHER INFORMATION: residue is Q D T Y S or A
<220> FEATURE:
<221> NAME/KEY: VARIANT
<222> LOCATION: (2)..(2)
<223> OTHER INFORMATION: residue is D N S T or V
<220> FEATURE:
<221> NAME/KEY: VARIANT
<222> LOCATION: (3)..(3)
<223> OTHER INFORMATION: residue is D N S T or Y
<220> FEATURE:
<221> NAME/KEY: VARIANT
<222> LOCATION: (4)..(4)
<223> OTHER INFORMATION: residue is Q K N or L
<220> FEATURE:
<221> NAME/KEY: VARIANT
<222> LOCATION: (5)..(5)
<223> OTHER INFORMATION: residue is R or L

<400> SEQUENCE: 190

Xaa Xaa Xaa Xaa Xaa Pro Ser
 1               5

<210> SEQ ID NO 191
<211> LENGTH: 10
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (2)..(2)
<223> OTHER INFORMATION: residue is A or T
<220> FEATURE:
<221> NAME/KEY: VARIANT
<222> LOCATION: (4)..(4)
<223> OTHER INFORMATION: residue is D or G
<220> FEATURE:
<221> NAME/KEY: VARIANT
<222> LOCATION: (5)..(5)
<223> OTHER INFORMATION: residue is R or no amino acid
<220> FEATURE:
<221> NAME/KEY: VARIANT
<222> LOCATION: (6)..(6)
<223> OTHER INFORMATION: residue is S F or N
<220> FEATURE:
<221> NAME/KEY: VARIANT
<222> LOCATION: (7)..(7)
<223> OTHER INFORMATION: residue is S T or N
<220> FEATURE:
<221> NAME/KEY: VARIANT
<222> LOCATION: (8)..(8)
```

```
<223> OTHER INFORMATION: residue is S T or P
<220> FEATURE:
<221> NAME/KEY: VARIANT
<222> LOCATION: (9)..(9)
<223> OTHER INFORMATION: residue is A V L I or Y
<220> FEATURE:
<221> NAME/KEY: VARIANT
<222> LOCATION: (10)..(10)
<223> OTHER INFORMATION: residue is V or L

<400> SEQUENCE: 191

Gln Xaa Trp Xaa Xaa Xaa Xaa Xaa Xaa Xaa
1               5                   10

<210> SEQ ID NO 192
<211> LENGTH: 11
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (2)..(2)
<223> OTHER INFORMATION: residue is A S or T
<220> FEATURE:
<221> NAME/KEY: VARIANT
<222> LOCATION: (6)..(6)
<223> OTHER INFORMATION: residue is N or S
<220> FEATURE:
<221> NAME/KEY: VARIANT
<222> LOCATION: (8)..(8)
<223> OTHER INFORMATION: residue is N I or G
<220> FEATURE:
<221> NAME/KEY: VARIANT
<222> LOCATION: (9)..(9)
<223> OTHER INFORMATION: residue is G or S
<220> FEATURE:
<221> NAME/KEY: VARIANT
<222> LOCATION: (10)..(10)
<223> OTHER INFORMATION: residue is P W or V
<220> FEATURE:
<221> NAME/KEY: VARIANT
<222> LOCATION: (11)..(11)
<223> OTHER INFORMATION: residue is V or L

<400> SEQUENCE: 192

Ala Xaa Trp Asp Asp Xaa Leu Xaa Xaa Xaa Xaa
1               5                   10

<210> SEQ ID NO 193
<211> LENGTH: 9
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (7)..(7)
<223> OTHER INFORMATION: residue is A or T

<400> SEQUENCE: 193

Met Tyr Ser Thr Ile Thr Xaa Leu Leu
1               5

<210> SEQ ID NO 194
<211> LENGTH: 13
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (4)..(4)
```

```
<223> OTHER INFORMATION: residue is Q E or H
<220> FEATURE:
<221> NAME/KEY: VARIANT
<222> LOCATION: (5)..(5)
<223> OTHER INFORMATION: residue is S R or N
<220> FEATURE:
<221> NAME/KEY: VARIANT
<222> LOCATION: (6)..(6)
<223> OTHER INFORMATION: residue is V I or L
<220> FEATURE:
<221> NAME/KEY: VARIANT
<222> LOCATION: (7)..(7)
<223> OTHER INFORMATION: residue is S R G or N
<220> FEATURE:
<221> NAME/KEY: VARIANT
<222> LOCATION: (8)..(8)
<223> OTHER INFORMATION: residue is S or N
<220> FEATURE:
<221> NAME/KEY: VARIANT
<222> LOCATION: (9)..(9)
<223> OTHER INFORMATION: residue is S N W or D
<220> FEATURE:
<221> NAME/KEY: VARIANT
<222> LOCATION: (10)..(10)
<223> OTHER INFORMATION: residue is G or no amino acid
<220> FEATURE:
<221> NAME/KEY: VARIANT
<222> LOCATION: (12)..(12)
<223> OTHER INFORMATION: residue is L or F
<220> FEATURE:
<221> NAME/KEY: VARIANT
<222> LOCATION: (13)..(13)
<223> OTHER INFORMATION: residue is A G M or S

<400> SEQUENCE: 194

Arg Ala Ser Xaa Xaa Xaa Xaa Xaa Xaa Tyr Xaa Xaa
 1               5                  10

<210> SEQ ID NO 195
<211> LENGTH: 7
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (4)..(4)
<223> OTHER INFORMATION: residue is S T I or N

<400> SEQUENCE: 195

Gly Ala Ser Xaa Arg Ala Thr
 1               5

<210> SEQ ID NO 196
<211> LENGTH: 10
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: (3)..(3)
<223> OTHER INFORMATION: residue is F or Y
<220> FEATURE:
<221> NAME/KEY: VARIANT
<222> LOCATION: (4)..(4)
<223> OTHER INFORMATION: residue is D G or Y
<220> FEATURE:
<221> NAME/KEY: VARIANT
<222> LOCATION: (5)..(5)
<223> OTHER INFORMATION: residue is S T or N
<220> FEATURE:
<221> NAME/KEY: VARIANT
<222> LOCATION: (6)..(6)
<223> OTHER INFORMATION: residue is S L or W
```

```
<220> FEATURE:
<221> NAME/KEY: VARIANT
<222> LOCATION: (7)..(7)
<223> OTHER INFORMATION: residue is P or no amino acid
<220> FEATURE:
<221> NAME/KEY: VARIANT
<222> LOCATION: (8)..(8)
<223> OTHER INFORMATION: residue is P or T
<220> FEATURE:
<221> NAME/KEY: VARIANT
<222> LOCATION: (9)..(9)
<223> OTHER INFORMATION: residue is L I V P W or Y
<220> FEATURE:
<221> NAME/KEY: VARIANT
<222> LOCATION: (10)..(10)
<223> OTHER INFORMATION: residue is T or S

<400> SEQUENCE: 196

Gln Gln Xaa Xaa Xaa Xaa Xaa Xaa Xaa
1               5                   10

<210> SEQ ID NO 197
<211> LENGTH: 7
<212> TYPE: PRT
<213> ORGANISM: Artificial Sequence
<220> FEATURE:
<223> OTHER INFORMATION: Mutation of library member

<400> SEQUENCE: 197

Gly Phe Thr Phe Ser Trp Tyr
1               5

<210> SEQ ID NO 198
<211> LENGTH: 6
<212> TYPE: PRT
<213> ORGANISM: Artificial Sequence
<220> FEATURE:
<223> OTHER INFORMATION: Mutation of library member

<400> SEQUENCE: 198

Tyr Pro Gln Gly Gly Ala
1               5

<210> SEQ ID NO 199
<211> LENGTH: 6
<212> TYPE: PRT
<213> ORGANISM: Artificial Sequence
<220> FEATURE:
<223> OTHER INFORMATION: Mutation of library member

<400> SEQUENCE: 199

Gly Asn Tyr Phe Asp Tyr
1               5

<210> SEQ ID NO 200
<211> LENGTH: 115
<212> TYPE: PRT
<213> ORGANISM: Artificial Sequence
<220> FEATURE:
<223> OTHER INFORMATION: Mutation of library member

<400> SEQUENCE: 200

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Gly Trp Val Arg Gln Ala Pro Gly Lys Gly Leu Glu Trp Val
        35                  40                  45
```

-continued

```
Ser Ser Ile Tyr Pro Gln Gly Ala Thr Ser Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asn Tyr Phe Asp Tyr Trp Gly Gln Gly Thr Leu Val Thr
            100                 105                 110

Val Ser Ser
        115
```

<210> SEQ ID NO 201
<211> LENGTH: 12
<212> TYPE: PRT
<213> ORGANISM: Artificial Sequence
<220> FEATURE:
<223> OTHER INFORMATION: Mutation of library member

<400> SEQUENCE: 201

```
Arg Ala Ser Gln Ser Val Ser Ser Asn Tyr Phe Gly
 1               5                  10
```

<210> SEQ ID NO 202
<211> LENGTH: 7
<212> TYPE: PRT
<213> ORGANISM: Artificial Sequence
<220> FEATURE:
<223> OTHER INFORMATION: Mutation of library member

<400> SEQUENCE: 202

```
Gly Ala Ser Ser Arg Ala Thr
 1               5
```

<210> SEQ ID NO 203
<211> LENGTH: 9
<212> TYPE: PRT
<213> ORGANISM: Artificial Sequence
<220> FEATURE:
<223> OTHER INFORMATION: Mutation of library member

<400> SEQUENCE: 203

```
Gln Gln Phe Asp Ser Leu Pro Leu Thr
 1               5
```

<210> SEQ ID NO 204
<211> LENGTH: 109
<212> TYPE: PRT
<213> ORGANISM: Artificial Sequence
<220> FEATURE:
<223> OTHER INFORMATION: Mutation of library member

<400> SEQUENCE: 204

```
Asp Ile Gln Met Thr Gln Ser Pro Gly Thr Leu Ser Leu Ser Pro Gly
 1               5                  10                  15

Glu Gly Ala Thr Leu Ser Cys Arg Ala Ser Gln Ser Val Ser Ser Asn
                 20                  25                  30

Tyr Phe Gly Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80
```

```
Pro Glu Asp Ser Ala Val Tyr Tyr Cys Gln Gln Phe Asp Ser Leu Pro
                85                  90                  95

Leu Thr Phe Gly Gly Gly Thr Lys Val Glu Ile Lys Arg
            100                 105

<210> SEQ ID NO 205
<211> LENGTH: 7
<212> TYPE: PRT
<213> ORGANISM: Artificial Sequence
<220> FEATURE:
<223> OTHER INFORMATION: Mutation of library member

<400> SEQUENCE: 205

Gly Phe Thr Phe Ser Trp Tyr
1               5

<210> SEQ ID NO 206
<211> LENGTH: 6
<212> TYPE: PRT
<213> ORGANISM: Artificial Sequence
<220> FEATURE:
<223> OTHER INFORMATION: Mutation of library member

<400> SEQUENCE: 206

Tyr Pro Gln Gly Gly Ala
1               5

<210> SEQ ID NO 207
<211> LENGTH: 6
<212> TYPE: PRT
<213> ORGANISM: Artificial Sequence
<220> FEATURE:
<223> OTHER INFORMATION: Mutation of library member

<400> SEQUENCE: 207

Gly Asn Tyr Phe Asp Tyr
1               5

<210> SEQ ID NO 208
<211> LENGTH: 115
<212> TYPE: PRT
<213> ORGANISM: Artificial Sequence
<220> FEATURE:
<223> OTHER INFORMATION: Mutation of library member

<400> SEQUENCE: 208

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Ser Trp Val Arg Gln Ala Pro Gly Lys Gly Leu Glu Trp Val
            35                  40                  45

Ser Ser Ile Tyr Pro Gln Gly Gly Ala Thr Asn Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Tyr Phe Asp Tyr Trp Gly Gln Gly Thr Leu Val Thr
            100                 105                 110

Val Ser Ser
        115
```

```
<210> SEQ ID NO 209
<211> LENGTH: 12
<212> TYPE: PRT
<213> ORGANISM: Artificial Sequence
<220> FEATURE:
<223> OTHER INFORMATION: Mutation of library member

<400> SEQUENCE: 209

Arg Ala Ser Gln Ser Val Ser Ser Asn Tyr Phe Gly
1               5                   10

<210> SEQ ID NO 210
<211> LENGTH: 7
<212> TYPE: PRT
<213> ORGANISM: Artificial Sequence
<220> FEATURE:
<223> OTHER INFORMATION: Mutation of library member

<400> SEQUENCE: 210

Gly Ala Ser Ser Arg Ala Thr
1               5

<210> SEQ ID NO 211
<211> LENGTH: 9
<212> TYPE: PRT
<213> ORGANISM: Artificial Sequence
<220> FEATURE:
<223> OTHER INFORMATION: Mutation of library member

<400> SEQUENCE: 211

Gln Gln His Asp Ser Ser Pro Leu Ser
1               5

<210> SEQ ID NO 212
<211> LENGTH: 109
<212> TYPE: PRT
<213> ORGANISM: Artificial Sequence
<220> FEATURE:
<223> OTHER INFORMATION: Mutated library sequence

<400> SEQUENCE: 212

Asp Ile Gln Met Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Asn
                20                  25                  30

Tyr Phe Gly Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln His Asp Ser Ser Pro
                85                  90                  95

Leu Ser Phe Gly Gly Gly Thr Lys Val Glu Ile Lys Arg
            100                 105

<210> SEQ ID NO 213
<211> LENGTH: 7
<212> TYPE: PRT
<213> ORGANISM: Artificial Sequence
<220> FEATURE:
<223> OTHER INFORMATION: Mutated library sequence
```

<400> SEQUENCE: 213

Gly Phe Thr Phe Ser Trp Tyr
1               5

<210> SEQ ID NO 214
<211> LENGTH: 6
<212> TYPE: PRT
<213> ORGANISM: Artificial Sequence
<220> FEATURE:
<223> OTHER INFORMATION: Mutated library sequence

<400> SEQUENCE: 214

Tyr Pro Ser Gly Gly Ala
1               5

<210> SEQ ID NO 215
<211> LENGTH: 6
<212> TYPE: PRT
<213> ORGANISM: Artificial Sequence
<220> FEATURE:
<223> OTHER INFORMATION: Mutated library sequence

<400> SEQUENCE: 215

Gly Asn Tyr Leu Asp Tyr
1               5

<210> SEQ ID NO 216
<211> LENGTH: 115
<212> TYPE: PRT
<213> ORGANISM: Artificial Sequence
<220> FEATURE:
<223> OTHER INFORMATION: Mutated library sequence

<400> SEQUENCE: 216

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Gly Trp Val Arg Gln Ala Pro Gly Lys Gly Leu Glu Trp Val
        35                  40                  45

Ser Ser Ile Tyr Pro Ser Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Tyr Leu Asp Tyr Trp Gly Gln Gly Thr Leu Val Thr
            100                 105                 110

Val Ser Ser
        115

<210> SEQ ID NO 217
<211> LENGTH: 12
<212> TYPE: PRT
<213> ORGANISM: Artificial Sequence
<220> FEATURE:
<223> OTHER INFORMATION: Mutated library sequence

<400> SEQUENCE: 217

Arg Ala Ser Gln Ser Val Ser Ser Asn Tyr Phe Gly
1               5                   10

```
<210> SEQ ID NO 218
<211> LENGTH: 7
<212> TYPE: PRT
<213> ORGANISM: Artificial Sequence
<220> FEATURE:
<223> OTHER INFORMATION: Mutated library sequence

<400> SEQUENCE: 218

Gly Ala Ser Ser Arg Ala Thr
1               5

<210> SEQ ID NO 219
<211> LENGTH: 9
<212> TYPE: PRT
<213> ORGANISM: Artificial Sequence
<220> FEATURE:
<223> OTHER INFORMATION: Mutated library sequence

<400> SEQUENCE: 219

Gln Gln Phe Asp Ser Ser Pro Leu Ser
1               5

<210> SEQ ID NO 220
<211> LENGTH: 109
<212> TYPE: PRT
<213> ORGANISM: Artificial Sequence
<220> FEATURE:
<223> OTHER INFORMATION: Mutated library sequence

<400> SEQUENCE: 220

Asp Ile Gln Met Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Asn
            20                  25                  30

Tyr Phe Gly Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Phe Asp Ser Ser Pro
                85                  90                  95

Leu Ser Phe Gly Gly Gly Thr Lys Val Glu Ile Lys Arg
            100                 105

<210> SEQ ID NO 221
<211> LENGTH: 7
<212> TYPE: PRT
<213> ORGANISM: Artificial Sequence
<220> FEATURE:
<223> OTHER INFORMATION: Mutated library sequence

<400> SEQUENCE: 221

Gly Phe Thr Phe Ser Trp Tyr
1               5

<210> SEQ ID NO 222
<211> LENGTH: 6
<212> TYPE: PRT
<213> ORGANISM: Artificial Sequence
<220> FEATURE:
<223> OTHER INFORMATION: Mutated library sequence

<400> SEQUENCE: 222
```

Tyr Pro Ser Gly Gly Ala
1               5

<210> SEQ ID NO 223
<211> LENGTH: 6
<212> TYPE: PRT
<213> ORGANISM: Artificial Sequence
<220> FEATURE:
<223> OTHER INFORMATION: Mutated library sequence

<400> SEQUENCE: 223

Gly Pro Tyr Leu Asp Tyr
1               5

<210> SEQ ID NO 224
<211> LENGTH: 115
<212> TYPE: PRT
<213> ORGANISM: Artificial Sequence
<220> FEATURE:
<223> OTHER INFORMATION: Mutated library sequence

<400> SEQUENCE: 224

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Gly Trp Val Arg Gln Ala Pro Gly Lys Gly Leu Glu Trp Val
        35                  40                  45

Ser Ser Ile Tyr Pro Ser Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Tyr Leu Asp Tyr Trp Gly Gln Gly Thr Leu Val Thr
            100                 105                 110

Val Ser Ser
        115

<210> SEQ ID NO 225
<211> LENGTH: 12
<212> TYPE: PRT
<213> ORGANISM: Artificial Sequence
<220> FEATURE:
<223> OTHER INFORMATION: Mutated library sequence

<400> SEQUENCE: 225

Arg Ala Ser Gln Ser Val Ser Ser Asn Tyr Phe Gly
1               5                   10

<210> SEQ ID NO 226
<211> LENGTH: 7
<212> TYPE: PRT
<213> ORGANISM: Artificial Sequence
<220> FEATURE:
<223> OTHER INFORMATION: Mutated library sequence

<400> SEQUENCE: 226

Gly Ala Ser Ser Arg Ala Thr
1               5

<210> SEQ ID NO 227
<211> LENGTH: 9

```
<212> TYPE: PRT
<213> ORGANISM: Artificial Sequence
<220> FEATURE:
<223> OTHER INFORMATION: Mutated library sequence

<400> SEQUENCE: 227

Gln Gln Phe Asp Ser Ser Pro Leu Thr
1               5

<210> SEQ ID NO 228
<211> LENGTH: 109
<212> TYPE: PRT
<213> ORGANISM: Artificial Sequence
<220> FEATURE:
<223> OTHER INFORMATION: Mutated library sequence

<400> SEQUENCE: 228

Asp Ile Gln Met Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Asn
            20                  25                  30

Tyr Phe Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Phe Asp Ser Ser Pro
                85                  90                  95

Leu Thr Phe Gly Gly Gly Thr Lys Val Glu Ile Lys Arg
            100                 105

<210> SEQ ID NO 229
<211> LENGTH: 7
<212> TYPE: PRT
<213> ORGANISM: Artificial Sequence
<220> FEATURE:
<223> OTHER INFORMATION: Mutated library sequence

<400> SEQUENCE: 229

Gly Phe Thr Phe Ser Trp Tyr
1               5

<210> SEQ ID NO 230
<211> LENGTH: 6
<212> TYPE: PRT
<213> ORGANISM: Artificial Sequence
<220> FEATURE:
<223> OTHER INFORMATION: Mutated library sequence

<400> SEQUENCE: 230

Tyr Pro Ser Gly Gly Ala
1               5

<210> SEQ ID NO 231
<211> LENGTH: 6
<212> TYPE: PRT
<213> ORGANISM: Artificial Sequence
<220> FEATURE:
<223> OTHER INFORMATION: Mutated library sequence

<400> SEQUENCE: 231

Gly Ser Tyr Leu Asp Tyr
1               5
```

<210> SEQ ID NO 232
<211> LENGTH: 115
<212> TYPE: PRT
<213> ORGANISM: Artificial Sequence
<220> FEATURE:
<223> OTHER INFORMATION: Mutated library sequence

<400> SEQUENCE: 232

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Gly Trp Val Arg Gln Ala Pro Gly Lys Gly Leu Glu Trp Val
        35                  40                  45

Ser Ser Ile Tyr Pro Ser Gly Gly Ala Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Leu Asp Tyr Trp Gly Gln Gly Thr Leu Val Thr
            100                 105                 110

Val Ser Ser
        115
```

<210> SEQ ID NO 233
<211> LENGTH: 12
<212> TYPE: PRT
<213> ORGANISM: Artificial Sequence
<220> FEATURE:
<223> OTHER INFORMATION: Mutated library sequence

<400> SEQUENCE: 233

```
Arg Ala Ser Gln Ser Val Ser Ser Asn Tyr Phe Gly
1               5                   10
```

<210> SEQ ID NO 234
<211> LENGTH: 7
<212> TYPE: PRT
<213> ORGANISM: Artificial Sequence
<220> FEATURE:
<223> OTHER INFORMATION: Mutated library sequence

<400> SEQUENCE: 234

```
Gly Ala Ser Ser Arg Ala Thr
1               5
```

<210> SEQ ID NO 235
<211> LENGTH: 9
<212> TYPE: PRT
<213> ORGANISM: Artificial Sequence
<220> FEATURE:
<223> OTHER INFORMATION: Mutated library sequence

<400> SEQUENCE: 235

```
Gln Gln Phe Asp Ser Ser Pro Leu Thr
1               5
```

<210> SEQ ID NO 236
<211> LENGTH: 109
<212> TYPE: PRT
<213> ORGANISM: Artificial Sequence
<220> FEATURE:
<223> OTHER INFORMATION: Mutated library sequence

<400> SEQUENCE: 236

```
Asp Ile Gln Met Thr Gln Ser Pro Gly Thr Leu Ser Leu Ser Pro Gly
1               5                   10                  15

Glu Gly Ala Thr Leu Ser Cys Arg Ala Ser Gln Ser Val Ser Ser Asn
            20                  25                  30

Tyr Phe Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Phe Asp Ser Ser Pro
                85                  90                  95

Leu Thr Phe Gly Gly Gly Thr Lys Val Glu Ile Lys Arg
            100                 105
```

RHO KINASE INHIBITORS

CROSS-REFERENCE TO RELATED APPLICATIONS

This application claims priority to U.S. Application No. 61/887,935, filed Oct. 7, 2013, which is incorporated herein by reference in its entirety.

FIELD OF THE INVENTION

The invention relates to inhibitors of ROCK1 and/or ROCK2. Also provided are methods of inhibiting ROCK1 and/or ROCK2 that are useful for the treatment of disease.

BACKGROUND OF THE INVENTION

Rho-associated protein kinase (ROCK) is a key intracellular regulator of cytoskeletal dynamics and cell motility. Rho-kinase regulates a number of downstream targets of RhoA through phosphorylation, including, for example, myosin light chain, the myosin light chain phosphatase binding subunit and LIM-kinase 2. These substrates regulate actin filament organization and contractility. In smooth muscle cells Rho-kinase mediates calcium sensitization and smooth muscle contraction. Inhibition of Rho-kinase blocks 5-HT and phenylephrine agonist induced muscle contraction. When introduced into non-smooth muscle cells, Rho kinase induces stress fiber formation and is required for the cellular transformation mediated by RhoA. Rho kinase participates in a variety of cellular processes, including but not limited to cell adhesion, cell motility and migration, growth control, cell contraction, and cytokinesis. Rho kinase is also involved in Na/H exchange transport system activation, stress fiber formation, adducin activation, and physiological processes such as vasoconstriction, bronchial smooth muscle constriction, vascular smooth muscle and endothelial cell proliferation, platelet aggregation, and others.

Inhibition of Rho-kinase activity in animal models has demonstrated a number of benefits of Rho-kinase inhibition for the treatment of human diseases. These include models of cardiovascular diseases such as hypertension, atherosclerosis, restenosis, cardiac hypertrophy, ocular hypertension, cerebral ischemia, cerebral vasospasm, penile erectile dysfunction, central nervous system disorders such as neuronal degeneration and spinal cord injury, and in neoplasias. Inhibition of Rho-kinase activity has been shown to inhibit tumor cell growth and metastasis, angiogenesis, arterial thrombotic disorders such as platelet aggregation and leukocyte aggregation, asthma, regulation of intraoccular pressure, and bone resorption. The inhibition of Rho-kinase activity in patients has benefits for controlling cerebral vasospasms and ischemia following subarachnoid hemorrhage, reduction of intraocular pressure, increase in ocular aqueous outflow by relaxation of trabecular meshwork tissue, improving blood flow to the optic nerve, and protection of healthy ganglion cells.

In mammals, Rho-kinase consists of two isoforms, ROCK1 (ROCKβ; p160-ROCK) and ROCK2 (ROCKα). ROCK1 and ROCK2 are differentially expressed and regulated in specific tissues. For example, ROCK1 is ubiquitously expressed at relatively high levels, whereas ROCK2 is preferentially expressed in cardiac and brain and skeletal muscle. The isoforms are also expressed in some tissues and in a developmental stage specific manner. ROCK1 is a substrate for cleavage by caspase-3 during apoptosis, whereas ROCK2 is not. Smooth muscle specific basic calponin is phosphorylated only by ROCK2.

Given the extent of involved cellular processes and diseases, compounds that selectively inhibit one rho kinase, or inhibit ROCK1 and ROCK2, are desired.

SUMMARY OF THE INVENTION

The present invention relates to compounds having the formula I:

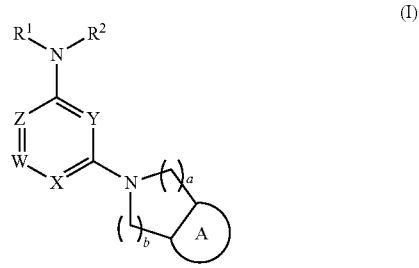

or pharmaceutically acceptable salt thereof, wherein:
$R^1$ is selected from the group consisting of H or $C_1$-$C_6$ alkyl;
$R^2$ is selected from the group consisting of aryl, heteroaryl, $C_3$-$C_7$ cycloalkyl, a three to twelve membered heterocyclic ring containing up to 3 heteroatoms, each of which may be optionally substituted from 1 to 3 substituents independently selected from halo and $C_1$-$C_6$ alkyl;
X is selected from N or $CR^3$;
Y is selected from N or $CR^3$;
Z is selected from N or $CR^4$;
W is selected from $CR^5$;
wherein X, Y, and Z are independently selected and at least one of which is N;
wherein each $R^3$ is independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —$NR^{31}R^{32}$, and —($C_1$-$C_6$ alkyl)-O—($C_1$-$C_6$ alkyl);
$R^{31}$ and $R^{32}$ are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);
$R^4$ and $R^5$ are independently selected from the group consisting of H, halo, $C_1$-$C_8$ alkyl, $C_2$-$C_8$ alkenyl, $C_2$-$C_8$ alkynyl, $C_1$-$C_6$ alkoxy, —($C_1$-$C_6$ alkyl)-O—($C_1$-$C_6$ alkyl), —$NR^{41}R^{42}$, —$(CH_2)_xNR^{41}R^{42}$, and —O—($C_1$-$C_6$ alkyl)-O—($C_1$-$C_6$ alkyl);
$R^{41}$ and $R^{42}$ are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);
or $R^{41}$ and $R^{42}$ may be taken together to form a three to twelve membered cycloalkyl or heterocyclic ring having up to 3 heteroatoms which is optionally substituted from 1 to 3 substituents independently selected from halo, $C_1$-$C_6$ alkyl, and $C_1$-$C_6$ alkoxy;
x is selected from 0 to 6;
or $R^4$ and $R^5$ may be taken together to form a three to twelve membered heterocyclic or aromatic ring having up to 3 heteroatoms which is optionally substituted from 1 to 3 substituents independently selected from halo and $C_1$-$C_6$ alkyl, and $C_1$-$C_6$ alkoxy;
a is selected from 0 to 2;
b is selected from 0 to 2;
wherein a or b are independently selected and one of which is at least 1

A is a three to twelve membered heterocyclic or aromatic ring having up to 3 heteroatoms which is optionally substituted from 1 to 3 substituents independently selected from halo, $C_1$-$C_6$ alkyl, $C_2$-$C_6$ alkenyl, $C_1$-$C_6$ alkoxy, —($C_1$-$C_6$ alkyl)-O—($C_1$-$C_6$ alkyl), $C_3$-$C_7$ cycloalkyl, oxo, acyl, —S—($C_1$-$C_6$ alkyl), OH, $NH_2$, CN, and $C_1$-$C_3$ perfluroalkyl.

The present invention includes pharmaceutical compositions comprising the compounds of the invention and a pharmaceutically acceptable carrier and/or diluents.

The present invention includes compositions comprising a substantially pure compound of the invention and a pharmaceutically acceptable salt, steroisomer, or hydrate thereof, and a pharmaceutically acceptable excipient and/or diluents.

The invention provides a method of inhibiting a rho-kinase in a mammal. The invention provides a method of treating a patient suffering from a disease comprising administering to the patient in need of such treatment a therapeutically effective amount of a compound of Formula I. In certain such embodiments, the compound of Formula I inhibits ROCK2. In certain such embodiments, the compound of Formula I selectively inhibits ROCK2. Non-limiting diseases and conditions treated according to the instant invention include cardiovascular diseases such as hypertension, atherosclerosis, restenosis, cardiac hypertrophy, ocular hypertension, cerebral ischemia, cerebral vasospasm, penile erectile dysfunction, central nervous system disorders such as neuronal degeneration and spinal cord injury, arterial thrombotic disorders such as platelet aggregation and leukocyte aggregation, asthma, regulation of intraocular pressure, and bone resorption. In neoplasias, inhibition of Rho-kinase inhibits tumor cell growth and metastasis, and angiogenesis.

The invention provides a method of treating an autoimmune disorder in a subject comprising administering to the subject a therapeutically effective amount of a compound of Formula I. Autoimmune disorders include, without limitation, rheumatoid arthritis, (multiple sclerosis), systemic lupus erythematosus (SLE; lupus), psoriasis, Crohn's disease, atopic dermatitis, eczema, or graft-versus-host disease (GVHD).

The invention provides a method of treating a cardiovascular disorder in a subject comprising administering to the subject a therapeutically effective amount of a compound of Formula I. Cardiovascular disorders include, without limitation, hypertension, artherosclerosis, restenosis, cardiac hypertrophy, ocular hypertension, cerebral ischemia, cerebral vasospasm, or erectile dysfunction.

The invention provides a method of treating inflammation in a subject comprising administering to the subject a therapeutically effective amount of a compound of Formula I. Inflammation includes, without limitation, asthma, cardiovascular inflammation, renal inflammation or arteriosclerosis.

The invention provides a method of treating a central nervous system disorder in a subject comprising administering to the subject a therapeutically effective amount of a compound of Formula I. Central nervous system disorders include, without limitation, neuronal degeneration or spinal cord injury, as well as Huntington's disease, Parkinson's Disease, Alzheimer's, Amyotrophic lateral sclerosis (ALS), or multiple sclerosis.

The invention provides a method of treating an arterial thrombotic disorder in a subject comprising administering to the subject a therapeutically effective amount of a compound of Formula I. Non-limiting examples of arterial thrombotic disorders are platelet aggregation, or leukocyte aggregation.

The invention provides a method of treating a fibrotic disorder in a subject comprising administering to the subject a therapeutically effective amount of a compound of Formula I. Non-limiting examples of fibrotic disorders are liver fibrosis, lung fibrosis, or kidney fibrosis.

The invention provides a method of maintaining epithelial stability comprising administering to the subject a therapeutically effective amount of a compound of Formula I.

The invention provides a method of treating glaucoma or regulating intraocular pressure in a subject comprising administering to the subject a therapeutically effective amount of a compound of Formula I. Non-limiting examples of glaucoma include primary open-angle glaucoma, acute angle-closure glaucoma, pigmentary glaucoma, neovascular glaucoma, congenital glaucoma, normal tension glaucoma, or secondary glaucoma.

The invention provides a method of treating a neoplastic disease in a subject comprising administering to the subject a therapeutically effective amount of a compound of Formula I. Neoplastic diseases include, without limitation, a lymphoma, carcinoma, leukemia, sarcoma, or blastoma, such as squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, or head and neck cancer.

The invention also provides a method of treating metabolic syndrome, insulin resistance, hyperinsulinemia, type 2 diabetes, or glucose intolerance in a subject comprising administering to the subject a therapeutically effective amount of a compound of Formula I.

Further, the invention provides a method of treating osteoporosis or promoting bone formation a subject comprising administering to the subject a therapeutically effective amount of a compound of Formula I.

The invention also provides a method of treating metabolic syndrome, insulin resistance, hyperinsulinemia, type 2 diabetes, or glucose intolerance in a subject comprising administering to the subject a therapeutically effective amount of a compound of Formula I.

The invention also provides a method of regulating $TH_{17}$ and Treg function, as well as IL-17 and IL-21 production in immune system cells. Accordingly, the invention provides a method of regulating immunological responses using rho kinase inhibitors of Formula I.

The invention provides a method of treating an ocular disorder having an angiogenic component comprising administering to the subject a therapeutically effective amount of a compound of Formula I and an angiogenesis inhibitor. Non-limiting examples of such ocular disorders include age related macular degeneration (AMD), choroidal neovascularization (CNV), diabetic macular edema (DME), iris neovascularization, uveitis, neovascular glaucoma, or retinitis of prematurity (ROP).

Among the angiogenesis inhibitors are VEGR antagonists, including anti-VEGFR2 antibodies. In one embodiment the invention provides an isolated heavy chain variable region comprising a CDR-1H, CDR-2H, and CDR-3H sequence, wherein:

(i) the CDR-1H sequence is GFTFSWYX$_1$MX$_2$ (SEQ ID NO:185), wherein X$_1$ is V or I, X$_2$ is G or L, (ii) the CDR-2H sequence is SIX$_1$X$_2$SGGX$_3$TX$_4$YADSVKG (SEQ ID NO:186), wherein X$_1$ is Y or G, X$_2$ is P or S, X$_3$ is A or F, X$_4$ is N or D, and (iii) the CDR-3H sequence is GNYFDY (SEQ ID NO:3) or GLAAPRS (SEQ ID NO:11).

In one embodiment, the invention provides an isolated light chain variable region comprising a CDR-1L, CDR-2L, and CDR-3L, wherein (i) the CDR-1L sequence is X$_1$GX$_2$X$_3$LX$_4$X$_5$X$_6$X$_7$X$_8$S (SEQ ID NO:187), wherein X$_1$ is S, Q, or T, X$_2$ is D, E, or Q, X$_3$ is K, S, N, I, or A, X$_4$ is G or R, X$_5$ is D, S, H, E, or N, X$_6$ is E, Y, Q, R, or N, X$_7$ is Y, F, or S, and X$_8$ is A or S, or SGSX$_1$SNX$_2$X$_3$X$_4$X$_5$X$_6$X$_7$X$_8$ (SEQ ID NO:188), wherein X$_1$ is S, or T, X$_2$ is I or L, X$_3$ is E or G, X$_4$ is T, S, or N, X$_5$ is N or Y, X$_6$ is T. P, A, or Y, X$_7$ is V or L, and X$_8$ is N, I, or Y, or X$_1$GX$_2$SX$_3$DX$_4$GX$_5$YDYVS (SEQ ID NO:189), wherein X$_1$ is A or T, X$_2$ is S or T, X$_3$ is H, S, or N, X$_4$ is I or V, and X$_5$ is S or A, (ii) the CDR-2L sequence is X$_1$X$_2$X$_3$X$_4$X$_5$PS (SEQ ID NO:190), wherein wherein X$_1$ is Q, D, T, Y, S, or A, X$_2$ is D, N, S, T, V, or V, X$_3$ is D, N, S, T, or Y, X$_4$ is Q, K, N, or L, and X$_5$ is R or L, and (iii) wherein the CDR-3L sequence is QX$_1$WX$_2$X$_3$X$_4$X$_5$X$_6$X$_7$X$_8$ (SEQ ID NO:191), wherein X$_1$ is A or T, X$_2$ is D or G, X$_3$ is R or no amino acid, X$_4$ is S, F, on N, X$_5$ is S, T, on N, X$_6$ is S, T, or P, X$_7$ is A, V, L, I, or Y, and X$_8$ is V or L, or AX$_1$WDDX$_2$LX$_3$X$_4$X$_5$X$_6$ (SEQ ID NO:192), wherein X$_1$ is A, S, or T, X$_2$ is N or S, X$_3$ is N, I, or G, X$_4$ is G or S, X$_5$ is P, W, or V, and X$_6$ is V or L, or MYSTITX$_1$LL (SEQ ID NO:193), wherein X$_1$ is A or T.

In one embodiment, the invention provides an isolated light chain variable region comprising a CDR-1L, CDR-2L, and CDR-3L, wherein (i) the CDR-1L sequence is RASX$_1$X$_2$X$_3$X$_4$X$_5$X$_6$X$_7$YX$_8$X$_9$ (SEQ ID NO:194), wherein X$_1$ is Q, E, or H, X$_2$ is S, R, or N, X$_3$ is V, I, or L, X$_4$ is S, R, G or N, X$_5$ is S or N, X$_6$ is S, N, W, or D, X$_7$ is G or no amino acid, X$_8$ is L or F, and X$_9$ is A, G, M, or S, (ii) the CDR-2L sequence is GASX$_1$RAT (SEQ ID NO:195), wherein X$_1$ is S, T, I, or N, and (iii) the CDR-3L sequence is QQX$_1$X$_2$X$_3$X$_4$X$_5$X$_6$X$_7$X$_8$ (SEQ ID NO:196), wherein X$_1$ is F or Y, X$_2$ is D, G, or Y, X$_3$ is S, T, or N, X$_4$ is S, L, or W, X$_5$ is P or no amino acid, X$_6$ is P or T, X$_7$ is L, I, V, P, W, or Y, and X$_8$ is T or S.

BRIEF DESCRIPTION OF THE FIGURES

FIGS. 4A-C show human heavy chain, lambda light chain, and kappa light chain variable region sequences, respectively, of anti-VEGFR2 antibodies useful in the invention. The boxed regions indicate amino acids residues in complementarity determining regions defined by Kabat and/or Chothia.

FIG. 6A depicts heavy chain amino acid sequences of four affininy matured antibodies derived from Mab 138, which contains the V$_H$ domain having SEQ ID NO:4. FIG. 6B depicts light chain amino acid sequences of the same four affininy matured antibodies derived from SEQ ID NO:160.

FIG. 8A depicts the binding of Mab106 and Mab 147 to human VEGFR2 on HUVEC (Human Umbilical Vein Endothelial Cells) and porcine aortic endothelial (PAE) cells overexpressing KDR (KDR-PAE). FIG. 8B show Mab 147, but not Mab 106, binds to VEGFR2 on MS1 murine endothelial cells. In FIGS. 8A and 8B, the control is an antibody that binds to hVEGFR2 but not mVEGFR2.

DETAILED DESCRIPTION

Figure 1:
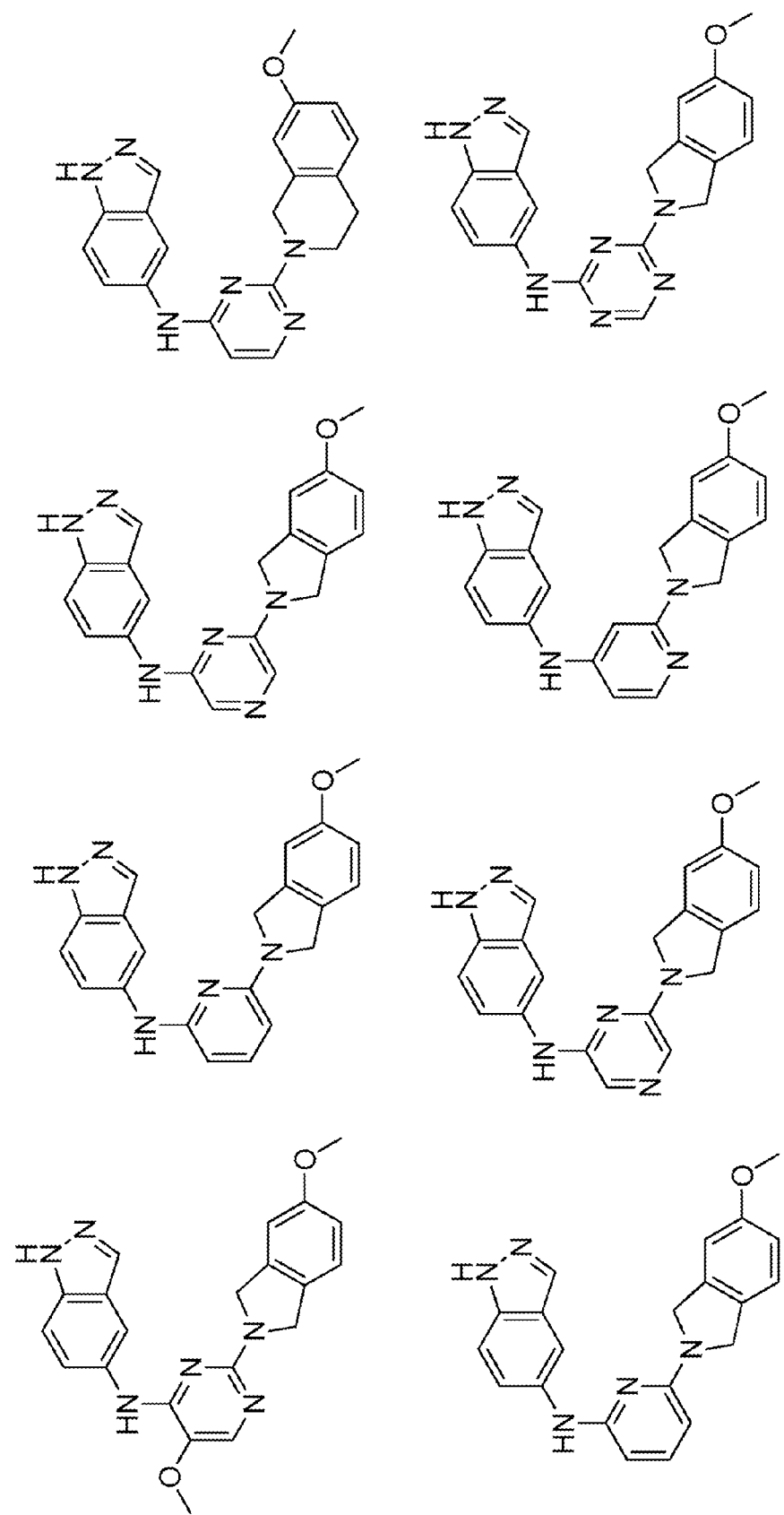
FIG. 1 shows compounds of the invention.
Figure 1:
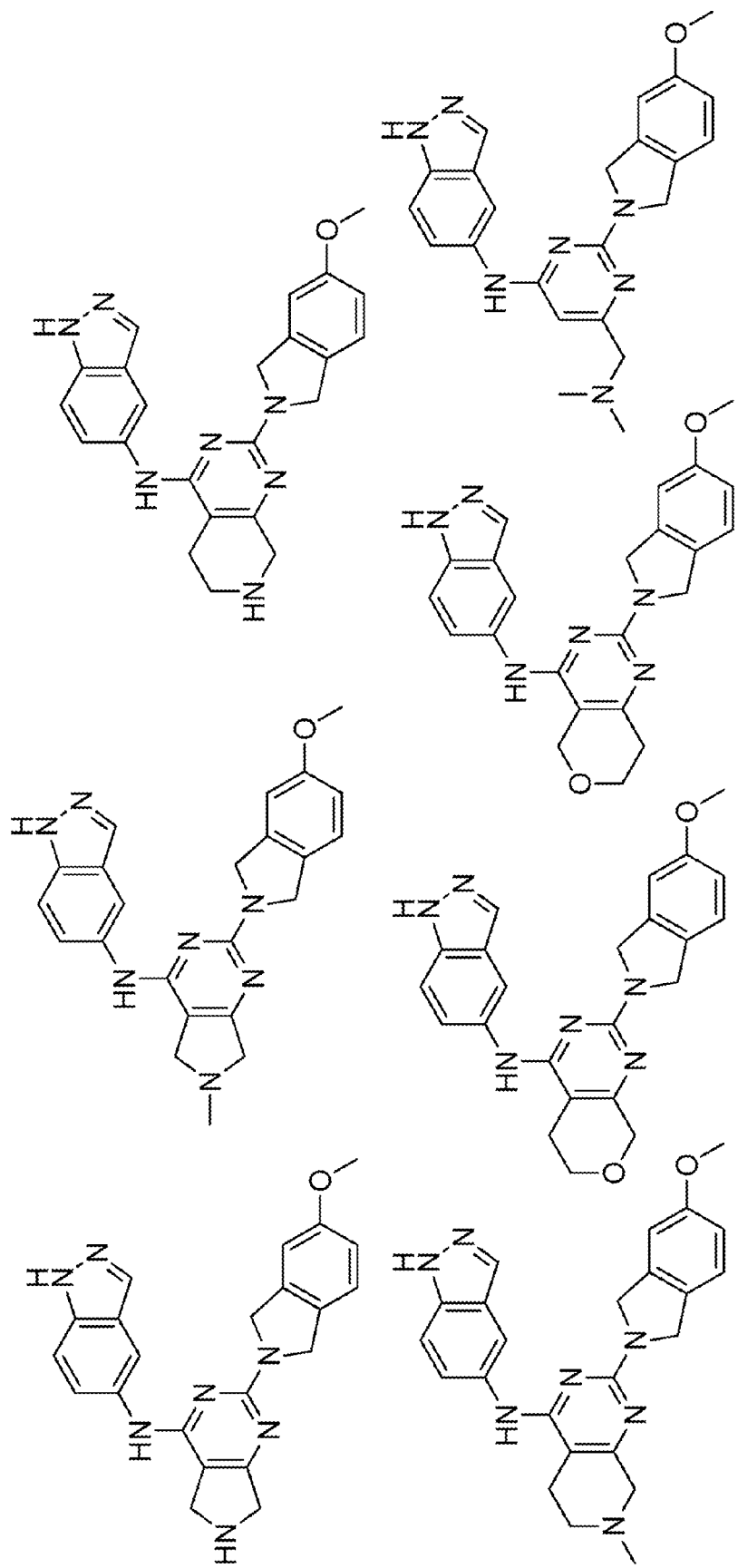
Figure 1:
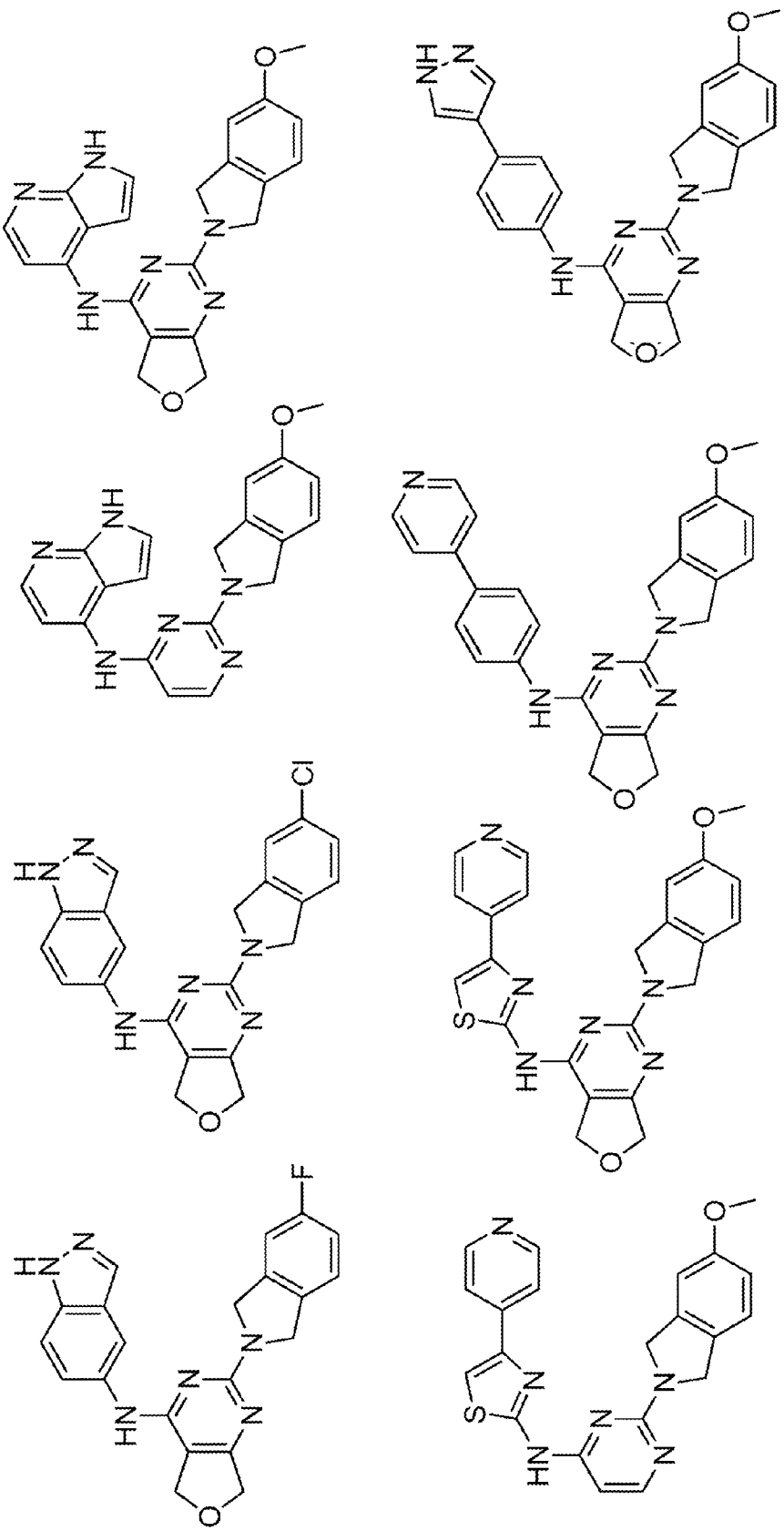
Figure 1:
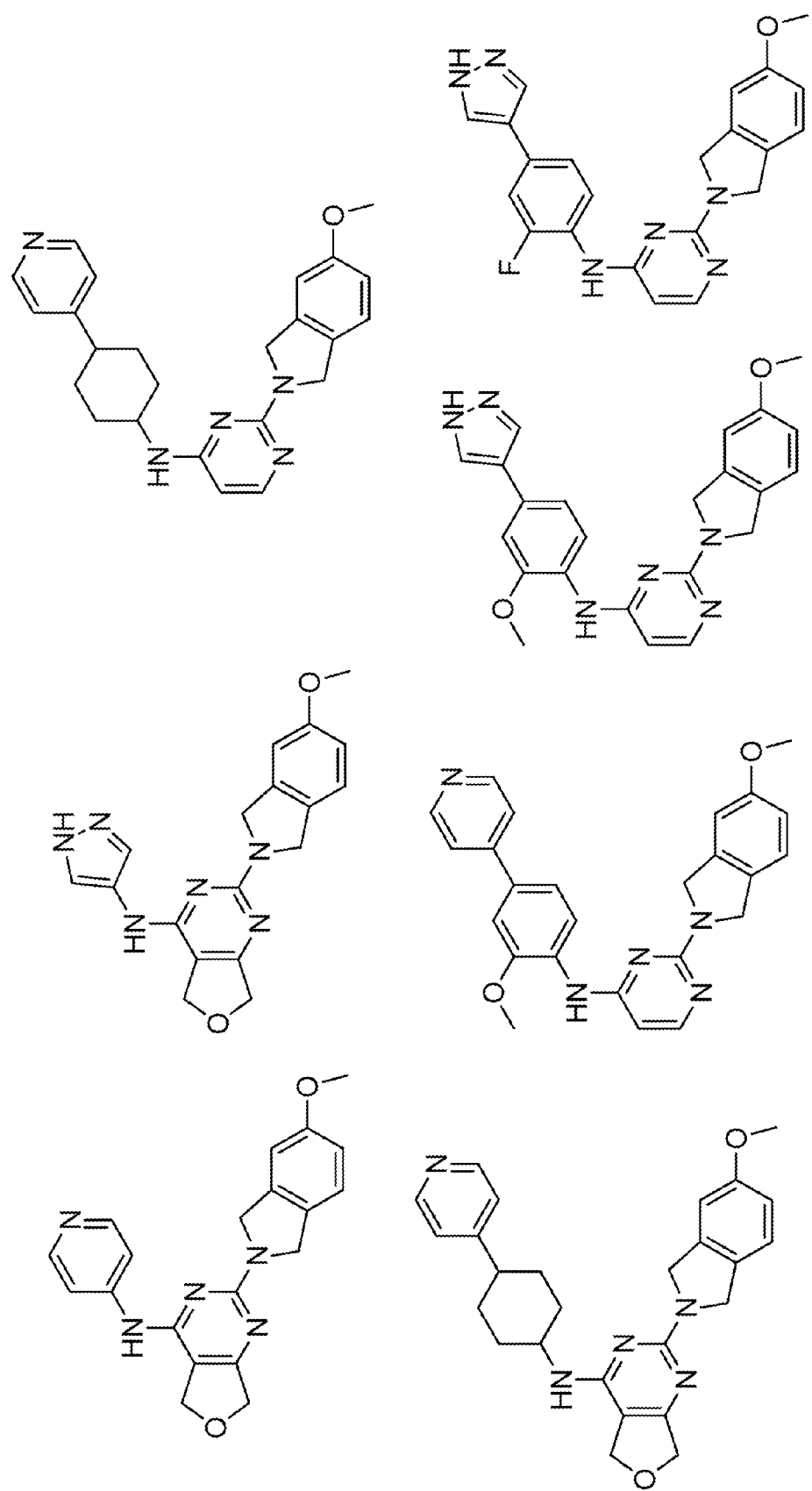

The present invention relates to compounds having the formula I:

(I)

or pharmaceutically acceptable salt thereof, wherein:
$R^1$ is selected from the group consisting of H or $C_1$-$C_6$ alkyl;
$R^2$ is selected from the group consisting of aryl, heteroaryl, $C_3$-$C_7$ cycloalkyl, a three to twelve membered heterocyclic ring containing up to 3 heteroatoms, each of which may be optionally substituted from 1 to 3 substituents independently selected from halo and $C_1$-$C_6$ alkyl;
X is selected from N or $CR^3$;
Y is selected from N or $CR^3$;
Z is selected from N or $CR^4$;
W is selected from $CR^5$;
wherein X, Y, and Z are independently selected and at least one of which is N;
wherein each $R^3$ is independently selected from the group consisting of H, $C_1$-$C_8$ alkyl, $C_2$-$C_8$ alkenyl, $C_2$-$C_8$ alkynyl, —($C_1$-$C_6$ alkyl)-O—($C_1$-$C_6$ alkyl), —$NR^{31}R^{32}$, and —($C_1$-$C_6$ alkyl)-O—($C_1$-$C_6$ alkyl);
$R^{31}$ and $R^{32}$ are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);
$R^4$ and $R^5$ are independently selected from the group consisting of H, halo, $C_1$-$C_8$ alkyl, $C_2$-$C_8$ alkenyl, $C_2$-$C_8$ alkynyl, $C_1$-$C_6$ alkoxy, —($C_1$-$C_6$ alkyl)-O—($C_1$-$C_6$ alkyl), —$NR^{41}R^{42}$, —$(CH_2)_x NR^{41}R^{42}$ and —O—($C_1$-$C_6$ alkyl)-O—($C_1$-$C_6$ alkyl;
$R^{41}$ and $R^{42}$ are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);
or $R^{41}$ and $R^{42}$ may be taken together to form a three to twelve membered cycloalkyl or heterocyclic ring having up to 3 heteroatoms which is optionally substituted from 1 to 3 substituents independently selected from halo, $C_1$-$C_6$ alkyl, and $C_1$-$C_6$ alkoxy;
x is selected from 0 to 6;
or $R^4$ and $R^5$ may be taken together to form a three to twelve membered heterocyclic or aromatic ring having up to 3 heteroatoms which is optionally substituted from 1 to 3 substituents independently selected from halo and $C_1$-$C_6$ alkyl and $C_1$-$C_6$ alkoxy;
a is selected from 0 to 2;
b is selected from 0 to 2;
wherein a or b are independently selected and one of which is at least 1
A is a three to twelve membered heterocyclic or aromatic ring having up to 3 heteroatoms which is optionally substituted from 1 to 3 substituents independently selected from halo, $C_1$-$C_6$ alkyl, $C_2$-$C_6$ alkenyl, $C_1$-$C_6$ alkoxy, —($C_1$-$C_6$ alkyl)-O—($C_1$-$C_6$ alkyl), $C_3$-$C_7$ cycloalkyl, oxo, acyl, —S—($C_1$-$C_6$ alkyl), OH, $NH_2$, CN and $C_1$-$C_3$ perfluroalkyl.

In an embodiment of the invention, $R^1$ is H;
In an embodiment of the invention, $R^2$ is selected from indazole, cyclohexylpyridine, phenylpyridine, phenyl-1H-pyrazole, 1H-pyrrolo[2,3-b]pyridine, 1H-pyrazole, pyridine, isoquinoline, quinoline and 1,3-thiazolyl pyridine;

In an embodiment of the invention, $R^2$ is selected from:

In an embodiment of the invention,
X, Z=N; W=$CR^3$, or
X, Y=N; Z=$CR^4$.
In an embodiment of the invention $R^4$ and $R^5$ are each H;
In another embodiment $R^4$ and $R^5$ are each —$CH_3$;
In still another embodiment $R^4$ and $R^5$ are taken together to form a five-membered ring including, without limitation, dihydrofuran.

In certain embodiments, the invention provides compounds of the formula II:

(II)

wherein $R^2$, $R^4$ and $R^5$ are as defined above;
each $R^6$ is independently selected from the group consisting of halo, $C_1$-$C_6$ alkyl, $C_2$-$C_6$ alkenyl, $C_1$-$C_6$ alkoxy, —($C_1$-$C_6$ alkyl)-O—($C_1$-$C_6$ alkyl), $C_3$-$C_7$ cycloalkyl, oxo, acyl, —S—($C_1$-$C_6$ alkyl), OH, $NH_2$, CN and $C_1$-$C_3$ perfluroalkyl; and
d is selected from 0 to 3.

In certain embodiments, the invention provides compounds of the formula III:

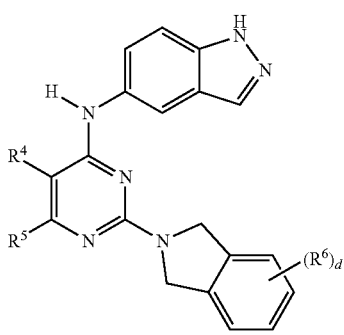

(III)

wherein R[4] and R[5] are as defined above;

each R[6] is independently selected from the group consisting of halo, $C_1$-$C_6$ alkyl, $C_2$-$C_6$ alkenyl, $C_1$-$C_6$ alkoxy, —($C_1$-$C_6$ alkyl)-O—($C_1$-$C_6$ alkyl), $C_3$-$C_7$ cycloalkyl, oxo, acyl, —S—($C_1$-$C_6$ alkyl), OH, NH$_2$, CN and $C_1$-$C_3$ perfluroalkyl; and d is selected from 0 to 3.

The term "heteroatom" as used herein means an atom of any element other than carbon or hydrogen. Preferred heteroatoms are nitrogen, oxygen, and sulfur.

The term "alkyl" refers to the radical of saturated aliphatic groups, including straight-chain alkyl groups and branched-chain alkyl groups. In preferred embodiments, a straight chain or branched chain alkyl has 10 or fewer carbon atoms in its backbone (e.g., $C_1$-$C_{10}$ for straight chain, $C_3$-$C_{10}$ for branched chain) Likewise, preferred cycloalkyls have from 3-10 carbon atoms in their ring structure, and more preferably have 3 to 6 carbons in the ring structure.

Unless the number of carbons is otherwise specified, "lower alkyl" as used herein means an alkyl group, as defined above, but having from one to six carbons, and more preferably from one to four carbon atoms. Likewise, "lower alkenyl" and "lower alkynyl" have similar chain lengths ($C_2$-$C_6$). Preferred alkyl groups are lower alkyls. In preferred embodiments, a substituent designated herein as alkyl is a lower alkyl.

The term "cycloalkyl" refers to saturated, carbocyclic groups having from 3 to 7 carbons in the ring. Preferred cycloalkyl groups include cyclopropyl, cyclobutyl, cyclopentyl and cyclohexyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5- and 6-membered single-ring aromatic groups that may include from zero to four heteroatoms, for example, benzene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles", "heteroaromatics" or "heteroaryl". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, aryls and/or heterocyclic groups.

The terms "heterocyclyl" or "heterocyclic group" refer to 3- to 10-membered ring structures, more preferably 5- or 6-membered rings, whose ring structures include one to four heteroatoms. Heterocycles can also be polycycles. Heterocyclic groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquino line, quinoline, phthalazine, naphthyridine, quinoxaline, quinazoline, cinnoline, pteridine, carbazole, carbo line, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic group can be substituted with such substituents as described above, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

As used herein, the term "nitro" means —NO$_2$. The term "halogen" or "halo" designates —F, —Cl, —Br or —I. The term "hydroxyl" means —OH.

The terms "amine" and "amino" refer to both unsubstituted and substituted amines, e.g., a moiety that can be represented by the general formula:

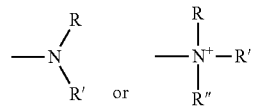

wherein R, R' and R" each independently represent H, alkyl, alkenyl, alkynyl, aralkyl, aryl, and heterocyclic groups, and most preferably H or lower alkyl.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. The term lower alkoxy refers to an alkoxy group having from 1 to 6 carbon atoms.

The term "oxo" as used herein refers to an oxygen atom that has a double bond to a another atom, particularly to carbon or sulfur.

As used herein, the definition of each expression, e.g. alkyl, m, n, R, etc., when it occurs more than once in any structure, is intended to be independent of its definition elsewhere in the same structure.

It will be understood that "substituted", "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds Illustrative substituents include, for example, those described herein above.

Certain compounds of the present invention may exist in particular geometric or stereoisomeric forms. The present invention contemplates all such compounds, including cis- and trans-isomers, R- and S-enantiomers, diastereomers, the racemic mixtures thereof, and other mixtures thereof, as falling within the scope of the invention. Additional asymmetric carbon atoms may be present in a substituent such as an alkyl group. All such isomers, as well as mixtures thereof, are included in this invention.

Certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this context, refers to the relatively non-toxic, inorganic and organic acid addition salts of compounds of the present invention. Representative salts include the hydrochloride, hydrobromide, sulfate, bisulfate, phosphate, nitrate, acetate, stearate, laurate, benzoate, lactate, phosphate, tosylate, citrate, maleate, fumarate, succinate, tartrate, napthylate, and mesylate salts and the like. (See, for example, Berge et al. "Pharmaceutical Salts", *J. Pharm. Sci.* (1977) 66:1-19).

In other cases, the compounds of the present invention may contain one or more acidic functional groups and, thus, are capable of forming pharmaceutically-acceptable salts with pharmaceutically-acceptable bases. Representative salts include alkali or alkaline earth salts such as lithium, sodium, potassium, calcium, magnesium salts and the like. Representative organic amines useful for the formation of base addition salts include ethylamine, diethylamine, ethylenediamine, ethanolamine, diethanolamine, piperazine and the like. (See, for example, Berge et al., supra).

In one aspect, the present invention provides compounds of Formula I that are inhibitors of Rho-kinase. Rho kinase (ROCK), a serine/threonine kinase, serves as a target protein for small GTP-binding protein Rho, and is an important mediator of numerous cellular functions, including focal adhesions, motility, smooth muscle contraction, and cytokinesis. In smooth muscle, ROCK plays an important role in $Ca^{2+}$ sensitization and the control of vascular tone. It modulates the level of phosphorylation of the myosin II light chain of myosin II, mainly through inhibition of myosin phosphatase, and contributes to agonist-induced $Ca^{2+}$ sensitization in smooth muscle contraction.

Rho kinase is found in two forms, ROCK 1 (ROCKβ; p160-ROCK) and ROCK 2 (ROCKα). In some embodiments, the compound of Formula I is selectively inhibits ROCK1. In some embodiments, the compound of Formula I selectively inhibits ROCK2. In some embodiments, the compound of Formula I is non-selective with respect to inhibition of ROCK1 and ROCK2.

Methods of determining kinase inhibition are well known in the art. For example, kinase activity of an enzyme and the inhibitory capacity of a test compound can be determined by measuring enzyme specific phosphorylation of a substrate. Commercial assays and kits can be employed. For example, kinase inhibition can be determined using an IMAP® assay (Molecular Devices). This assay method involves the use of a fluorescently-tagged peptide substrate. Phosphorylation of the tagged peptide by a kinase of interest promotes binding of the peptide to a trivalent metal-based nanoparticle via the specific, high affinity interaction between the phospho-group and the trivalent metal. Proximity to the nanoparticle results in increased fluorescence polarization. Inhibition of the kinase by a kinase inhibitor prevents phosphorylation of the substrate and thereby limits binding of the fluorescently-tagged substrate to the nanoparticle. Such an assay can be compatible with a microwell assay format, allowing simultaneous determination of $IC_{50}$ of multiple compounds.

In another aspect of the present invention there is provided a method of treating a patient suffering from a disease comprising administering to a patient in need of such treatment a therapeutically effective amount of a compound of the present invention. The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment, e.g. reasonable side effects applicable to any medical treatment.

Compounds of the invention that inhibit Rho-kinase and or Rho-kinase mediated phosphorylation are useful for treatment of patients suffering from cardiovascular and non-cardiovascular diseases involving Rho-kinase function, such as hypertension, pulmonary hypertension, atherosclerosis, restenosis, coronary heart disease, cardiac hypertrophy, ocular hypertension, retinopathy, ischemic diseases, cerebral ischemia, cerebral vasospasm, penile erectile dysfunction, peripheral circulatory disorder, peripheral artery occlusive disease, glaucoma, (e.g., regulating intraoccular pressure), fibroid lung, fibroid liver, fibroid kidney, chronic obstructive pulmonary disease (COPD), adult respiratory distress syndrome, central nervous system disorders such as neuronal degeneration and spinal cord injury. Further, Rho-kinase inhibitors of the invention can be used to treat arterial thrombotic disorders such as platelet aggregation and leukocyte aggregation, and bone resorption.

In an embodiment of the invention, compounds are used to treat cerebral cavernous malformation (CCM). CCMs are vascular lesions consisting of clusters of leaky, dilated capillaries and are associated with central nervous system (CNS) disorders, including seizures and stroke. The loss of vascular integrity is thought to involve activation of RhoA and activation of ROCK, leading to changes in cytoskeletal stability and increased vascular permeability. The compounds of the invention inhibit ROCK activation and restore vascular endothelial function.

As indicated, in certain embodiments, a compound of Formula I is used to treat glaucoma. There are several types of glaucoma which can be treated, including, without limitation, the following types. The two most common, primary open-angle glaucoma and acute angle-closure glaucoma are characterized by high ocular pressure. Pigmentary glaucoma and congenital glaucoma also are characterized by reduced fluid outflow and high intraocular pressure (IOP). Normal tension glaucoma, is thought to be due to another mechanism, in particular poor blood flow to the optic nerve. Secondary glaucoma can result from injury, infection, inflammation, tumor or cataracts, and is also associated with prolonged use of steroids, systemic hypertension, diabetic retinopathy, and central retinal vein occlusion.

In certain embodiments, a Rho-kinase inhibitor of the invention is used to treat inflammation, including, but not limited to asthma, cardiovascular inflammation, renal inflammation, atherosclerosis and arteriosclerosis.

The invention provides a method of treating glaucoma which comprises administering to a patient in need thereof; an effective amount of a Rho-kinase inhibitor. In certain embodiments, the Rho-kinase inhibitor is a compound of any one of Formulae I-XXV. The Rho-kinase inhibitor can be non-selective with respect to ROCK1 and ROCK2, or can be a selective ROCK1 inhibitor, or a selective ROCK2 inhibitor. Generally, it is preferred that the inhibitor inhibits ROCK1, i.e., inhibits both ROCK1 and ROCK2 or is selective for ROCK1. In the context of this invention, selective means the inhibitor demonstrates an $IC_{50}$ that is at least 2-fold, at least 5-fold, at least 10-fold, or at least 25-fold lower for one Rho kinase as compared to the $IC_{50}$ for the other Rho kinase. As discussed above, there are several types glaucomas, compounds selective for ROCK1 or ROCK2 can be beneficial for treating certain types. Also, certain glaucomas having a neovascular component can benefit from administration of a angiogenesis inhibitor in addition to a ROCK inhibitor.

Rho-kinase inhibitors of the invention inhibit tumor cell growth and metastasis, and angiogenesis, and are useful for treating neoplastic diseases. Neoplastic diseases include any malignant growth or tumor caused by abnormal or uncontrolled cell division, and may spread to other parts of the body through the lymphatic system or the blood stream. Neoplastic disease includes, without limitation, lymphoma (a neoplasm of lymph tissue that is usually malignant), carcinoma (any malignant tumor derived from epithelial tissue), leukemia (malignant neoplasm of blood-forming tissues; characterized by abnormal proliferation of leukocytes), sarcoma (a usually malignant tumor arising from connective tissue (bone or muscle etc.), and blastoma (malignancy in precursor cells). Nonlimiting examples include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

According to the invention, ROCK inhibitors are used to effect weight loss and/or limit weight gain. In a preferred embodiment, the ROCK inhibitor is ROCK2 selective. ROCK-2 inhibitors promote weight loss in normal subjects, and limit weight gain in subjects prone to obesity.

In an embodiment of the invention, a ROCK inhibitor is used to reduce or prevent insulin resistance or restore insulin sensitivity. Accordingly, in one embodiment, the compounds of the invention are used to promote or restore insulin-dependent glucose uptake. In another embodiment of the invention, a ROCK-inhibitors of the invention is used to promote or restore glucose tolerance. In another embodiment of the invention, a ROCK inhibitor of the invention is used to treat metabolic syndrome. In another embodiment, a ROCK-inhibitors of the invention is used to reduce or prevent hyperinsulinemia. In an embodiment of the invention, a ROCK inhibitor is used to treat diabetes (particularly type 2 diabetes). ROCK inhibitors of the invention may also be used to promote or restore insulin-mediated relaxation of vascular smooth muscle cells (VSMCs). In preferred embodiments, the ROCK inhibitor is ROCK2 selective.

Compounds of formula I demonstrate effective blood brain barrier (BBB) penetration, and tissue distribution to tissues of the central nervous system. Thus, the compounds of the invention are useful for treatment of central nervous system disorders, as well as disorders, such as certain ocular disorders, that benefit from the ability to cross the BBB. Such disorders may involve neuronal degeneration or physical injury to neural tissue, including without limitation, Huntington's disease, Parkinson's Disease, Alzheimer's, Amyotrophic lateral sclerosis (ALS), or multiple sclerosis.

Th17 cells are novel subset of helper $CD4^+$ T cells that secrete IL-17, IL-21 and IL-22. The pro-inflammatory activity of Th17 cells can be beneficial to the host during infection, but uncontrolled Th17 function has been linked and actively involved in several autoimmune pathologies and development of acute and chronic graft-versus-host disease (GVHD), a disease characterized by selective epithelial damage to target organs that is mediated by mature T cells present in the stem cell or bone marrow inoculums. Indeed, high levels of IL-17 are detected in the sera and biopsies of rheumatoid arthritis (RA) and systemic lupus erythematosus (SLE) patients which correlates with destruction of synovial tissue and disease activity. The pathological role of IL-17 in arthritic joints is associated with its stimulation of pro-inflammatory cytokine production and increased recruitment of T cells and innate immune cells. Moreover, numbers of Th17 cells are significantly increased in the peripheral blood of RA patients as well as elevated concentrations of IL-17 were seen in supernatants of their PBMCs after stimulation with anti-CD3/CD28 antibodies ex vivo. In addition, in multiple sclerosis (MS) patients, myelin reactive Th17 cells are also enriched and produce high amounts of IL-22 and IFN-γ. Further, a significantly higher number of $IL-17^+$ cells is detected in disease-affected gut areas compared to healthy areas of the same subjects with Crohn's disease (CD).

The development and function of Th17 cells depends on activation of specific intracellular signaling pathways. The steroid receptor-type nuclear receptor RORγt is selectively expressed in Th17 cells and appears to be required for IL-17 production. The induction of RORγt has been observed to be mediated by IL-6, IL-21 and IL-23 via a STAT3-dependent mechanism. STAT3 also binds directly to the IL-17 and IL-21 promoters. In addition to RORγt and STAT3, the interferon regulatory factor 4 (IRF4) is required for the differentiation of Th17 cells since IRF4 KO mice failed to mount Th17 response and were resistant to development of autoimmune responses. Recent studies have demonstrated that phosphorylation of IRF4 by Rho-kinase 2 (ROCK2) regulates IL-17 and IL-21 production and development of autoimmunity in mice.

According to the invention, targeting Th17 (IL-17-secreting) cells by rho-kinase inhibition provides a method for treating Th17 cell-mediated diseases, including but not limited to autoimmune disorders such as RA, MS, SLE, Psoriasis, and Crohn's disease, and GVHD in humans. In an embodiment of the invention, the Rho-kinase inhibitor is a compound of Formula I. In some embodiments, the rho-kinase inhibitor inhibits ROCK1 and ROCK2. In some embodiments, the rho-kinase inhibitor selectively inhibits ROCK2. Selective inhibition of ROCK2 provides for treatment of Th17 cell-mediated diseases and reduces or prevents toxicities associated with complete inhibition of ROCK activity.

Regulatory T cells (Tregs) play a critical role in the maintenance of immunological tolerance to self-antigens and inhibition of autoimmune responses, but, at the same time, prevent an effective immune response against tumor cells. Indeed, Tregs isolated from the peripheral blood of patients with autoimmune disease, such as rheumatoid arthritis (RA) and multiple sclerosis (MS), show a defect in their ability to suppress effector T cell function, while increased accumulation of Tregs correlates with a poor prognosis in many cancers. Thus, the level of Treg function effects a balance between effective immunity and avoidance of pathological autoreactivity.

The development and function of Tregs depend on activation of specific signaling transduction pathways. TGF-β and IL-2 activate expression of Foxp3 and STAT5 transcription factors that both play an essential role in the control of Treg suppressive function. On the other hand, pro-inflammatory cytokines inhibit Foxp3 expression via up-regulation of STAT3 phosphorylation. According to the invention, pharmacological inhibition of ROCK2 (e.g., with selective ROCK2 inhibitors such as KD025, ROCK2-specific siRNA-mediated inhibition of ROCK2), but not ROCK1, leads to down-regulation of STAT3 phosphorylation, interferon regulatory factor 4 (IRF4) and steroid receptor-type nuclear receptor RORγt protein levels in human T cells. Thus, ROCK2 inhibitors regulate Treg function.

The invention provides methods and compounds for treating diseases and disorders with an angiogenic component. According to the invention, in certain embodiments, such diseases and disorders are treated by administering to a subject an effective amount of a rho kinase inhibitor. In such embodiments, a ROCK2 inhibitor is preferred. In certain embodiments, the inhibitor is a ROCK2 selective inhibitor. According to the invention, such diseases and disorders can also be treated by administering an effective amount of a rho kinase inhibitor that inhibits ROCK2, and may be ROCK2 selective, and an effective amount of an angiogenesis inhibitor. According to the invention, ocular diseases and disorders having an angiogenic component are treated in this manner. In one embodiment, the invention provides a method of treating age related macular degeneration (AMD), which occurs in "dry" and "wet" forms. The "wet" form of AMD causes vision loss due to abnormal blood vessel growth (neovascularization). Bleeding, leaking, and scarring from these retinal blood vessels eventually causes irreversible damage to the photoreceptors. The dry form results from atrophy of the retinal pigment epithelial layer, which causes vision loss through loss of photoreceptors (rods and cones) in the central part of the eye. In another embodiment, the invention provides a method of treating choroidal neovascularization (CNV). Choroidal neovascularization is a process in which new blood vessels grow in the choroid, through the Bruch membrane and invade the subretinal space, and is a symptom of among other causes, age-related macular degeneration, myopia and ocular trauma. In another embodiment, the invention provides a method of treating diabetic macular edema (DME). In another embodiment, the invention provides a method of treating macular edema that is secondary to branch retinal vein occlusion (BRVO) or central retinal vein occlusion (CRVO). In other embodiments, the diseases to be treated include, without limitation, retinal neovascularization, infectious and non-infectious, corneal neovascularization infectious and non-infectious, iris neovascularization, uveitis, neovascular glaucoma, and retinitis of prematurity (ROP). The method of treatment can be prophylactic, such as to stave off corneal neovascularization after corneal transplant, or to modulate the wound healing process in trabeculectomy surgery. These diseases and disorders may be characterized as having an angiogenic component. According to the invention, such disorders are treated by administering a Rho-kinase inhibitor, preferably a ROCK2 selective Rho-kinase inhibitor, and an angiogenesis inhibitor.

Accordingly, in one such embodiment, the disease or disorder is AMD, and a subject in need of treatment for AMD is administered an amount of a ROCK2 inhibitor effective to treat AMD. In another embodiment, the subject is administered a ROCK2 inhibitor and an angiogenesis inhibitor in amounts effective to treat AMD. In such embodiments, a ROCK2-selective inhibitor may be preferred. In some embodiments, the angiogenesis inhibitor is a VEGFR2 antagonist. In certain such embodiments, the VEGFR2 antagonist binds to VEGF. In other such embodiments, the VEGFR2 antagonist binds to VEGFR2. Such VEGFR2-binding inhibitors include agents that bind to the extracellular domain of VEGFR2, including but not limited to antibodies and VEGFR2-binding fragments thereof, and agents that interact with the intracellular domain of VEGFR2 and block activation of VEGFR2-dependent signal transduction. VEGFR2 antagonists further include agents that interact with other cellular components to block VEGFR2-dependent signal transduction. In other embodiments of the invention, other ocular diseases and disorders having an angiogenic component, such as are indicated above, are similarly treated.

According to the invention, a ROCK inhibitor and an angiogenesis inhibitor are administered to a subject in amounts effective amount to treat or preventing a pathologic condition characterized by excessive angiogenesis. Such conditions, involving for example, vascularization and/or inflammation, include atherosclerosis, rheumatoid arthritis (RA), hemangiomas, angiofibromas, and psoriasis. Other non-limiting examples of angiogenic disease are retinopathy of prematurity (retrolental fibroplastic), corneal graft rejection, corneal neovascularization related to complications of refractive surgery, corneal neovascularization related to contact lens complications, corneal neovascularization related to pterygium and recurrent pterygium, corneal ulcer disease, and non-specific ocular surface disease, insulin-dependent diabetes mellitus, multiple sclerosis, myasthenia gravis, Chron's disease, autoimmune nephritis, primary biliary cirrhosis, acute pancreatitis, allograph rejection, allergic inflammation, contact dermatitis and delayed hypersensitivity reactions, inflammatory bowel disease, septic shock, osteoporosis, osteoarthritis, cognition defects induced by neuronal inflammation, Osler-Weber syndrome, restinosis, and fungal, parasitic and viral infections, including cytomegaloviral infections.

The invention provides pan-ROCK inhibitors (i.e., compounds that inhibit ROCK1 and ROCK1) as well as ROCK inhibitors that are isoform selective. As discussed above, in certain embodiments of the invention, a ROCK2-selective inhibitor may be preferred. For example, one study observed that ROCK2 is frequently over expressed in hepatocellular cancer compared to non-timorous livers while ROCK1 expression is unaltered. Other cancers which may benefit from treatment with a ROCK2 selective inhibitor include, but are not limited to, colon and bladder cancer. In contrast, ROCK1 expression levels have been observed to be higher in mammary tumors. Any cancer may be tested to determine whether there is overexpression of ROCK1 and/or ROCK2 and treated accordingly. In certain circumstances, ROCK 1 and ROCK2 isoforms show similarity in regulating certain downstream targets and neither isoform seems to be predominant. In such cases, a pan-ROCK inhibitor may be preferred.

In another aspect, the present invention provides pharmaceutically acceptable compositions which comprise a therapeutically-effective amount of one or more of the compounds of Formula I, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally, or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals with toxicity, irritation, allergic response, or other problems or complications, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluoro hydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

In certain embodiments, a dose of a compound or a composition is administered to a subject every day, every other day, every couple of days, every third day, once a week, twice a week, three times a week, or once every two weeks. If desired, the effective daily dose of the active compound may be administered as two, three, four, five, six or more sub-doses administered separately at appropriate intervals throughout the day, optionally, in unit dosage forms. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more.

The above-described administration schedules are provided for illustrative purposes only and should not be considered limiting. A person of ordinary skill in the art will readily understand that all doses are within the scope of the invention.

While it is possible for a compound of the present invention to be administered alone, it is preferable to administer the compound as a pharmaceutical formulation (composition).

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Ore., U.S.A., 1977).

Microemulsification technology may be employed to improve bioavailability of lipophilic (water insoluble) pharmaceutical agents. Examples include Trimetrine (Dordunoo, S. K., et al., Drug Development and Industrial Pharmacy, 17(12), 1685-1713, 1991) and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). The polymers used in the present invention have a significantly smaller molecular weight, approximately 100 daltons, compared to the large MW of 5000 daltons or greater that used in standard pegylation techniques. Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), caprolactone), polysaccharides, proteins, polyhyaluronic acids, polycyanoacrylates, and blends, mixtures, or copolymers thereof.

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween®. and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

The above-described administration schedules are provided for illustrative purposes only and should not be considered limiting. A person of ordinary skill in the art will readily understand that all doses are within the scope of the invention.

Compounds of the invention can be advantageously administered with second agents to patients in need thereof. When a rho-kinase inhibitor is administered with a second agent, the rho-kinase inhibitor and the second agent can be admnstered sequentially or concomitantly. Sequentially means that one agent is administered for a time followed by administration of the second agent, which may be followed by administration of the first agent. When agents are administered sequentially, the level or one agent may not be maintained at a therapeutically effective level when the second agent is administered, and vice versa. Concomitantly means that the first and second agent are administered according to a schedule that maintains both agents at an substantially therapeutically effective level, even though the agents are not administered simultaneously. Each agent can be administered in single or multiple doses, and the doses can be administered on any schedule, including, without limitation, twice daily, daily, weekly, every two weeks, and monthly.

The invention also includes adjunctive administration. Adjunctive administration means that a second agent is administered to a patient in addition to a first agent that is already being administered to treat a disease or disease symptom. In some embodiments, adjunctive administration involves administering a second agent to a patient in which administration of the first agent did not sufficiently treat a disease or disease symptom. In other embodiments, adjunctive administration involves administration of the second agent to a patient whose disease has been effectively treated by administration of the first agent, with the expectation that the adjunctive treatment improves the outcome of the treatment. In some embodiments, the effect of administering the first and second agents is synergistic. In some embodiments, administration of the first and second agents prevents or lengthens the time until relapse, compared to administration of either of the agents alone. In some embodiments, administration of the first and second agents allows for reduced dosage and/or frequency of administration of the first and second agent.

In an embodiment of the invention, a rho-kinase inhibitor of the invention and an anti-neoplastic agent are administered to a subject in need thereof. In another embodiment, a rho-kinase inhibitor of the invention and an angiogenesis inhibitor are administered to a subject in need thereof. In another embodiment, a rho-kinase inhibitor of the invention and an anti-inflammatory agent are administered to a subject in need thereof. In yet another embodiment, a rho-kinase inhibitor of the invention and an immunosuppressant are administered. The second agent can be, without limitation, a small molecule, an antibody or antigen binding fragment thereof, or radiation.

Antineoplastic agents include, without limitation, cytotoxic chemotherapeutic agents, targeted small molecules and biological molecules, and radiation. Compounds and agents that can be administered for oncological treatment, in addition to a rho kinase inhibitor of the invention, include the following: irinotecan, etoposide, camptothecin, 5-fluorouracil, hydroxyurea, tamoxifen, paclitaxel, capcitabine, carboplatin, cisplatin, bleomycin, dactomycin, gemcitabine, doxorubicin, danorubicin, cyclophosphamide, and radiotherapy, which can be external (e.g., external beam radiation therapy (EBRT)) or internal (e.g., brachytherapy (BT)).

Targeted small molecules and biological molecules include, without limitation, inhibitors of components of signal transduction pathways, such as modulators of tyrosine kinases and inhibitors of receptor tyrosine kinases, and agents that bind to tumor-specific antigens. Examples include inhibitors of epidermal growth factor receptor (EGFR), including gefitinib, erlotinib, and cetuximab, inhibitors of HER2 (e.g., trastuzumab, trastuzumab emtansine (trastuzumab-DM1; T-DM1) and pertuzumab), anti-VEGF antibodies and fragments (e.g., bevacizumab), antibodies that inhibit CD20 (e.g., rituximab, ibritumomab), anti-VEGFR antibodies (e.g., ramucirumab (IMC-1121B), IMC-1C11, and CDP791), anti-PDGFR antibodies, and imatinib. Small molecule kinase inhibitors can be specific for a particular tyrosine kinase or be inhibitors of two or more kinases. For example, the compound N-(3,4-dichloro-2-fluorophenyl)-7-({[(3aR,6aS)-2-methyloctahydrocyclopenta[c] pyrrol-5-yl]methyl}oxy)-6-(methyloxy)quinazolin-4-amine (also known as XL647, EXEL-7647 and KD-019) is an in vitro inhibitor of several receptor tyrosine kinases (RTKs), including EGFR, EphB4, KDR (VEGFR), Flt4 (VEGFR3) and ErbB2, and is also an inhibitor of the SRC kinase, which is involved in pathways that result in nonresponsiveness of tumors to certain TKIs. In an embodiment of the invention, treatment of a subject in need comprises administration of a rho-kinase inhibitor of Formula I and administration of KD-019.

Dasatinib (BMS-354825; Bristol-Myers Squibb, New York) is another orally bioavailable, ATP-site competitive Src inhibitor. Dasatanib also targets Bcr-Abl (FDA-approved for use in patients with chronic myelogenous leukemia (CML) or Philadelphia chromosome positive (Ph+) acute lymphoblastic leukemia (ALL)) as well as c-Kit, PDGFR, c-FMS, EphA2, and Src family kinases. Two other oral tyrosine kinase inhibitor of Src and Bcr-Abl are bosutinib (SKI-606) and saracatinib (AZD0530).

Figure 10A:
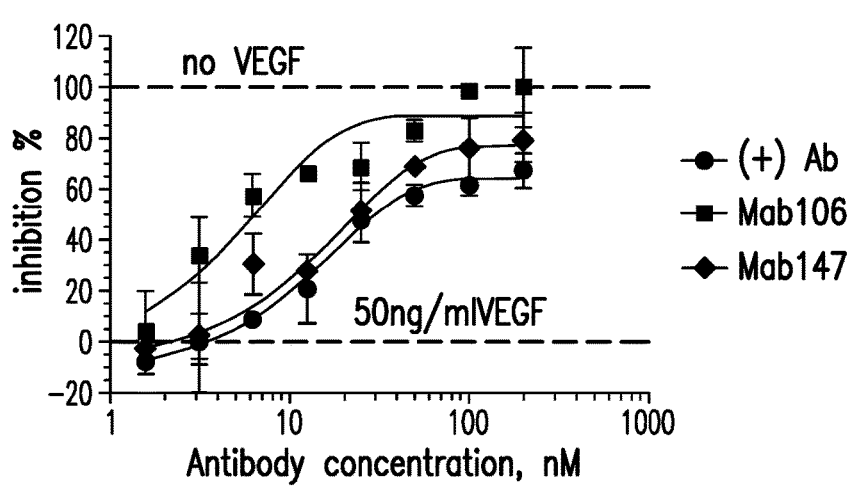
FIG. 10A depicts inhibition of proliferation of KDR-PAE cells by Mab 106, Mab 147, and a control antibody that binds to hVEGFR2.

According to the invention, angiogenesis inhibitors can be administered to a subject in conjunction with compounds of the invention. Angiogenesis inhibitors include any substance that inhibits the growth of new blood vessels. For example, angiogenesis inhibitors include antagonists of VEGF, PlGF, and VEGF receptors, including the antibodies disclosed herein. By inhibitor is meant an inhibitor of a biological process or inhibitor of a target. In this regard, an angiogenesis inhibitor is an agent that reduces angiogenesis. A Rho-kinase inhibitor is an agent, such as a competitive inhibitor of ATP binding, that inhibits an intrinsic activity or blocks an interaction of Rho-kinase. By antagonist is meant a substance that reduces or inhibits an activity or function in a cell associated with a target. For example, a VEGF antagonist reduces or blocks a function in a cell that is associated with VEGF. A VEGF antagonist may act on VEGF, by binding to VEGF and blocking binding to its receptors and/or may act on another cellular component involved in VEGF-mediated signal transduction. Similarly, a VEGFR2 antagonist is an agent that reduces or blocks VEGFR2-mediated signal transduction by binding to VEGFR2 and blocking ligand binding or interaction with a VEGFR2 substrate, or acts on another cellular component to reduce or block VEGFR2-mediated signal transduction. Thus, angiogenesis inhibitors include anti-VEGFR2 antibodies set forth herein (Table 1, Table 2, FIG. 10), and antagonists of without limitation, VEGF, VEGFR1, VEGFR2, PDGF, PDGFR-β, neuropilin-1 (NRP1), and complement.

The invention provides anti-VEGFR2 antibodies, including nucleic acids encoding such antibodies and compositions comprising such antibodies. In one embodiment the invention provides an isolated antibody heavy chain variable region comprising a CDR-1H, CDR-2H, and CDR-3H sequence, wherein:

(i) the CDR-1H sequence is GFTFSWYX$_1$MX$_2$ (SEQ ID NO:185), wherein X$_1$ is V or I, X$_2$ is G or L, (ii) the CDR-2H sequence is SIX$_1$X$_2$SGGX$_3$TX$_4$YADSVKG (SEQ ID NO:186), wherein X$_1$ is Y or G, X$_2$ is P or S, X$_3$ is A or F, X$_4$ is N or D, and (iii) the CDR-3H sequence is GNYFDY (SEQ ID NO:3) or GLAAPRS (SEQ ID NO:11).

In one embodiment, the invention provides an isolated light chain variable region comprising a CDR-L1, CDR-L2, and CDR-L3, wherein (i) the CDR-L1 sequence is X$_1$GX$_2$X$_3$LX$_4$X$_5$X$_6$X$_7$X$_8$S (SEQ ID NO:187), wherein X$_1$ is S, Q, or T, X$_2$ is D, E, or Q, X$_3$ is K, S, N, I, or A, X$_4$ is G or R, X$_5$ is D, S, H, E, or N, X$_6$ is E, Y, Q, R, or N, X$_7$ is Y, F, or S, and X$_8$ is A or S, or SGSX$_1$SNX$_2$X$_3$X$_4$X$_5$X$_6$X$_7$X$_8$ (SEQ ID NO:188), wherein X$_1$ is S, or T, X$_2$ is I or L, X$_3$ is E or G, X$_4$ is T, S, or N, X$_5$ is N or Y, X$_6$ is T, P, A, or Y, X$_7$ is V or L, and X$_8$ is N, I, or Y, or X$_1$GX$_2$SX$_3$DX$_4$GX$_5$YDYVS (SEQ ID NO:189), wherein X$_1$ is A or T, X$_2$ is S or T, X$_3$ is H, S, or N, X$_4$ is I or V, and X$_5$ is S or A, (ii) the CDR-L2 sequence is X$_1$X$_2$X$_3$X$_4$X$_5$PS (SEQ ID NO:190), wherein wherein X$_1$ is Q, D, T, Y, S, or A, X$_2$ is D, N, S, T, or V, X$_3$ is D, N, S, T, or Y, X$_4$ is Q, K, N, or L, and X$_5$ is R or L, and (iii) wherein the CDR-L3 sequence is QX$_1$WX$_2$X$_3$X$_4$X$_5$X$_6$X$_7$X$_8$(SEQ ID NO:191), wherein X$_1$ is A or T, X$_2$ is D or G, X$_3$ is R or no amino acid, X$_4$ is S, F, or N, X$_5$ is S, T, or N, X$_6$ is S, T, or P, X$_7$ is A, V, L, I, or Y, and X$_8$ is V or L, or AX$_1$WDDX$_2$LX$_3$X$_4$X$_5$X$_6$ (SEQ ID NO:192, wherein X$_1$ is A, S, or T, X$_2$ is N or S, X$_3$ is N, I, or G, X$_4$ is G or S, X$_5$ is P, W, or V, and X$_6$ is V or L, or MYSTITX$_1$LL (SEQ ID NO:193), wherein X$_1$ is A or T.

In one embodiment, the invention provides an isolated light chain variable region comprising a CDR-L1, CDR-L2, and CDR-L3, wherein (i) the CDR-L1 sequence is RASX$_1$X$_2$X$_3$X$_4$X$_5$X$_6$X$_7$YX$_8$X$_9$ (SEQ ID NO:194), wherein $X_1$ is Q, E, or H, $X_2$ is S, R, or N, $X_3$ is V, I, or L, $X_4$ is S, R, G or N, $X_5$ is S or N, $X_6$ is S, N, W, or D, $X_7$ is G or no amino acid, $X_8$ is L or F, and $X_9$ is A, G, M, or S, (ii) the CDR-L2 sequence is $GASX_1RAT$ (SEQ ID NO:195), wherein $X_1$ is S, T, I, or N, and (iii) the CDR-L3 sequence is $QQX_1X_2X_3X_4X_5X_6X_7X_8$ (SEQ ID NO:196), wherein $X_1$ is F or Y, $X_2$ is D, G, or Y, $X_3$ is S, T, or N, $X_4$ is S, L, or W, $X_5$ is P or no amino acid, $X_6$ is P or T, $X_7$ is L, I, V, P, W, or Y, and $X_8$ is T or S.

In an embodiment of the invention, an antibody is provided which comprises a heavy chain variable domain comprising one, two, three, four, five, or six of the light chain variable domain and heavy chain variable domain CDR sequences set forth above.

Non-limiting examples of VEGFR2-binding antibody sequences are provided. As described herein, from human Fab phage display libraries, two neutralizing antibodies were identified that bind to human VEGFR2, block binding of the ligand VEGFA to hVEGFR2, and inhibit the VEGFR2 phosphorylation and downstream signal transduction stimulated by VEGFA. Table 1 indicates amino acid sequences of the CDRs and variable domains of antibodies of the antibodies. The $K_d$s of Mab 101 and Mab 102 are about 6.6 mM and 1.7 nM, respectively.

TABLE 1

Antibody Amino Acid Sequences by SEQ ID NO

| Mab | CDR-H1 | CDR-H2 | CDR-H3 | $V_H$ domain | CDR-L1 | CDR-L2 | CDR-L3 | $V_L$ domain |
|---|---|---|---|---|---|---|---|---|
| 101 | 1 | 2 | 3 | 4 | 5 | 6 | 7 | 8 |
| 102 | 9 | 10 | 11 | 12 | 13 | 14 | 15 | 16 |

The heavy chain of Mab 101 was reshuffled with κ light chain genes (κ-library) and λ light chain genes (λ-library). 20 unique λ light chain variants were found by panning the λ-library against both human VEGFR2 and mouse VEGFR2. 22 unique κ light chain variants were found by panning the κ-library against both human VEGFR2 and mouse VEGFR2. Table 2 indicates amino acid sequences of the CDRs and variable domains of the light chains. The KDs of Mabs 105, 106, and 107 were increased about 10 fold (0.24 nM, 0.22 nM, and 0.12 nM, respectively).

TABLE 2

κ and λ light chains by SEQ ID NO

| Mab | light chain | CDR-L1 | CDR-L2 | CDR-L3 | $V_L$ |
|---|---|---|---|---|---|
| 103 | λ | 17 | 18 | 19 | 20 |
| 104 | λ | 21 | 22 | 23 | 24 |
| 105 | λ | 25 | 26 | 27 | 28 |
| 106 | λ | 29 | 30 | 31 | 32 |
| 107 | λ | 33 | 34 | 35 | 36 |
| 108 | λ | 37 | 38 | 39 | 40 |
| 109 | λ | 41 | 42 | 43 | 44 |
| 110 | λ | 45 | 46 | 47 | 48 |
| 111 | λ | 49 | 50 | 51 | 52 |
| 112 | λ | 53 | 54 | 55 | 56 |
| 113 | λ | 57 | 58 | 59 | 60 |
| 114 | λ | 61 | 62 | 63 | 64 |
| 115 | λ | 65 | 66 | 67 | 68 |
| 116 | λ | 69 | 70 | 71 | 72 |
| 117 | λ | 73 | 74 | 75 | 76 |
| 118 | λ | 77 | 78 | 79 | 80 |
| 119 | λ | 81 | 82 | 83 | 84 |
| 120 | λ | 85 | 86 | 87 | 88 |
| 121 | λ | 89 | 90 | 91 | 92 |
| 122 | λ | 93 | 94 | 95 | 96 |
| 123 | κ | 97 | 98 | 99 | 100 |
| 124 | κ | 101 | 102 | 103 | 104 |
| 125 | κ | 105 | 106 | 107 | 108 |
| 126 | κ | 109 | 110 | 111 | 112 |
| 127 | κ | 113 | 114 | 115 | 116 |
| 128 | κ | 117 | 118 | 119 | 120 |
| 129 | κ | 121 | 122 | 123 | 124 |
| 130 | κ | 125 | 126 | 127 | 128 |
| 131 | κ | 129 | 130 | 131 | 132 |
| 132 | κ | 133 | 134 | 135 | 136 |
| 133 | κ | 137 | 138 | 139 | 140 |
| 134 | κ | 141 | 142 | 143 | 144 |
| 135 | κ | 145 | 146 | 147 | 148 |
| 136 | κ | 149 | 150 | 151 | 152 |
| 137 | κ | 153 | 154 | 155 | 156 |
| 138 | κ | 157 | 158 | 159 | 160 |
| 139 | κ | 161 | 162 | 163 | 164 |
| 140 | κ | 165 | 166 | 167 | 168 |
| 141 | κ | 169 | 170 | 171 | 172 |
| 142 | κ | 173 | 174 | 175 | 176 |
| 143 | κ | 177 | 178 | 179 | 180 |
| 144 | κ | 181 | 182 | 183 | 184 |

The invention provides an isolated VEGFR2 antibody, and VEGFR2 binding fragments thereof, which comprises one, two, or three heavy chain CDRs and one, two, or three light chain CDRs, selected from the sequences set forth in Table 1 and Table 2. In an antibody of the invention, when more than one CDR is selected from the sequences presented in Table 1 and Table 2, the different CDRs need not be selected from the same monoclonal antibody presented in those tables, but can be selected from two or more antibody variable domains presented in the tables. Specific embodiments include, but are not limited to, the following. In an embodiment of the invention, the isolated VEGFR2 antibody comprises one, two, or three heavy chain CDRs having SEQ ID NO:1, SEQ ID NO:2, and SEQ ID NO:3. In an embodiment, of the invention, the antibody comprises one, two, or three light chain CDRs having SEQ ID NO:5, SEQ ID NO:6, and SEQ ID NO:7. In another embodiment, the antibody comprises one, two, or three light chain CDRs having sequences as set forth in Table 1 or 2. Non-limiting examples include a light chain variable region comprising one or more of SEQ ID NO:25, SEQ ID NO:26, and SEQ ID NO:27, one or more of SEQ ID NO:29, SEQ ID NO:30, and SEQ ID NO:31, or one or more of SEQ ID NO:33, SEQ ID NO:34, and SEQ ID NO:35. In certain embodiments, the VEGFR2 antibody comprises a heavy chain variable domain comprising SEQ ID NO:4 or SEQ ID NO:12. In certain embodiments, the VEGFR2 antibody comprises a light chain variable domain comprising SEQ ID NO:8, SEQ ID NO:16, SEQ ID NO:27, SEQ ID NO:31, or SEQ ID NO:35. In certain embodiments, the antibodies comprise one of the above-mentioned heavy chain variable domains and one of the above-mentioned light chain variable domains. In certain embodiments, the VEGFR2 antibodies or binding fragments thereof comprise one or more CDRs or one or more variable domains with an amino acid sequence at least 85% at least 90%, at least 95%, at least 97%, at least 98%, or at least 99%, identical to the CDR and variable domain sequences set forth in Table 1, 2 or 3. In certain embodiments, antibodies of the invention have CDR amino acids identical to those disclosed herein and frameworks that are at least least 85%, at least 90%, of at least 95% identical.

"Identity" refers to the number or percentage of identical positions shared by two amino acid or nucleic acid sequences, taking into account the number of gaps, and the length of each gap, which need to be introduced for optimal alignment of the two sequences. "Substantially identical" means an amino acid sequence that which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein. Preferably, the amino acid sequence is at least 80%, more preferably at least 85%, and most preferably at least 90% similar to another amino acid sequence. Methods and computer programs for determining sequence similarity are publically available, including, but not limited to, the GCG program package (Devereux et al., Nucleic Acids Research 12: 387, 1984), BLASTP, BLASTN, FASTA (Altschul et al., J. Mol. Biol. 215:403 (1990), and the ALIGN program (version 2.0). The well-known Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0 at http://www.ncbi.nlm.nih.gov/blast/). In comparing sequences, these methods account for various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Certain embodiments of the invention involve the use of VEGFR2-binding antibody fragments. An Fv is the smallest fragment that contains a complete heavy and light chain variable domain, including all six hypervariable loops (CDRs). Lacking constant domains, the variable domains are noncovalently associated. The heavy and light chains may be connected into a single polypeptide chain (a "single-chain Fv" or "scFv") using a linker that allows the $V_H$ and $V_L$ domains to associate to form an antigen binding site. In an embodiment of the invention, the linker is (Gly-Gly-Gly-Gly-Ser)$_3$. Since scFv fragments lack the constant domains of whole antibodies, they are considerably smaller than whole antibodies. scFv fragments are also free of normal heavy-chain constant domain interactions with other biological molecules which may be undesired in certain embodiments.

Fragments of an antibody containing $V_H$, $V_L$, and optionally $C_L$, $C_H1$, or other constant domains can also be used. Monovalent fragments of antibodies generated by papain digestion are referred to as Fab and lack the heavy chain hinge region. Fragments generated by pepsin digestion, referred to as F(ab')$_2$, retain the heavy chain hinge and are divalent. Such fragments may also be recombinantly produced. Many other useful antigen-binding antibody fragments are known in the art, and include, without limitation, diabodies, triabodies, single domain antibodies, and other monovalent and multivalent forms.

The invention further provides multivalent antigen-binding proteins, which can be in the form, without limitation, of antibodies, antigen-binding fragments thereof, and proteins comprising all or part of antigen-binding portions of antibodies. Multivalent antigen-binding proteins may be monospecific, bispecific, or multispecific. The term specificity refers to the number of different types of antigenic determinants to which a particular molecule can bind. If an immunoglobulin molecule binds to only one type of antigenic determinant, the immunoglobulin molecule is monospecific. If the immunoglobulin molecule binds to different types of antigenic determinants then the immunoglobulin molecule is multispecific.

For example, a bispecific multivalent single chain antibody allows for the recognition of two different types of epitopes. Both epitopes may be on the same antigen (e.g., VEGFR2). Alternatively, one epitope may be on one antigen (e.g., VEGFR2), and the second epitope on a different antigen.

In one embodiment, a multivalent single chain antibody includes a variable light-chain fragment linked to a variable heavy-chain fragment (similar to an scFv), which is further linked by another peptide linker to at least one other antigen binding domain. Typically, the peptide linker is composed of about fifteen amino acid residues. In a preferred embodiment, the number of $V_L$ and $V_H$ domains is equivalent. For example, a bivalent single chain antibody can be represented as follows: $V_L$-$L_1$-$V_H$$L_2$-$V_L$-$L_3$-$V_H$ or $V_L$-$L_1$-$V_H$-$L_2$-$V_H$-$L_3$-$V_L$ or $V_H$$L_1$-$V_L$-$L_2$-$V_H$$L_3$-$V_L$ or $V_H$-$L_1$-$V_L$-$L_2$-VL-$L_3$-$V_H$. Multivalent single chain antibodies which are trivalent or greater have one or more antibody fragments joined to a bivalent single chain antibody by additional peptide linkers. One example of a trivalent single chain antibody is: $V_L$-$L_1$-$V_H$-$L_2$-$V_L$-$L_1$-$V_H$-$L_2$-$V_L$-$L_1$-$V_H$.

Two single chain antibodies can be combined to form a diabody, also known as bivalent dimer. Diabodies have two chains. Each chain of the diabody includes a $V_H$ domain connected to a $V_L$ domain by a short linker of about 5-10 amino acid residues, e.g. (Gly-Gly-Gly-Gly-Ser), (Gly-Gly-Gly-Gly-Ser)$_2$. Such linkers are short enough to prevent intrachain pairing between domains on the same chain, thus driving interchain pairing between complementary domains on different chains and recreate two antigen-binding sites. The diabody structure is rigid and compact, with antigen-binding sites are at opposite ends of the molecule. Diabodies may be monospecfic or bispecific.

Three single chain antibodies can be combined to form a triabody, also known as a trivalent trimers. In some embodiments, triabodies are constructed with the carboxy terminus of a $V_L$ or $V_H$ domain directly fused to the amino terminus of a $V_H$ or $V_L$ domain, i.e., without any linker sequence. The triabody has three Fv heads with the polypeptides arranged in a cyclic, head-to-tail fashion. A possible conformation of the triabody molecule is planar with the three binding sites located in a plane at an angle of 120 degrees from one another. Triabodies may be monospecific, bispecific or trispecific.

It is understood that the anti-VEGFR2 antibodies of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibodies.

As set forth herein, the invention provides for administration of rho kinase inhibitors with angiogenesis inhibitors. Accordingly, the VEGFR antibodies of the invention can be administered with any rho kinase inhibitor, including but not limited to those disclosed herein, compounds disclosed in WO 2014/055996, WO 2014/055999, and WO 2006/105051, which are incorporated herein by reference.

The anti-VEGFR-2 antibodies of the invention may be administered with agents that target VEGF. Non-limiting examples of VEGF-binding agents include VEGF antibodies and VEGF traps (i.e., ligand binding domains of VEGF receptors. In general, a VEGF trap is a protein that comprises VEGF binding domains of one or more VEGF receptor protein. VEGF-traps include, without limitation, soluble VEGFR-1, soluble neuropilin 1 (NRP1), soluble VEGFR-3 (which binds VEGF-C and VEGF-D), and aflibercept (Zaltrap; Eyelea; VEGF Trap R1R2), comprised of segments of the extracellular domains of human vascular endothelial growth factor receptors VEGFR1 and VEGFR2 fused to the constant region (Fc) of human IgG1. Conbercept (KH902) is a fusion protein which contains the extracellular domain 2 of VEGFR-1 (Flt-1) and extracellular domain 3, 4 of VEGFR-2 (KDR) fused to the Fc portion of human IgG1. Several VEGF traps containing KDR and FLT-1 Ig-like domains in various combinations are disclosed in U.S. Pat. No. 8,216,575. DARPins (an acronym for designed ankyrin repeat proteins) are genetically engineered antibody mimetic proteins typically exhibiting highly specific and high-affinity target protein binding. DARPin® MP0112 is a vascular endothelial growth factor (VEGF) inhibitor and has entered clinical trials for the treatment of wet macular degeneration and diabetic macular edema.

According to the invention, VEGF expression can be targeted. For example, VEGF inhibitor PTC299 targets VEGF post-transcriptionally by selectively binding the 5'- and 3'-untranslated regions (UTR) of VEGF messenger RNA (mRNA), thereby preventing translation of VEGF. Pegaptanib (Macugen) is an RNA aptamer directed against VEGF-165.

Placental growth factor (PlGF) has been implicated in pathological angiogenesis. PlGF is structurally related to VEGF and is also a ligand for VEGFR-1. Consequently, VEGF traps comprising the extracellular domain of VEGFR1 (see above) are useful for targeting PlGF.

PDGF is composed of four polypeptide chains that form homodimers PDGF-AA, BB, CC, and DD as well as the heterodimer PDGF-AB. The PDGF receptors (PDGFR)-α and -β mediate PDGF functions. Specifically, PDGFRα binds to PDGF-AA, -BB, -AB, and -CC, whereas PDGFRβ interacts with -BB and -DD. Non-limiting examples of PDGF-binding agents include anti-PDGF antibodies and PDGF traps. Agents that target PDGF include Fovista™ (E10030, Ophthotech), a pegylated aptamer targeting PDGF-B, and AX102 (Sennino et al., 2007, Cancer Res. 75(15):7359-67), a DNA oligonucleotide aptamer that binds PDGF-B.

Agents that target PDGF receptors include ramucirumab (IMC-3G3, human $IgG_1$) an anti-PDGFRα antibody, crenolanib (CP-868596), a selective inhibitor of PDGFRα ($IC_{50}$=0.9 nM) and PDGFRβ ($IC_{50}$=1.8 nM), and nilotinib (Tasigna®), an inhibitor of PDGFRα and PDGFRβ and other tyrosine kinases.

Angiogenesis inhibitors include intracellular agents that block signal transduction mediated by, for example, VEGF, PDGF, ligands of VEGF or PDGF receptors, or complement. Intracellular agents that inhibit angiogenesis inhibitors include the following, without limitation. Sunitinib (Sutent; SU11248) is a panspecific small-molecule inhibitor of VEGFR1-VEGFR3, PDGFRα and PDGFRβ, stem cell factor receptor (cKIT), Flt-3, and colony-stimulating factor-1 receptor (CSF-1R). Axitinib (AG013736; Inlyta) is another small molecule tyrosine kinase inhibitor that inhibits VEGFR-1-VEGFR-3, PDGFR, and cKIT. Cediranib (AZD2171) is an inhibitor of VEGFR-1-VEGFR-3, PDGFRβ, and cKIT. Sorafenib (Nexavar) is another small molecular inhibitor of several tyrosine protein kinases, including VEGFR, PDGFR, and Raf kinases. Pazopanib (Votrient; (GW786034) inhibits VEGFR-1, -2 and -3, cKIT and PDGFR. Foretinib (GSK1363089; XL880) inhibits VEGFR2 and MET. CP-547632 is as a potent inhibitor of the VEGFR-2 and basic fibroblast growth factor (FGF) kinases. E-3810 ((6-(7-((1-aminocyclopropyl) methoxy)-6-methoxyquinolin-4-yloxy)-N-methyl-1-naphthamide) inhibits VEGFR-1, -2, and -3 and FGFR-1 and -2 kinases in the nanomolar range. Brivanib (BMS-582664) is a VEGFR-2 inhibitor that also inhibits FGF receptor signaling. CT-322 (Adnectin) is a small protein based on a human fibronectin domain and binds to and inhibits activation of VEGFR2. Vandetanib (Caprelas; Zactima; ZD6474) is an inhibitor of VEGFR2, EGFR, and RET tyrosine kinases. X-82 (Xcovery) is a small molecule indolinone inhibitor of signaling through the growth factor receptors VEGFR and PDGFR Anti-inflammatories and immunosuppressants include steroid drugs such as glucocortico ids (e.g., dexamethasone), FK506 (tacrolimus), ciclosporin, fingolimod, interferon, such as IFNβ or IFNγ, a tumor necrosis factor-alpha (TNF-α) binding protein such as infliximab (Remicade), etanercept (Enbrel), or adalimumab (Humira), and mycophenolic acid.

It is to be understood and expected that variations in the principles of invention herein disclosed may be made by one skilled in the art and it is intended that such modifications are to be included within the scope of the present invention.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

EXAMPLES

Abbreviations used in the following examples and preparations include:

$Ac_2O$ acetic anhydride
AcOH acetic acid
Bn Benzyl
Celite® diatomaceous earth
DCM dichloromethane
DIEA di-isopropylethylamine
DMAP 4-dimethylamino pyridine
DME 1,2-dimethoxyethane
DMF dimethylformamide
DMSO dimethyl sulfoxide
EDC 1-(3-dimethylaminopropyl)-3-ethylcarbodimide hydrochloride
EtOAc ethyl acetate
EtOH ethyl alcohol or ethanol
$Et_2O$ ethyl ether
$Et_3N$ triethylamine
g grams
HOBt 1-hydroxybenzotriazole
HPLC high pressure liquid chromatography
h hour(s)
MeCN acetonitrile
min minute(s)
MeOH methyl alcohol or methanol mL milliliter
mmol millimoles
MS mass spectrometry
NMR nuclear magnetic resonance
iPrOH iso-propanol
PyBOP® benzotriazol-1-yl-oxytripyrrolidinophosphonium
rt room temperature
s singlet
t triplet
THF tetrahydrofuran Mass spectrometry was conducted by: SynPep Co., 6905 Ct. Dublin, Calif. 94568, or it was recorded on an LC-MS: Waters 2695 Separations Module with a Waters ZQ2000 single quadrapole MS detector. Unless stated all mass spectrometry was run in ESI mode. $^1$H NMR spectra were recorded on a Varian 400 MHz machine using Mercury software. In so far the synthesis of the following examples of compounds of the present invention is not explicitly described in such example, the synthesis is as described herein in general terms and the appropriate starting material can be easily selected for synthesizing the compound of the example.

Example 1

N-(2-(5-Methoxyisoindolin-2-yl)pyrimidin-4-yl)-1H-indazol-5-amine

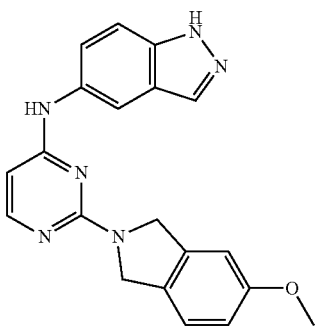 [SMILES: COc1ccc2c(c1)CN(c1nccc(Nc3ccc4[nH]ncc4c3)n1)C2]

N-(2-Chloropyrimidin-4-yl)-1H-indazol-5-amine

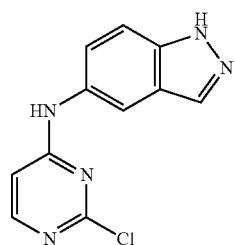 [SMILES: Clc1nccc(Nc2ccc3[nH]ncc3c2)n1]

To a solution of 2,4-dichloropyrimidine (2.0 g, 13.4 mmol) in ethanol (67 mL) was added 5-amino-indazole (1.79 g, 13.4 mmol) and triethylamine (2.81 mL, 20.1 mmol). The mixture was heated at reflux overnight. The reaction mixture was concentrated and the residue was recrystallized with methanol to afford the title compound as a pink solid (3.1 g, 97%).

N-(2-(5-Methoxyisoindolin-2-yl)pyrimidin-4-yl)-1H-indazol-5-amine

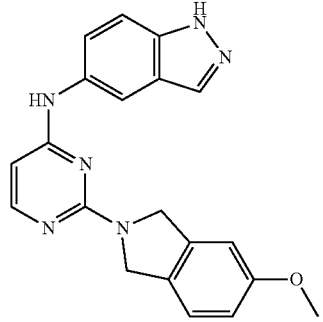 [SMILES: COc1ccc2c(c1)CN(c1nccc(Nc3ccc4[nH]ncc4c3)n1)C2]

A mixture of N-(2-chloropyrimidin-4-yl)-1H-indazol-5-amine (0.500 g, 2.04 mmol), 5-methoxyisoindoline hydrochloride (0.404 g, 2.18 mmol), and K$_2$CO$_3$ (0.844 g, 6.11 mmol) in DMF (4.07 mL) was stirred at 115° C. overnight. The mixture was diluted with water and extracted with EtOAc twice. The combined organic layers were washed with water and brine, dried over Na$_2$SO$_4$, concentrated, and purified by chromatography with MeOH in DCM. The product was further purified by recrystallization in EtOAc to provide the title compound as a light orange solid (215 mg, 30%). $^1$H NMR (300 MHz, DMSO-d$_6$) δ 13.15 (s, 1H), 9.45 (s, 1H), 8.52 (s, 1H), 8.29 (s, 1H), 8.16 (d, J=5.8 Hz, 1H), 7.81-7.66 (m, 2H), 7.59 (s, 1H), 7.25 (d, J=19.2 Hz, 1H), 7.10 (d, J=8.4 Hz, 1H), 6.29 (d, J=5.8 Hz, 1H), 5.01 (d, J=16.0 Hz, 4H), 3.99 (s, 3H). MS (ES+) m/e 359 (M+H)$^+$.

Example 2

N-(2-(Isoindolin-2-yl)pyrimidin-4-yl)-1H-indazol-5-amine

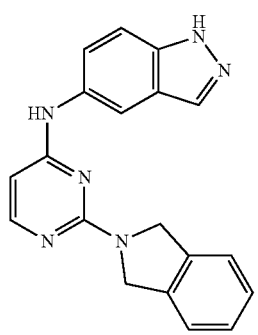 [SMILES: c1ccc2c(c1)CN(c1nccc(Nc3ccc4[nH]ncc4c3)n1)C2]

A mixture of N-(2-chloropyrimidin-4-yl)-1H-indazol-5-amine (0.200 g, 1.03 mmol), isoindoline (0.140 g, 1.03 mmol), and K$_2$CO$_3$ (0.171 g, 1.24 mmol) in DMF (6.89 mL) was stirred 80° C. for 4 h followed by at rt overnight. The mixture was diluted with water and extracted with EtOAc. The organic layer was washed with water, brine and dried over MgSO$_4$ to afford a crude brown oil which was recrystallized from 5% MeOH/DCM followed by further recrystallization in EtOH to afford the title compound as a grey solid (36.1 mg, 11%). $^1$H NMR (300 MHz, DMSO-d$_6$) δ 12.95 (s, 1H), 9.25 (s, 1H), 8.25 (s, 1H), 8.07 (s, 1H), 7.95 (d, J=4.4 Hz, 1H), 7.31-7.51 (m, 6H), 6.08 (d, J=4.4 Hz, 1H), 4.82 (d, J=24.7 Hz, 4H). MS (ES+) m/e 329 (M+H)$^+$.

Example 3

N-(5-Fluoro-2-(5-methoxyisoindolin-2-yl)pyrimidin-4-yl)-1H-indazol-5-amine

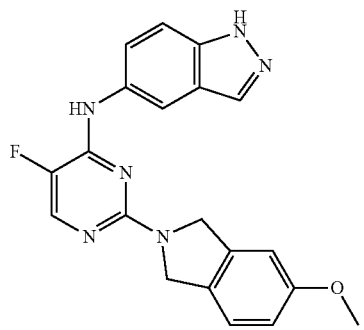 [SMILES: COc1ccc2c(c1)CN(c1ncc(F)c(Nc3ccc4[nH]ncc4c3)n1)C2]

N-(2-Chloro-5-fluoropyrimidin-4-yl)-1H-indazol-5-amine

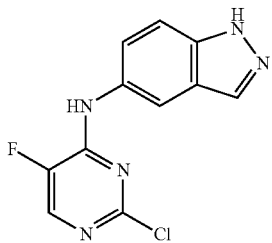 [SMILES: Fc1cnc(Cl)nc1Nc1ccc2[nH]ncc2c1]

To a solution of 2,4-dichloro-5-fluoropyrimidine (0.800 g, 4.55 mmol) in EtOH (40 mL) were added $Na_2CO_3$ (6.27 g, 45.5 mmol) and compound 1H-indazol-5-amine (0.605 g, 4.55 mmol). The resulting mixture was stirred for 12 h at 100° C. After LCMS showed the reaction was completed, the solvent was removed under reduced pressure and the residue was put into water (50 mL) and extracted with EtOAc (3×100 mL). The organic phase was dried over $Na_2SO_4$, filtered and concentrated under reduced pressure to give a residue which was purified by column chromatograph on silica gel (eluted with PE:EA=1:1) to give the title compound as a solid (120 mg, 9.7%).

N-(5-Fluoro-2-(5-methoxyisoindolin-2-yl)pyrimidin-4-yl)-1H-indazol-5-amine

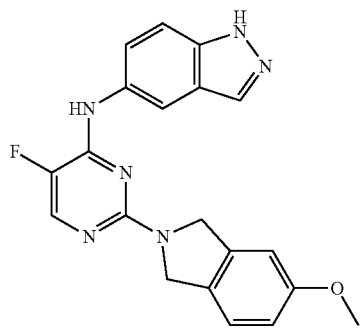 [SMILES: COc1ccc2c(c1)CN(c1ncc(F)c(Nc3ccc4[nH]ncc4c3)n1)C2]

To a solution of N-(2-chloro-5-fluoropyrimidin-4-yl)-1H-indazol-5-amine (300 mg, 1.14 mmol) in acetonitrile (4 mL) were added 5-methoxyisoindoline (170 mg, 1.14 mmol) and DIEA (441 mg, 3.42 mmol). The resulting mixture was heated at 90° C. for 12 h. After LCMS showed the reaction was completed, the mixture was concentrated and dissolved in methanol and purified by preparative HPLC, and lyophilized to give compound the title compound as a white solid (52 mg, 12.1%). $^1$H NMR (300 MHz, DMSO-$d_6$) δ 13.0 (s, 1H), 9.26 (s, 1H), 8.32 (s, 1H), 8.09 (s, 1H), 8.03 (d, J=4.0 Hz, 1H), 7.74 (d, J=8.8 Hz, 1H), 7.50 (d, J=9.2 Hz, 1H), 7.30 (b, 1H), 7.00 (b, 1H), 6.86 (dd, J=8.4 and 2.8 Hz, 1H), 4.72 (s, 2H), 4.69 (s, 2H), 3.76 (s, 3H). MS (ES+) m/e 377 (M+H)$^+$.

Example 4

N-(5-Chloro-2-(5-methoxyisoindolin-2-yl)pyrimidin-4-yl)-1H-indazol-5-amine

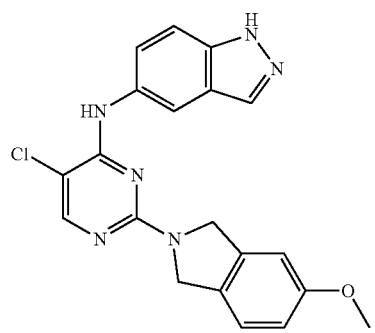 [SMILES: COc1ccc2c(c1)CN(c1ncc(Cl)c(Nc3ccc4[nH]ncc4c3)n1)C2]

N-(2,5-Dichloropyrimidin-4-yl)-1H-indazol-5-amine

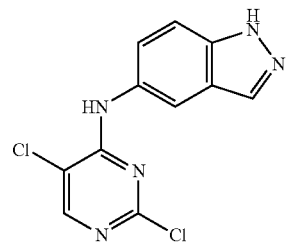 [SMILES: Clc1ncc(Cl)c(Nc2ccc3[nH]ncc3c2)n1]

To a solution of 2,4,5-trichloropyrimidine (1.00 g, 5.49 mmol) in EtOH (20 mL) were added $Na_2CO_3$ (3.03 g, 28.6 mmol) and compound 1H-indazol-5-amine (0.657 g, 4.94 mmol). The resulting mixture was stirred for 12 h at 15° C. After LCMS showed the reaction was completed, then the solvent was removed under reduced pressure and the residue was put into water (50 mL) and extracted with EtOAc (3×50 mL). The organic phase was dried over $Na_2SO_4$, filtered and concentrated under reduced pressure to give compound the title compound as a solid (800 mg, 52.3%).

N-(5-Chloro-2-(5-methoxyisoindolin-2-yl)pyrimidin-4-yl)-1H-indazol-5-amine

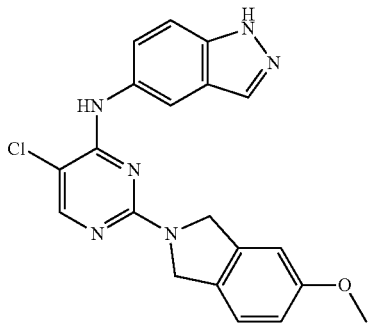 [SMILES: COc1ccc2c(c1)CN(c1ncc(Cl)c(Nc3ccc4[nH]ncc4c3)n1)C2]

To a solution of compound N-(2,5-dichloropyrimidin-4-yl)-1H-indazol-5-amine (281 mg, 1.01 mmol) in acetonitrile (5 mL) were added compound 5-methoxyisoindoline (150 mg, 1.01 mmol) and DIEA (391 mg, 3.03 mmol). The resulting mixture was heated at 90° C. for 12 h. After LCMS showed the reaction was completed, the mixture was concentrated and dissolved in methanol and purified by preparative HPLC, and lyophilized to give compound the title compound as a white solid (115 mg, 29.1%). $^1$H NMR (300 MHz, DMSO-d$_6$) δ 13.00 (s, 1H), 8.73 (s, 1H), 8.14 (s, 1H), 8.08 (s, 2H), 7.69 (d, J=8.8 Hz, 1H), 7.50 (s, J=8.8 Hz, 1H), 7.27 (b, 1H), 6.97 (b, 1H), 6.84 (d, J=8.4 Hz, 1H), 4.67 (t, J=16.4 Hz, 4H), 3.74 (s, 3H). MS (ES+) m/e 393 (M+H)$^+$.

Example 5

N-(2-(5-Methoxyisoindolin-2-yl)-5-methylpyrimidin-4-yl)-1H-indazol-5-amine

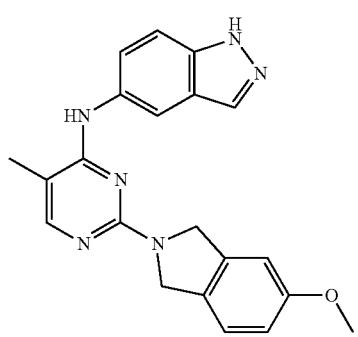

N-(2-Chloro-5-methylpyrimidin-4-yl)-1H-indazol-5-amine

To a solution of compound 2,4-dichloro-5-methylpyrimidine (1.00 g, 6.17 mmol) in EtOH (20 mL) were added Na$_2$CO$_3$ (3.27 g, 30.9 mmol) and compound 1H-indazol-5-amine (0.821 g, 6.17 mmol). The resulting mixture was stirred for 12 h at 90° C. After LCMS showed the reaction was completed, then the solvent was removed under reduced pressure and the residue was put into water (50 mL) and extracted with EtOAc (3×50 mL). The organic phase was dried over Na$_2$SO$_4$, filtered and concentrated under reduced pressure to give a residue which was purified by preparative HPLC to give compound the title compound as a solid (400 mg, yield: 25%).

N-(2-(5-Methoxyisoindolin-2-yl)-5-methylpyrimidin-4-yl)-1H-indazol-5-amine

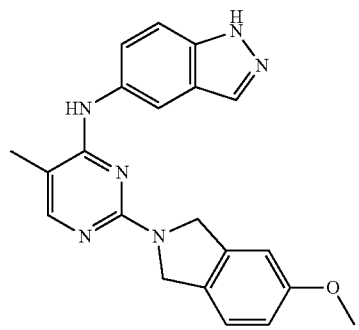

To a solution of compound N-(2-chloro-5-methylpyrimidin-4-yl)-1H-indazol-5-amine (261 mg, 1.01 mmol) in DMF (5 mL) were added compound 5-methoxyisoindoline (150 mg, 1.01 mmol) and DIEA (391 mg, 3.03 mmol). The resulting mixture was heated at 110° C. for 12 h. After LCMS showed the reaction was completed, the mixture was concentrated and dissolved in methanol and purified by preparative HPLC, and lyophilized to give compound the title compound as a white solid (105 mg, 27.0%). $^1$H NMR (300 MHz, DMSO-d$_6$) δ 12.92 (s, 1H), 8.25 (s, 1H), 8.18 (s, 1H), 8.06 (s, 1H), 7.81 (s, 1H), 7.72 (d, J=9.2 Hz, 1H), 7.48 (d, J=8.8 Hz, 1H), 7.25 (d, J=8.0 Hz, 1H), 6.98 (s, 1H), 6.83 (d, J=8.0 Hz, 1H), 4.70 (s, 2H), 4.65 (s, 2H), 3.75 (s, 3H), 2.09 (s, 3H). MS (ES+) m/e 373 (M+H)$^+$.

Example 6

N-(2-(5-Methoxyisoindolin-2-yl)-6-methylpyrimidin-4-yl)-1H-indazol-5-amine

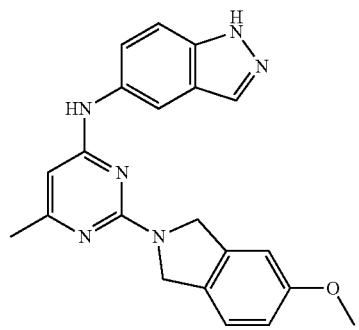

N-(2-Chloro-6-methylpyrimidin-4-yl)-1H-indazol-5-amine

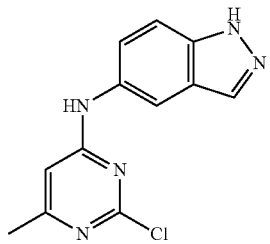 [SMILES: Cc1cc(Nc2ccc3[nH]ncc3c2)nc(Cl)n1]

To a solution of compound 2,4-dichloro-6-methylpyrimidine (1.00 g, 6.17 mmol) in EtOH (20 mL) were added Na$_2$CO$_3$ (3.27 g, 30.9 mmol) and compound 1H-indazol-5-amine (0.821 g, 6.17 mmol). The resulting mixture was stirred for 12 h at 90° C. After LCMS showed the reaction was completed, then the solvent was removed under reduced pressure and the residue was put into water (50 mL) and extracted with EtOAc (3×50 mL). The organic phase was dried over Na$_2$SO$_4$, filtered and concentrated under reduced pressure to give a residue which was purified by preparative HPLC to give compound the title compound as a solid (400 mg, 25%).

N-(2-(5-Methoxyisoindolin-2-yl)-6-methylpyrimidin-4-yl)-1H-indazol-5-amine

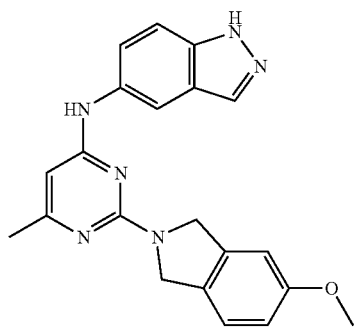

To a solution of compound N-(2-chloro-6-methylpyrimidin-4-yl)-1H-indazol-5-amine (261 mg, 1.01 mmol) in DMF (5 mL) were added compound 5-methoxyisoindoline (150 mg, 1.01 mmol) and DIEA (391 mg, 3.03 mmol). The resulting mixture was heated at 110° C. for 12 h. After LCMS showed the reaction was completed, the mixture was concentrated and dissolved in methanol and purified by preparative HPLC, and lyophilized to give compound the title compound as a white solid (80 mg, 21.4%). $^1$H NMR (300 MHz, DMSO-d$_6$) δ 12.91 (s, 1H), 9.08 (s, 1H), 8.25 (s, 1H), 8.06 (s, 1H), 7.47-7.53 (m, 2H), 7.29 (b, 1H), 7.00-7.05 (m, 1H), 6.87 (d, J=10.4 Hz, 1H), 5.93 (s, 1H), 5.76 (b, 4H), 3.77 (s, 3H), 2.17 (s, 3H). MS (ES+) m/e 373 (M+H)$^+$.

Example 7

N-(1H-Indazol-5-yl)-2-(5-methoxyisoindolin-2-yl)-5,7-dihydrofuro[3,4-d]pyrimidin-4-amine

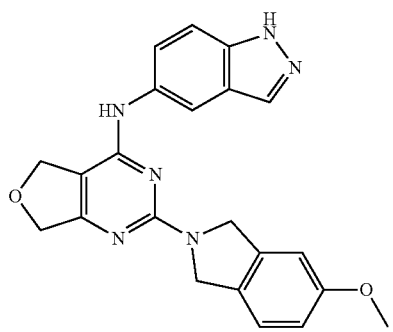 [SMILES: COc1ccc2c(c1)CN(c1nc3c(c(Nc4ccc5[nH]ncc5c4)n1)COC3)C2]

2-Chloro-N-(1H-indazol-5-yl)-5,7-dihydrofuro[3,4-d]pyrimidin-4-amine

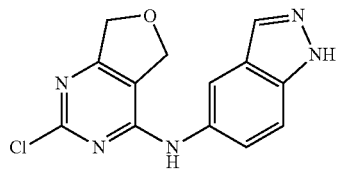

To a solution of compound 2,4-dichloro-5,7-dihydrofuro[3,4-d]pyrimidine (1.00 g, 5.30 mmol) in EtOH (30 mL) were added Na$_2$CO$_3$ (1.70 g, 15.8 mmol) and compound 1H-indazol-5-amine (711 mg, 5.3 mmol). The resulting mixture was stirred for 12 h at 15° C. After LCMS showed the reaction was completed, the solvent was removed under reduced pressure and the residue was dissolved in EtOAc (100 mL), washed by water (2×50 mL). The organic phase was dried over Na$_2$SO$_4$, filtered and concentrated under reduced pressure to give compound the title compound as a solid (800 mg, yield: 38.3%).

N-(1H-indazol-5-yl)-2-(5-methoxyisoindolin-2-yl)-5,7-dihydrofuro[3,4-d]pyrimidin-4-amine

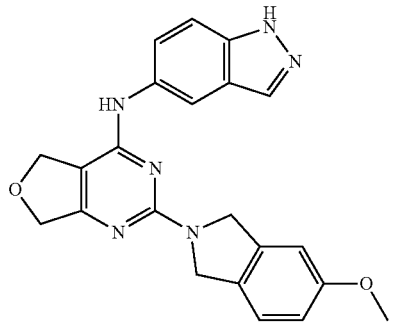 [SMILES: COc1ccc2c(c1)CN(c1nc3c(c(Nc4ccc5[nH]ncc5c4)n1)COC3)C2]

To a solution of compound 2-chloro-N-(1H-indazol-5-yl)-5,7-dihydrofuro[3,4-d]pyrimidin-4-amine (346 mg, 1.21 mmol) in acetonitrile (30 mL) were added compound 5-methoxyisoindoline (150 mg, 1.00 mmol) and DIEA (273 mg, 2.11 mmol). The resulting mixture was heated at 90° C. for 20 h. After LCMS showed the reaction was completed, the mixture was concentrated and dissolved in methanol and purified by preparative HPLC, and lyophilized to give the tilte compound (69.0 mg, 17.2%). $^1$H NMR (300 MHz, DMSO-d$_6$) δ 12.90 (s, 1H), 8.83 (s, 1H), 8.27 (s, 1H), 8.09 (s, 1H), 7.64 (d, J=8.8 Hz, 1H), 7.50 (d, J=8.8 Hz, 1H), 7.00-7.40 (m, 2H), 6.86 (dd, J=8.4 and 2.8 Hz, 1H), 4.73-4.89 (m, 8H), 3.77 (s, 3H). MS (ES+) m/e 401 (M+H)$^+$.

Example 8

N-(4-(5-Methoxyisoindolin-2-yl)pyrimidin-2-yl)-1H-indazol-5-amine

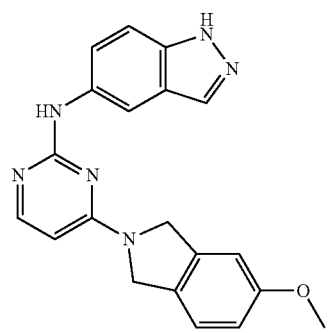 [SMILES: COc1ccc2c(c1)CN(c1ccnc(Nc3ccc4[nH]ncc4c3)n1)C2]

2-(2-Chloropyrimidin-4-yl)-5-methoxyisoindoline

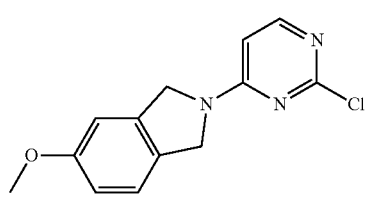 [SMILES: COc1ccc2c(c1)CN(c1ccnc(Cl)n1)C2]

To a solution of compound 2,4-dichloropyrimidine (298 mg, 2.01 mmol) in EtOH (10 mL) were added Na$_2$CO$_3$ (1.11 g, 10.5 mmol) and compound 5-methoxyisoindoline (300 mg, 2.01 mmol). The resulting mixture was stirred for 12 h at 90° C. After LCMS showed the reaction was completed, then the solvent was removed under reduced pressure and the residue was put into water (50 mL) and extracted with EtOAc (3×50 mL). The organic phase was dried over Na$_2$SO$_4$, filtered and concentrated under reduced pressure to give a residue which was purified by preparative TLC to give the title compound as a solid (250 mg, yield: 47.8%).

N-(4-(5-Methoxyisoindolin-2-yl)pyrimidin-2-yl)-1H-indazol-5-amine

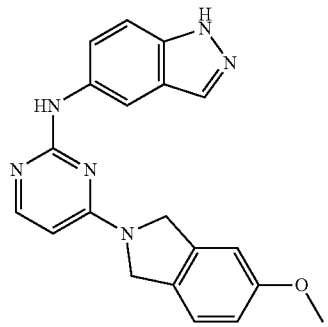 [SMILES: COc1ccc2c(c1)CN(c1ccnc(Nc3ccc4[nH]ncc4c3)n1)C2]

To a solution of compound 2-(2-chloropyrimidin-4-yl)-5-methoxyisoindoline (250 mg, 0.958 mmol) in DMF (20 mL) were added compound 5-aminoindazole (127 mg, 0.958 mmol) and DIEA (370 mg, 2.87 mmol). The resulting mixture was heated at 110° C. for 20 h. After LCMS showed the reaction was completed, the mixture was concentrated and purified by prep-HPLC, and lyophilized to give the title compound (51.7 mg, 17%). $^1$H NMR (300 MHz, DMSO-d$_6$) δ 12.83 (s, 1H), 9.03 (s, 1H), 8.33 (s, 1H), 8.00 (s, 1H), 7.99 (s, 1H), 7.62 (dd, J=9.2 and 2.0 Hz, 1H), 7.42 (d, J=8.8 Hz, 1H), 7.30 (b, 1H), 7.07 (b, 1H), 6.90 (d, J=8.4 Hz, 1H), 6.02 (d, J=6.4 Hz, 1H), 4.83 (d, J=14.4 Hz, 2H), 4.65 (d, J=17.6 Hz, 2H). 3.77 (s, 3H). MS (ES+) m/e 359 (M+H)$^+$.

Example 9

N-(2-(5-Fluoroisoindolin-2-yl)pyrimidin-4-yl)-1H-indazol-5-amine

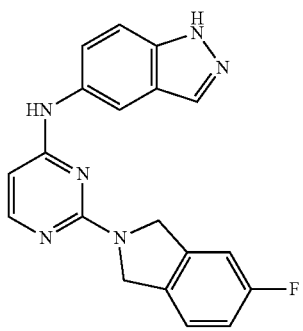 [SMILES: Fc1ccc2c(c1)CN(c1nccc(Nc3ccc4[nH]ncc4c3)n1)C2]

To a solution of N-(2-chloropyrimidin-4-yl)-1H-indazol-5-amine (457 mg, 1.87 mmol) in DMF (5 mL) were added compound 5-fluoroisoindole (250 mg, 1.87 mmol) and DIEA (724 mg, 5.61 mmol). The resulting mixture was heated at 110° C. for 20 h. After LCMS showed the reaction was completed, the mixture was concentrated and purified by prep-HPLC, and lyophilized to give the title compound (200 mg, 31.0%). $^1$H NMR (300 MHz, DMSO-d$_6$) δ 12.92 (s, 1H), 9.24 (s, 1H), 8.28 (s, 1H), 8.06 (s, 1H), 7.94 (d, J=6.0 Hz, 1H), 7.11-7.53 (m, 5H), 6.08 (d, J=6.4 Hz, 1H), 4.80 (b, 4H). MS (ES+) m/e 347 (M+H)$^+$.

Example 10

N-(2-(5-Chloroisoindolin-2-yl)pyrimidin-4-yl)-1H-indazol-5-amine

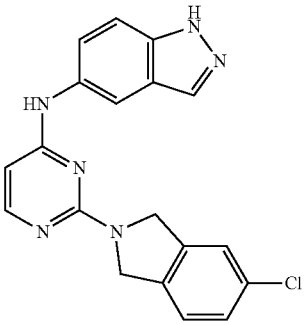 [SMILES: Clc1ccc2c(c1)CN(c1nccc(Nc3ccc4[nH]ncc4c3)n1)C2]

To a solution of N-(2-chloropyrimidin-4-yl)-1H-indazol-5-amine (384 mg, 1.57 mmol) in acetonitrile (5 mL) were added compound 5-chloroisoindoline (240 mg, 157 mmol) and DIEA (608 mg, 4.71 mmol). The resulting mixture was heated at 90° C. for 17 h. After LCMS showed the reaction was completed, the mixture was concentrated and the crude was washed with MeOH to give the title compound as a brown solid (230 mg, yield: 40.5%). $^1$H NMR (300 MHz, DMSO-$d_6$) δ 13.00 (s, 1H), 9.65 (s, 1H), 8.31 (s, 1H), 8.10 (s, 1H), 7.93 (d, J=6.0 Hz, 1H), 7.35-7.57 (m, 5H), 6.18 (d, J=6.0 Hz, 1H), 4.82 (b, 4H). MS (ES+) m/e 363 (M+H)$^+$.

Example 11

N-(2-(6-Methoxy-3,4-dihydroisoquinolin-2(1H)-yl)pyrimidin-4-yl)-1H-indazol-5-amine

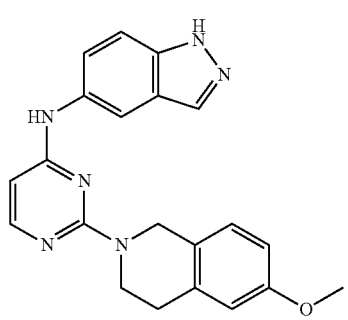 [SMILES: COc1ccc2c(c1)CCN(c1nccc(Nc3ccc4[nH]ncc4c3)n1)C2]

A mixture of N-(2-chloropyrimidin-4-yl)-1H-indazol-5-amine (100 mg, 0.41 mmol), 6-methoxy-1,2,3,4-tetrahydroisoquinoline (81.3 mg, 0.41 mmol), and $K_2CO_3$ (168 mg, 1.22 mmol) in DMF (1.2 mL) was stirred at 120° C. overnight, cooled to rt, diluted with water, and extracted with EtOAc. The organic layer was concentrated and the residue was purified by chromatography with 1-20% MeOH/DCM to provide the title compound as a white solid (42 mg, 28%). $^1$H NMR (300 MHz, DMSO-$d_6$) δ 12.96 (s, 1H), 9.21 (s, 1H), 8.13 (d, J=1.6 Hz, 1H), 8.04 (t, J=1.1 Hz, 1H), 7.93 (d, J=5.7 Hz, 1H), 7.56-7.41 (m, 2H), 7.15 (d, J=8.2 Hz, 1H), 6.84-6.72 (m, 2H), 6.03 (d, J=5.7 Hz, 1H), 4.79 (s, 2H), 3.95 (t, J=5.8 Hz, 2H), 3.73 (s, 3H), 2.85 (t, J=6.0 Hz, 2H). MS (ES+) m/e 373 (M+H)$^+$.

Example 12

N-(2-(6,7-Dihydrothieno[3,2-c]pyridin-5(4H)-yl)pyrimidin-4-yl)-1H-indazol-5-amine

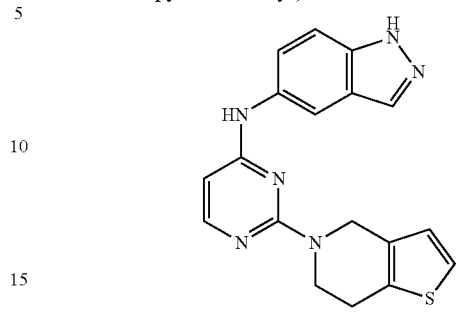

A mixture of N-(2-chloropyrimidin-4-yl)-1H-indazol-5-amine (100 mg, 0.41 mmol), 4-H thieno[3,2]pyridine (71.5 mg, 0.41 mmol), and $K_2CO_3$ (168 mg, 1.22 mmol) in DMF (1.2 mL) was stirred at 120° C. overnight, cooled to rt, diluted with water, and extracted with EtOAc. The organic layer was concentrated and the residue was purified by chromatography with 1-20% MeOH/DCM to provide the title compound as a white solid (33 mg, 23%). $^1$H NMR (300 MHz, DMSO-$d_6$) δ 12.97 (s, 1H), 9.23 (s, 1H), 8.12-8.01 (m, 2H), 7.93 (d, J=5.7 Hz, 1H), 7.56-7.40 (m, 2H), 7.34 (d, J=5.1 Hz, 1H), 6.97 (d, J=5.2 Hz, 1H), 6.04 (d, J=5.7 Hz, 1H), 4.80 (s, 2H), 4.07 (t, J=5.6 Hz, 2H), 2.93-2.82 (m, 2H). MS (ES+) m/e 349 (M+H)$^+$.

Example 13

N-(6-(5-Methoxyisoindolin-2-yl)pyrimidin-4-yl)-1H-indazol-5-amine

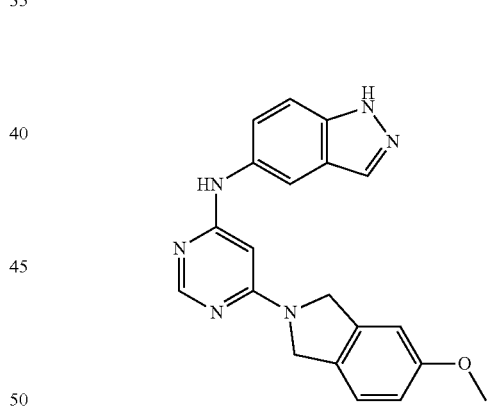

N-(6-Chloropyrimidin-4-yl)-1H-indazol-5-amine

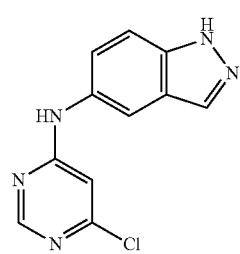 [SMILES: Clc1cc(Nc2ccc3[nH]ncc3c2)ncn1]

A mixture of 4,6-dichloropyrimidine (300 mg, 2.01 mmol), tert-butyl 5-amino-1H-indazole-1-carboxylate (470 mg, 2.01 mmol), diisopropylethylamine (0.74 mL, 3.03 mmol), and DMF (2.01 mL) was stirred at 80° C. overnight followed by 120° C. for 4 h. The mixture was cooled to rt, diluted with water, and extracted with EtOAc. The organic layer was concentrated in vacuo to provide the title compound which was carried out directly for next step reaction without further purification.

N-(6-(5-Methoxyisoindolin-2-yl)pyrimidin-4-yl)-1H-indazol-5-amine

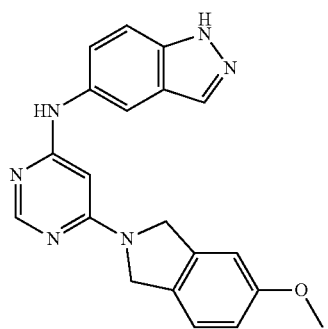 [SMILES: COc1ccc2c(c1)CN(c1cc(Nc3ccc4[nH]ncc4c3)ncn1)C2]

A mixture of N-(6-chloropyrimidin-4-yl)-1H-indazol-5-amine (150 mg, 0.61 mmol), 5-methoxyisoindoline hydrogen chloride (121 mg, 0.65 mmol), K$_2$CO$_3$ (253 mg, 1.83 mmol) in DMF (1.22 mL) was stirred at 100° C. for 2 h followed by 120° C. for 12h. The mixture was cooled to rt, diluted with water, and extracted with EtOAc. The organic layer was concentrated and purified by chromatography with 0-20% MeOH in DCM to provide the product which was further purified by trituration with DCM/Hex to provide pure title compound (30 mg, 14%). $^1$H NMR (300 MHz, DMSO-d$_6$) δ 12.95 (s, 1H), 9.02 (s, 1H), 8.22 (d, J=0.9 Hz, 1H), 8.01 (d, J=2.1 Hz, 2H), 7.55-7.36 (m, 2H), 7.31 (d, J=8.4 Hz, 1H), 7.00 (d, J=2.3 Hz, 1H), 6.89 (dd, J=8.4, 2.4 Hz, 1H), 5.74 (d, J=1.1 Hz, 1H), 4.65 (s, 4H), 3.77 (s, 3H). MS (ES+) m/e 359 (M+H)$^+$.

Example 14

N-(6-(5-Methoxyisoindolin-2-yl)-2-methylpyrimidin-4-yl)-1H-indazol-5-amine

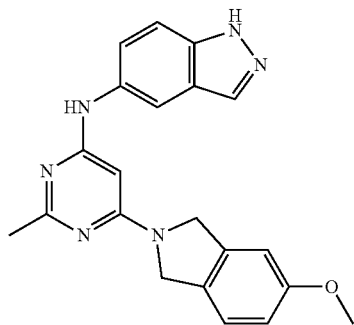

A mixture of N-(6-chloropyrimidin-4-yl)-1H-indazol-5-amine (159 mg, 0.61 mmol), 5-methoxyisoindoline hydrogen chloride (121 mg, 0.65 mmol), K$_2$CO$_3$ (253 mg, 1.83 mmol) in DMF (1.22 mL) was stirred at 100° C. for 2 h followed by 120° C. for 12h. The mixture was cooled to rt, diluted with water, and extracted with EtOAc. The organic layer was concentrated and purified by chromatography with 0-20% MeOH in DCM to provide the product which was further purified by trituration with DCM/Hex to provide pure title compound (25 mg, 11%). $^1$H NMR (300 MHz, DMSO-d$_6$) δ 12.95 (s, 1H), 8.90 (s, 1H), 7.98 (d, J=15.8 Hz, 2H), 7.54-7.36 (m, 2H), 7.29 (d, J=8.5 Hz, 1H), 6.99 (d, J=2.0 Hz, 1H), 6.88 (dd, J=8.3, 2.4 Hz, 1H), 5.60 (s, 1H), 4.63 (s, 4H), 3.76 (s, 3H), 2.34 (s, 3H). MS (ES+) m/e 373 (M+H)$^+$.

Example 15

N-(2-(1H-Pyrrolo[3,4-c]pyridin-2(3H)-yl)pyrimidin-4-yl)-1H-indazol-5-amine

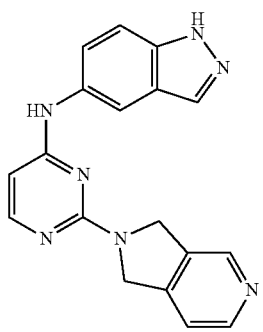 [SMILES: c1cc2c(cn1)CN(c1nccc(Nc3ccc4[nH]ncc4c3)n1)C2]

A mixture of N-(2-chloropyrimidin-4-yl)-1H-indazol-5-amine (100 mg, 0.41 mmol), 2,3-dihydro-1H-pyrrolo[3,4-c]pyridine dihydrogen chloride (102 mg, 0.53 mmol), diisopropylethylamine (0.74 mL, 1.22 mmol) in DMF (0.81 mL) was stirred at 110° C. overnight. The mixture was cooled to rt, diluted with water, and extracted with EtOAc. The organic layer was concentrated and purified by chromatography with 0-20% MeOH in DCM to provide the title compound (13 mg, 10%) as a slightly yellow solid. $^1$H NMR (300 MHz, DMSO-d$_6$) δ 12.95 (s, 1H), 9.29 (s, 1H), 8.69 (s, 1H), 8.52 (d, J=5.0 Hz, 1H), 8.29 (s, 1H), 8.08 (s, 1H), 7.97 (d, J=5.7 Hz, 1H), 7.61-7.46 (m, 3H), 6.11 (d, J=5.8 Hz, 1H), 4.88 (s, 4H). MS (ES+) m/e 330 (M+H)$^+$.

Example 16

N-(2-(5-Methoxyisoindolin-2-yl)-5,6-dimethylpyrimidin-4-yl)-1H-indazol-5-amine

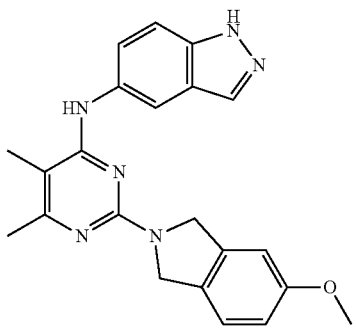

N-(2-Chloro-5,6-dimethylpyrimidin-4-yl)-1H-indazol-5-amine

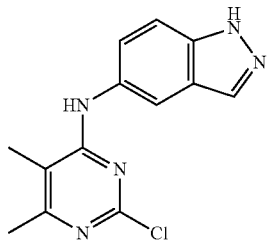 [SMILES: Cc1nc(Cl)nc(Nc2ccc3[nH]ncc3c2)c1C]

To a solution of 2,4-dichloro-5,6-dimethylpyrimidine (0.800 g, 4.55 mmol) in EtOH (40 mL) were added Na$_2$CO$_3$ (2.42 g, 22.8 mmol) and 1H-indazol-5-amine (0.605 g, 4.55 mmol). The resulting mixture was stirred for 12 h at 100° C. The solvent was removed under reduced pressure and the residue was poured into water (50 mL) and extracted with EtOAc (3×100 mL). The organic phase was dried over Na$_2$SO$_4$, filtered and concentrated under reduced pressure to give a residue which was purified by column chromatograph on silica gel (eluted with PE:EA=1:1) to provide the title compound (120 mg, yield: 9.7%) as a white solid.

N-(2-(5-Methoxyisoindolin-2-yl)-5,6-dimethylpyrimidin-4-yl)-1H-indazol-5-amine

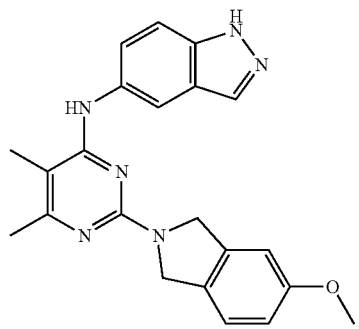

To a solution of N-(2-chloro-5,6-dimethylpyrimidin-4-yl)-1H-indazol-5-amine (1.0 g, 3.66 mmol) in CH$_3$CN (60 mL) were added 5-methoxyisoindoline (545 mg, 3.66 mmol) and K$_2$CO$_3$ (1.01 g, 7.33 mmol). The resulting mixture was heated at 90° C. for 72 h. After LCMS showed the reaction was completed, the mixture was concentrated and the crude was washed with MeOH to provide the title compound (423 mg, yield: 30.0%) as a brown solid. $^1$H NMR (300 MHz, DMSO-d$_6$) δ 12.95 (s, 1H), 8.08 (s, 1H), 8.01 (d, J=8.8 Hz, 1H), 7.30 (d, J=8.0 Hz, 1H), 7.00 (s, 1H), 6.90-6.83 (m, 4H), 4.81 (s, 2H), 4.77 (s, 2H), 3.75 (s, 3H), 2.44 (s, 3H), 2.77 (s, 3H). MS (ES+) m/e 387 (M+H)$^+$.

Example 17

N-(1H-Indazol-5-yl)-2-(isoindolin-2-yl)-5,7-dihydrofuro[3,4-d]pyrimidin-4-amine

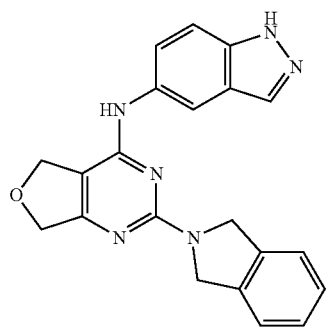 [SMILES: c1ccc2c(c1)CN(c1nc3c(c(Nc4ccc5[nH]ncc5c4)n1)COC3)C2]

The title compound was synthesized using the same procedure as described for the synthesis of Example 7 (KL-00230). $^1$H NMR (400 MHz, DMSO-d$_6$) δ 12.94 (s, 1H), 8.82 (s, 1H), 8.25 (s, 1H), 8.06 (s, 1H), 7.64-7.28 (m, 6H), 4.87-4.72 (m, 8H). MS (ES+) m/e 371 (M+H)$^+$.

Example 18

N-(4-(1H-pyrazol-4-yl)phenyl)-2-(5-methoxyisoindolin-2-yl)pyrimidin-4-amine

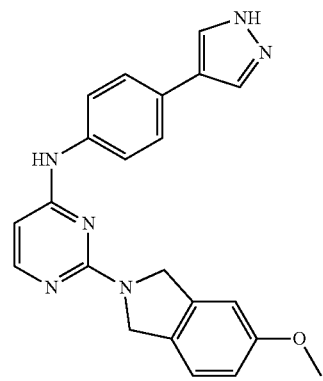 [SMILES: COc1ccc2c(c1)CN(c1nccc(Nc3ccc(-c4cn[nH]c4)cc3)n1)C2]

N-(4-Bromophenyl)-2-chloropyrimidin-4-amine

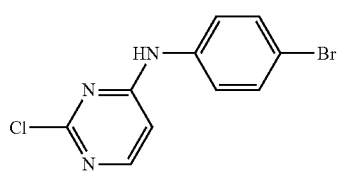 [SMILES: Clc1nccc(Nc2ccc(Br)cc2)n1]

To a solution of compound N-(4-bromophenyl)-2-chloropyrimidin-4-amine (2.00 g, 13.4 mmol) in EtOH (20 mL) were added Na$_2$CO$_3$ (4.26 g, 40.2 mmol) and compound 4-bromoaniline (2.3 g, 13.4 mmol). The resulting mixture was stirred for 12 h at 15° C. After LCMS showed the reaction was completed, then the solvent was removed under reduced pressure and the residue was put into water (50 mL) and extracted with EtOAc (3×50 mL). The organic phase was dried over Na₂SO₄, filtered and concentrated under reduced pressure to give a residue which was purified by washed with EA to give compound the title compound (1.20 g, yield: 31.6%) as a solid.

N-(4-Bromophenyl)-2-(5-methoxyisoindolin-2-yl)pyrimidin-4-amine

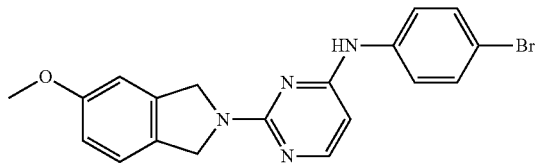 [SMILES: COc1ccc2c(c1)CN(c1nccc(Nc3ccc(Br)cc3)n1)C2]

To a solution of compound N-(4-bromophenyl)-2-chloropyrimidin-4-amine (1.00 g, 3.53 mmol) in acetonitrile (5 mL) were added compound 5-methoxyisoindoline (526 mg, 3.53 mmol) and DIEA (1.36 g, 10.6 mmol). The resulting mixture was heated at 90° C. for 17 h. After LCMS showed the reaction was completed, the mixture was concentrated and the crude was washed with MeOH to give compound the title compound (600 mg, yield: 42.9%) as a brown solid.

2-(5-Methoxyisoindolin-2-yl)-N-(4-(1-((2-(trimethylsilyl)ethoxy)methyl)-1H-pyrazol-4-yl)phenyl)pyrimidin-4-amine

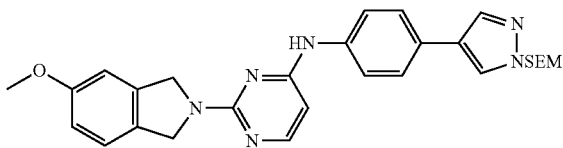 [SMILES: COc1ccc2c(c1)CN(c1nccc(Nc3ccc(-c4cnn(COCC[Si](C)(C)C)c4)cc3)n1)C2]

To the solution of compound N-(4-bromophenyl)-2-(5-methoxyisoindolin-2-yl)pyrimidin-4-amine (300 mg, 0.758 mol), compound 4-(4,4,5,5-tetramethyl-1,3,2-dioxaborolan-2-yl)-1-((2-(trimethylsilyl)ethoxy)methyl)-1H-pyrazole (492 mg, 1.52 mol) and K₂CO₃ (209 mg, 1.52 mol) were dissolved in dioxane/H₂O (2 mL/2 mL) and degassed with nitrogen for 10 minutes. Pd(dppf)Cl2 (27.7 mg, 0.0379 mmol) was added and the reaction mixture was stirred under nitrogen at 85° C. for 17 h. After LCMS showed the reaction was completed, then the mixture was concentrated used to next step.

N-(4-(1H-Pyrazol-4-yl)phenyl)-2-(5-methoxyisoindolin-2-yl)pyrimidin-4-amine

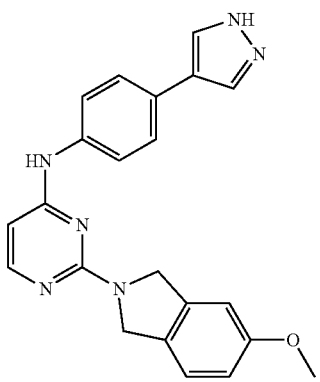 [SMILES: COc1ccc2c(c1)CN(c1nccc(Nc3ccc(-c4cn[nH]c4)cc3)n1)C2]

To the solution of compound 2-(5-methoxyisoindolin-2-yl)-N-(4-(1-((2-(trimethylsilyl)ethoxy)methyl)-1H-pyrazol-4-yl)phenyl)pyrimidin-4-amine (350 mg, 0.0195 mol) was dissolved in TFA (2 mL) and was stirred at 85° C. for 1 h. After LCMS showed the reaction was completed. Then TFA was removed and the residue was purified by prep-HPLC to give the title compound (53.1 mg, yield: 20.3%) as a brown solid. ¹H NMR (400 MHz, DMSO-d₆) δ 9.55 (s, 1H), 7.99 (s, 1H), 7.94 (d, J=6.0, 1H), 7.76 (d, J=8.4, 1H), 7.57 (d, J=8.4, 1H), 7.31 (s, 1H), 7.00 (s, 1H), 6.89 (d, J=8.4, 1H), 6.13 (d, J=5.6, 1H), 4.77 (m, 4H), 3.76 (s, 3H). MS (ES+) m/e 385 (M+H)⁺.

Example 19

2-(5-Methoxyisoindolin-2-yl)-N-(pyridin-4-yl)pyrimidin-4-amine

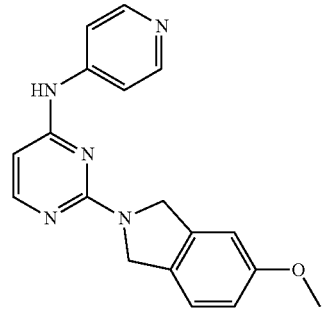 [SMILES: COc1ccc2c(c1)CN(c1nccc(Nc3ccncc3)n1)C2]

2-(5-Methoxyisoindolin-2-yl)pyrimidin-4-amine

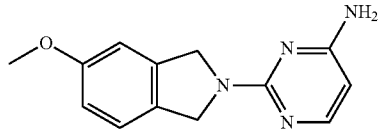 [SMILES: COc1ccc2c(c1)CN(c1nccc(N)n1)C2]

To a solution compound 2-chloropyrimidin-4-amine (381 mg, 2.95 mmol) and DIEA (692 mg, 5.37 mmol) in CH₃CN (20 mL) was added compound 5-methoxyisoindoline (400 mg, 2.68 mmol). Then the reaction was stirred at 90° C. for 16 h. After LCMS showed the reaction was complete. The crude product was purified by prep-TLC to give compound the title compound (230 mg, yield: 35.4%).

2-(5-Methoxyisoindolin-2-yl)-N-(pyridin-4-yl)pyrimidin-4-amine

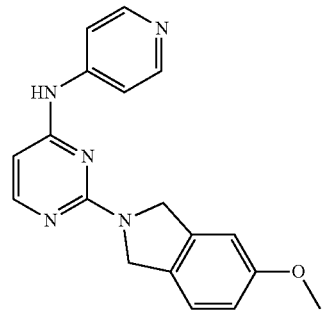 [SMILES: COc1ccc2c(c1)CN(c1nccc(Nc3ccncc3)n1)C2]

To a solution of 2-(5-methoxyisoindolin-2-yl)pyrimidin-4-amine (270 mg, 1.12 mmol) and 4-bromopyridine (193 mg, 1.23 mmol) in dioxane (20 mL) were added Cs$_2$CO$_3$ (1.09 g, 3.35 mmol) and stirred under N$_2$. Then xphos (32.2 mg, 0.0558 mmol) and Pd$_2$(dba)$_3$ (51.1 mg, 0.0558 mmol) were added and the reaction was stirred at 85° C. under N$_2$ for 16 h. After LCMS showed the reaction was completed. The crude product was purified by prep-HPLC to give the title compound (96.0 mg, yield: 26.9%). $^1$H NMR (400 MHz, DMSO-d$_6$) δ 9.69 (s, 1H), 8.38 (dd, J=4.8 and 1.6, 2H), 8.07 (d, J=5.2, 1H), 7.80 (dd, J=4.8 and 1.2, 2H), 7.33-7.89 (m, 1H), 7.04-6.98 (m, 1H), 6.86 (d, J=8.4, 1H), 6.16 (d, J=5.2, 1H), 4.87-4.71 (m, 4H), 3.76 (s, 3H). MS (ES+) m/e 320 (M+H)$^+$.

Example 20

2-(5-Methoxyisoindolin-2-yl)-N-(4-(pyridin-4-yl)phenyl)pyrimidin-4-amine

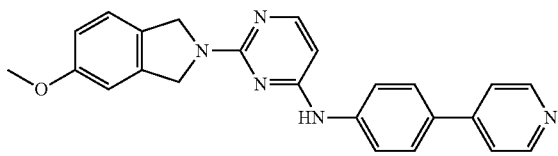 [SMILES: COc1ccc2c(c1)CN(c1nccc(Nc3ccc(-c4ccncc4)cc3)n1)C2]

A mixture of compound N-(4-bromophenyl)-2-(5-methoxyisoindolin-2-yl)pyrimidin-4-amine (297 mg, 0.748 mmol), pyridin-4-ylboronic acid (307 mg, 1.496 mmol), K$_2$CO$_3$ (206 mg, 1.496 mmol), PdCl$_2$(dppf) (30.5 mg, 0.0374 mmol) and dioxane (20 mL) and H$_2$O (20 mL) was stirred at 110° C. under N$_2$ for 12 h. After LCMS showed the reaction was completed, the mixture was cooled to 28° C., filtered and the filter cake was washed with MeOH (20 mL), dried to give the title compound (200 mg, yield: 67.6%) as a brown solid. $^1$H NMR (400 MHz, DMSO-d$_6$) δ 9.54 (s, 1H), 8.56 (s, 2H), 8.00-7.69 (m, 7H), 7.29-6.87 (m, 3H), 6.14 (s, 1H), 4.78-4.75 (m, 4H), 3.75 (s, 3H). MS (ES+) m/e 396 (M+H)$^+$.

Example 21

N-(1H-Indazol-5-yl)-2-(5-methoxyisoindolin-2-yl)-7,8-dihydro-5H-pyrano[4,3-d]pyrimidin-4-amine

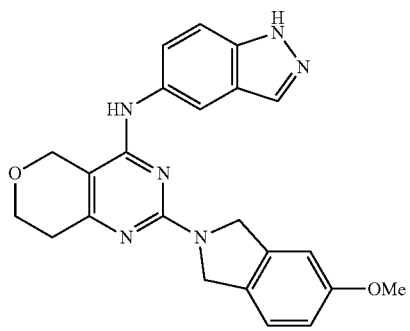 [SMILES: COc1ccc2c(c1)CN(c1nc3c(c(Nc4ccc5[nH]ncc5c4)n1)COCC3)C2]

Ethyl 4-oxotetrahydro-2H-pyran-3-carboxylate

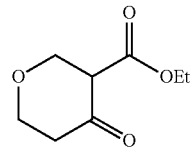 [SMILES: CCOC(=O)C1COCCC1=O]

To a solution of dihydro-2H-pyran-4(3H)-one (5.00 g, 50 mmol) in toluene (300 mL) was added LDA in hexane (27.5 mL, 55 mmol) quickly at 0° C. After stirring for 10 min, ethyl carbonocyanidate (4.45 g, 45 mmol) was added to the solution in one portion and the mixture was stirred for further 10 min. The mixture was quenched with AcOH (30 mL) and water (100 mL), and extracted with EtOAc (150 mL×3). The combined organic layers were washed with NaHCO$_3$ and brine, dried over Na$_2$SO$_4$ and concentrated to give the title compound (1.50 g, yield: 19.4%), which was used for the next step directly.

2-(Methylthio)-7,8-dihydro-3H-pyrano[4,3-d]pyrimidin-4(5H)-one

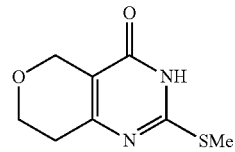 [SMILES: CSc1nc2c(c(=O)[nH]1)COCC2]

To a solution of sodium methoxide (62.8 mg, 1.16 mmol) in MeOH (5 mL) were added Ethyl 4-oxotetrahydro-2H-pyran-3-carboxylate (100 mg, 0.581 mmol) and methyl carbamimidothioate (78.5. mg, 0.872 mmol). The mixture was refluxed for 12 hrs. LCMS showed the reaction was completed. The solution was concentrated to give the crude product, which was purified by prep-TLC to give the titel compound (52 mg, yield: 45.2%). $^1$H NMR (400 MHz, MeOH) δ 4.44 (2H, s), 3.92 (2H, t, J=5.6 Hz), 2.64 (2H, t, J=5.6 Hz), 2.54 (3H, s).

4-Chloro-2-(methylthio)-7,8-dihydro-5H-pyrano[4,3-d]pyrimidine

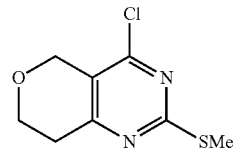

To a solution of 2-(methylthio)-7,8-dihydro-3H-pyrano[4,3-d]pyrimidin-4(5H)-one (1.00 g, 5.05 mmol) in MeCN (9.6 mL)/DMF (0.3 mL) was added POCl$_3$ (6.4 mL, 50.5 mmol) at 0° C. The mixture was heated to 80° C. and stirred for 16 hrs under N$_2$. After LCMS showed the reaction was completed, most POCl$_3$ was removed in vacuum and the residue was poured into ice water. The resultant mixture was neutralized to PH=7-8 with aq. Na$_2$CO$_3$ and extracted with EtOAc (100 mL×3). The combined organic layers were washed with brine, dried over Na₂SO₄ and concentrated to give the title compound (900 mg, yield: 82.6%), which was used for the next step directly. ¹H NMR (CDCl₃, 400 MHz) δ 4.69 (2H, s), 4.03 (2H, t, J=5.6 Hz), 2.92 (2H, t, J=5.6 Hz), 2.58 (3H, s).

N-(1H-Indazol-5-yl)-2-(methylthio)-7,8-dihydro-5H-pyrano[4,3-d]pyrimidin-4-amine

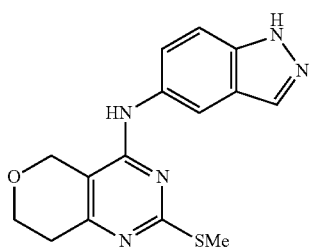 [SMILES: CSc1nc2c(c(Nc3ccc4[nH]ncc4c3)n1)COCC2]

To a solution of 4-chloro-2-(methylthio)-7,8-dihydro-5H-pyrano[4,3-d]pyrimidine (100 mg, 0.463 mmol) in dioxane (5 mL) were added KI (76.4 mg, 0.463 mmol), aq. HCl (0.2 mL) and 1H-indazol-5-amine (73.9 mg, 0.556 mmol) one by one. The resultant mixture was heated at 100° C. for 12 hours. After LCMS showed the reaction was completed. The mixture was concentrated to give the crude product, which was purified by prep-HPLC to give the title compound (45 mg, yield: 31.1%). ¹H NMR (400 MHz, DMSO-d₆) δ 9.23 (1H, s), 8.06 (1H, s), 7.88 (1H, s), 7.45-7.53 (2H, m) 4.60 (2H, s), 3.91 (2H, t, J=5.2 Hz), 2.70 (2H, t, J=5.2 Hz), 2.35 (3H, s).

N-(1H-Indazol-5-yl)-2-(methylsulfonyl)-7,8-dihydro-5H-pyrano[4,3-d]pyrimidin-4-amine

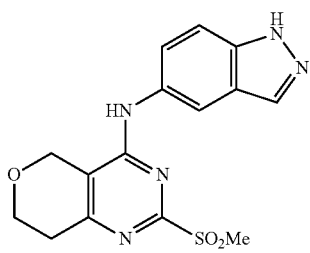 [SMILES: CS(=O)(=O)c1nc2c(c(Nc3ccc4[nH]ncc4c3)n1)COCC2]

To a solution of N-(1H-indazol-5-yl)-2-(methylthio)-7,8-dihydro-5H-pyrano[4,3-d]pyrimidin-4-amine (1.4 g, 4.47 mmol) in CH₂Cl₂ (10 mL)/dioxane (6 mL) was added m-CPBA (1.54 g, 8.94 mmol) in portionwise at 15° C. The mixture was stirred at 15° C. for 2~3 hours. LCMS showed the reaction was completed. The reaction mixture was concentrated under N₂ to give 1.5 g of title compound, which was used for the next step directly.

N-(1H-Indazol-5-yl)-2-(5-methoxyisoindolin-2-yl)-7,8-dihydro-5H-pyrano[4,3-d]pyrimidin-4-amine

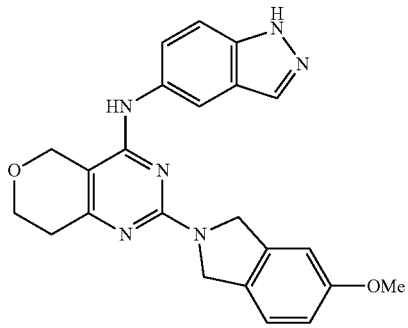 [SMILES: COc1ccc2c(c1)CN(c1nc3c(c(Nc4ccc5[nH]ncc5c4)n1)COCC3)C2]

To a solution of N-(1H-indazol-5-yl)-2-(methylsulfonyl)-7,8-dihydro-5H-pyrano[4,3-d]pyrimidin-4-amine (1.5 g, 4.34 mmol) in dioxane (20 mL) were added TEA (2.19 g, 21.7 mmol) and 5-methoxyisoindoline (1.30 g, 8.69 mmol). The sealed tube was heated at 150° C. for 2 hours under microwave. LC-MS showed the starting material was consumed. The mixture was concentrated in vacuum. The residue was purified by column chromatography on silica gel and prep-HPLC to give the title compound (130 mg, yield: 7.23%). ¹H NMR (400 MHz, CD3OD) δ 8.10 (1H, s), 8.02 (1H, s), 7.68 (1H, d, J=9.2 Hz), 7.49 (1H, d, J=8.8 Hz), 7.19 (1H, d, J=8.4 Hz), 6.88 (1H, s), 6.82 (1H, d, J=8.4 Hz), 4.74 (2H, s), 4.70 (2H, s), 4.63 (2H, s), 3.99 (2H, t, J=5.2 Hz), 3.78 (3H, s), 2.72 (2H, t, J=5.2 Hz). MS (ES+) m/e 415.2 (M+H)⁺.

Example 22 (KL-00254)

N-(1H-Indazol-5-yl)-2-(5-methoxyisoindolin-2-yl)-6-methyl-6,7-dihydro-5H-pyrrolo[3,4-d]pyrimidin-4-amine

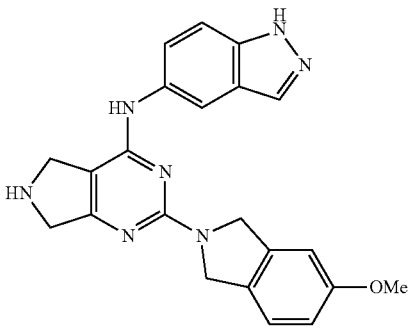 [SMILES: COc1ccc2c(c1)CN(c1nc3c(c(Nc4ccc5[nH]ncc5c4)n1)CNC3)C2]

tert-Butyl 4-((1H-indazol-5-yl)amino)-2-chloro-5H-pyrrolo[3,4-d]pyrimidine-6(7H)-carboxylate

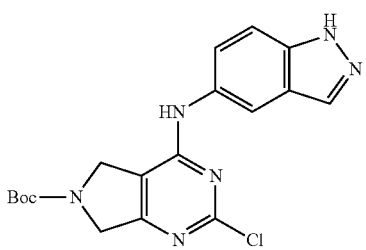 [SMILES: CC(C)(C)OC(=O)N1Cc2nc(Cl)nc(Nc3ccc4[nH]ncc4c3)c2C1]

A mixture of tert-butyl 2,4-dichloro-5H-pyrrolo[3,4-d]pyrimidine-6(7H)-carboxylate (1.0 g, 3.46 mmol), 1H-indazol-5-amine (0.55 g, 4.15 mmol) and Na$_2$CO$_3$ (1.1 g, 10.38 mmol) in DMF (20 mL) were heated at 100° C. for 2.5 h. The reaction mixture was cooled to room temperature, diluted with water and extracted with EtOAc (3×20 mL). The combined organic layers were concentrated in vacuum. The residue was purified by column chromatography on silica gel to give the title compound (0.9 g, yield: 67.7%). $^1$H NMR (400 MHZ, MeOD) δ 13.05 (1H, S), 9.57 (1H, S), 8.06 (1H, S), 7.95 (1H, M), 7.53-7.47 (2H, M), 4.41-4.39 (4H, S), 1.43 (9H, S).

tert-Butyl 4-((1H-indazol-5-yl)amino)-2-(5-methoxyisoindolin-2-yl)-5H-pyrrolo[3,4-d]pyrimidine-6(7H)-carboxylate

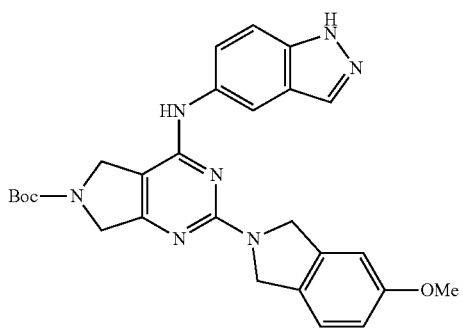 [SMILES: COc1ccc2c(c1)CN(c1nc3c(c(Nc4ccc5[nH]ncc5c4)n1)CN(C(=O)OC(C)(C)C)C3)C2]

A mixture of tert-butyl 4-((1H-indazol-5-yl)amino)-2-chloro-5H-pyrrolo[3,4-d]pyrimidine-6(7H)-carboxylate (1.50 g, 3.89 mmol), 5-methoxyisoindoline (0.87 g, 5.38 mmol) and TEA (1.18 g, 11.7 mmol) in NMP (30 mL) was heated at 150° C. for 1 h. The reaction mixture was cooled to room temperature, filtrated and purified by prep-HPLC to give the title compound (0.95 g, 48.9%). $^1$H NMR (400 MHZ, DMSO) δ 8.20-8.10 (2H, M), 7.75-7.57 (2H, M), 7.25-7.23 (1H, D), 6.91-6.88 (2H, M), 4.89 (4H, M), 4.59-4.48 (3H, M), 3.79 (3H, S), 1.49 (9H, S).

N-(1H-Indazol-5-yl)-2-(5-methoxyisoindolin-2-yl)-6,7-dihydro-5H-pyrrolo[3,4-d]pyrimidin-4-amine

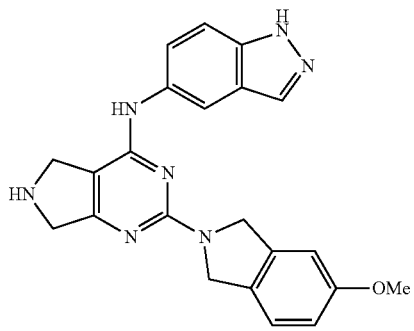 [SMILES: COc1ccc2c(c1)CN(c1nc3c(c(Nc4ccc5[nH]ncc5c4)n1)CNC3)C2]

A mixture of tert-butyl 4-((1H-indazol-5-yl)amino)-2-(5-methoxyisoindolin-2-yl)-5H-pyrrolo[3,4-d]pyrimidine-6(7H)-carboxylate (0.95 g, 1.9 mmol) and TFA (20 mL) in DCM (20 mL) was stirred at 25° C. for 1 h. LCMS showed the reaction was completed. The mixture was concentrated in vacuum and purified by prep-HPLC to give the title compound (380 mg). $^1$H NMR (400 MHZ, MeOD) δ 8.13-8.11 (2H, M), 7.66-7.60 (2H, M), 7.27-7.25 (1H, D), 6.91-6.88 (2H, M), 4.91-4.86 (4H, M), 4.57-4.51 (4H, M), 3.79 (3H, S). MS (ES+) M/E 400.2 (M+H)$^+$.

Example 23

N-(1H-Indazol-5-yl)-2-(5-methoxyisoindolin-2-yl)-6-methyl-6,7-dihydro-5H-pyrrolo[3,4-d]pyrimidin-4-amine

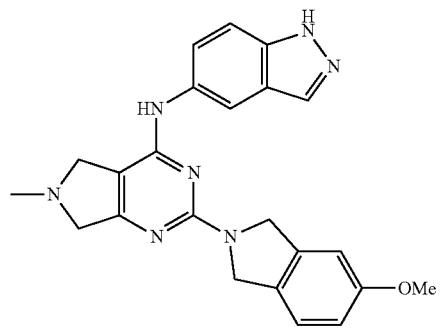 [SMILES: COc1ccc2c(c1)CN(c1nc3c(c(Nc4ccc5[nH]ncc5c4)n1)CN(C)C3)C2]

((1H-Indazol-5-yl)(2-(5-methoxyisoindolin-2-yl)-6-methyl-6,7-dihydro-5H-pyrrolo[3,4-d]pyrimidin-4-yl)amino)methanol

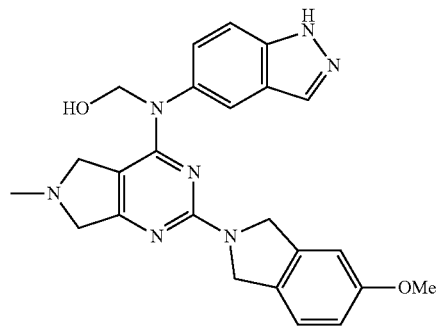 [SMILES: COc1ccc2c(c1)CN(c1nc3c(c(N(CO)c4ccc5[nH]ncc5c4)n1)CN(C)C3)C2]

A mixture of N-(1H-indazol-5-yl)-2-(5-methoxyisoindolin-2-yl)-6,7-dihydro-5H-pyrrolo[3,4-d]pyrimidin-4-amine (1.0 g, 2.5 mmol) and HCHO (4 mL) in MeOH (20 mL) was stirred at 25° C. for 1 h. NaBH$_3$CN (100 mg, 3 mmol) was added and the mixture was stirred at 25° C. for 10 h. LCMS showed the reaction was completed. The mixture was concentrated in vacuum to give the crude product, which was used directly for the next step.

N-(1H-Indazol-5-yl)-2-(5-methoxyisoindolin-2-yl)-6-methyl-6,7-dihydro-5H-pyrrolo[3,4-d]pyrimidin-4-amine

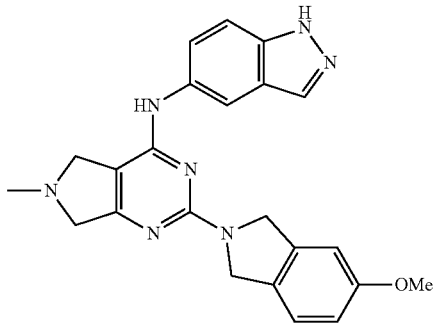 [SMILES: COc1ccc2c(c1)CN(c1nc3c(c(Nc4ccc5[nH]ncc5c4)n1)CN(C)C3)C2]

A mixture of ((1H-indazol-5-yl)(2-(5-methoxyisoindolin-2-yl)-6-methyl-6,7-dihydro-5H-pyrrolo[3,4-d]pyrimidin-4-yl)amino)methanol (1.2 g, 2.7 mmol) and HCl (5 mL) in MeOH (20 ml) was stirred at 25° C. for 1.5 h. LCMS showed the reaction was completed. The mixture was concentrated and purified by prep-HPLC to give the title compound (100 mg, 9.0%). $^1$H NMR (400 MHZ, MeOD) δ 8.13-8.10 (2H, M), 7.66-7.58 (2H, M), 7.27-7.25 (1H, D), 6.94-6.87 (2H, M), 4.85 (4H, M), 4.61-4.56 (4H, M), 3.80 (3H, S). MS (ES+) M/E 414.1 (M+H)$^+$.

Example 24

N-(1H-Indazol-5-yl)-2-(5-methoxyisoindolin-2-yl)-5,6,7,8-tetrahydropyrido[3,4-d]pyrimidin-4-amine

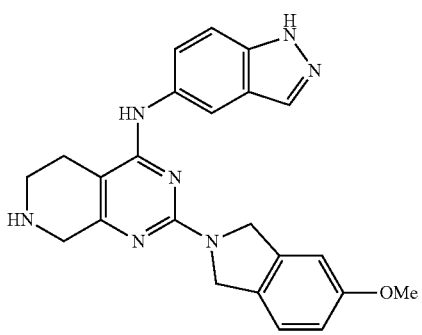 [SMILES: COc1ccc2c(c1)CN(c1nc3c(c(Nc4ccc5[nH]ncc5c4)n1)CCNC3)C2]

tert-Butyl 4-((1H-indazol-5-yl)amino)-2-chloro-5,6-dihydropyrido[3,4-d]pyrimidine-7(8H)-carboxylate

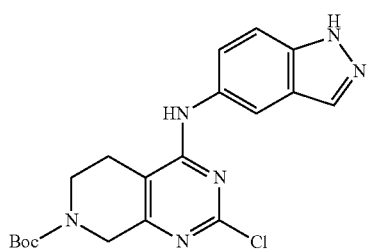 [SMILES: CC(C)(C)OC(=O)N1CCc2c(nc(Cl)nc2Nc2ccc3[nH]ncc3c2)C1]

A mixture of tert-butyl 2,4-dichloro-5,6-dihydropyrido[3,4-d]pyrimidine-7(8H)-carboxylate (1.50 g, 4.95 mmol), 1H-indazol-5-amine (0.66 g, 4.95 mmol) and Na$_2$CO$_3$ (1.05 g, 9.9 mmol) in DMF (30.0 mL) was heated at 100° C. for 3 h. LCMS showed the reaction was completed. The insoluble solid was removed by filtration and the filtrates were purified by HPLC to give the title compound (400 mg, 20.2%). $^1$H NMR (400 MHz, MeOD) δ 8.02 (1H, S), 7.96 (1H, S), 7.52 (2H, S), 4.41 (2H, M), 3.74 (2H, M), 2.65-2.62 (2H, M), 1.49 (9H, S).

tert-Butyl 4-((1h-indazol-5-yl)amino)-2-(5-methoxyisoindolin-2-yl)-5,6-dihydropyrido[3,4-d]pyrimidine-7(8h)-carboxylate

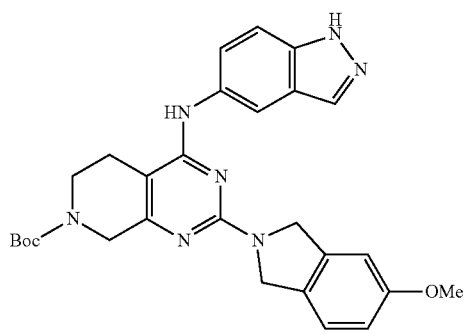 [SMILES: COc1ccc2c(c1)CN(c1nc3c(c(Nc4ccc5[nH]ncc5c4)n1)CCN(C(=O)OC(C)(C)C)C3)C2]

A mixture of tert-butyl 4-((1H-indazol-5-yl)amino)-2-chloro-5,6-dihydropyrido[3,4-d]pyrimidine-7(8H)-carboxylate (360 mg), 0.59 mmol methoxyisoindoline (201 mg, 1.35 mmol) and TEA (272 mg, 2.7 mmol) in NMP (20 mL) was heated at 150° C. for 1 h. The reaction mixture was cooled to room temperature, filtrated and purified by prep-HPLC to give the title compound (110 mg, 29.6%). $^1$H NMR (400 MHz, MeOD) δ 8.08-8.02 (2H, M), 7.64-7.56 (2H, M), 7.17 (2H, B), 6.84-6.83 (2H, M), 4.70-4.53 (6H, M), 3.84-3.82 (5H, M), 2.68-2.57 (2H, M), 1.53 (9H, S).

n-(1H-Indazol-5-yl)-2-(5-methoxyisoindolin-2-yl)-5,6,7,8-tetrahydropyrido[3,4-d]pyrimidin-4-amine

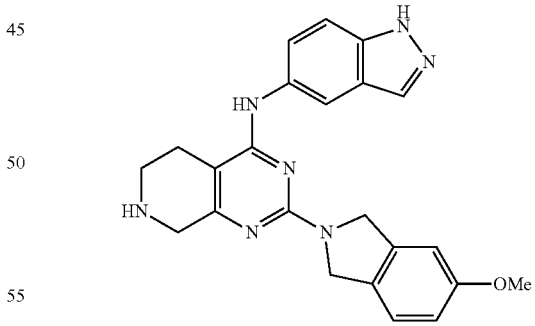

A mixture of tert-butyl 4-((1H-indazol-5-yl)amino)-2-(5-methoxyisoindolin-2-yl)-5,6-dihydropyrido[3,4-d]pyrimidine-7(8H)-carboxylate (110 mg, 0.21 mmol) and TFA (3 mL) in DCM (3 mL) was stirred at 25° C. for 1 It After LCMS showed the reaction was completed, the mixture was concentrated to give the title compound (75 mg, 88%). $^1$H NMR (400 MHz, MeOD) δ 8.12 (1H, s), 8.00 (1H, s), 7.63 (2H, m), 7.22 (2H, brs), 6.90-6.87 (2H, m), 4.80-4.79 (4H, m), 4.40 (2H, s), 3.76 (2H, s), 3.66-3.63 (2H, m), 2.95-2.92 (2H, m). MS (ES+) m/e 414.1 (M+H)$^+$.

Example 25

N-(1H-Indazol-5-yl)-2-(5-methoxyisoindolin-2-yl)-7-methyl-5,6,7,8-tetrahydropyrido[3,4-d]pyrimidin-4-amine

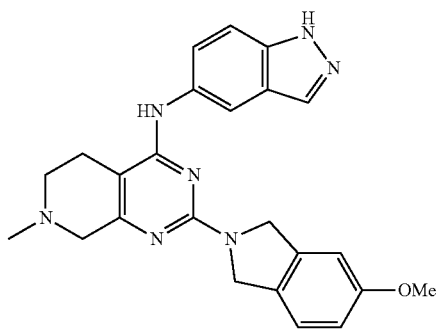 [SMILES: COc1ccc2c(c1)CN(c1nc3c(c(Nc4ccc5[nH]ncc5c4)n1)CCN(C)C3)C2]

((1H-Indazol-5-yl)(2-(5-methoxyisoindolin-2-yl)-7-methyl-5,6,7,8-tetrahydropyrido[3,4-d]pyrimidin-4-yl)amino)methanol

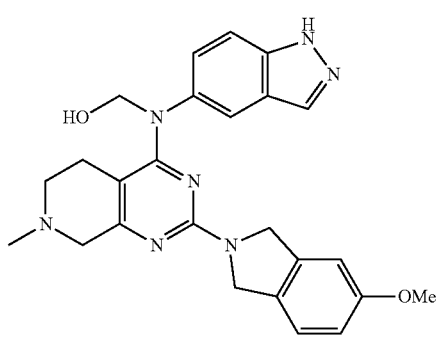 [SMILES: COc1ccc2c(c1)CN(c1nc3c(c(N(CO)c4ccc5[nH]ncc5c4)n1)CCN(C)C3)C2]

A mixture of N-(1H-indazol-5-yl)-2-(5-methoxyisoindolin-2-yl)-5,6,7,8-tetrahydropyrido[3,4-d]pyrimidin-4-amine (300 mg, 0.73 mmol) and HCHO (1 mL) in MeOH (10 mL) was stirred at 25° C. for 1 h. Then NaBH$_3$CN (30 mg, 1 mmol) was added and the mixture was stirred at 25° C. for 10 h. LCMS showed the reaction was completed. The mixture was concentrated and used in the next step.

n-(1H-Indazol-5-yl)-2-(5-methoxyisoindolin-2-yl)-7-methyl-5,6,7,8-tetrahydropyrido[3,4-d]pyrimidin-4-amine

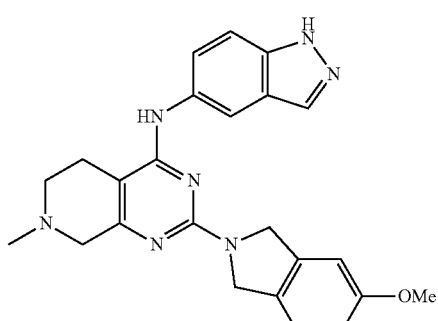

A mixture of ((1H-indazol-5-yl)(2-(5-methoxyisoindolin-2-yl)-7-methyl-5,6,7,8-tetrahydropyrido[3,4-d]pyrimidin-4-yl)amino)methanol (400 mg, 0.87 mmol) and HCl (2 mL) in MeOH (10 ml) was stirred at 25° C. for 1.5 h. After LCMS showed the reaction was completed, the mixture was concentrated and purified by HPLC to give the title compound (86 mg, 23.2%). $^1$H NMR (400 MHZ, MeOD) δ 8.12 (1H, S), 8.01 (1H, S), 7.63 (2H, M), 7.23 (2H, B), 6.90-6.88 (2H, M), 4.80 (4H, M), 4.46 (2H, S), 3.77-3.70 (5H, M), 3.15 (3H, S), 3.03-3.00 (2H, M). MS (ES+) M/E 428.2 (M+H)$^+$.

Example 26

2-(4-((1H-Indazol-5-yl)amino)pyrimidin-2-yl)isoindoline-5-carbonitrile

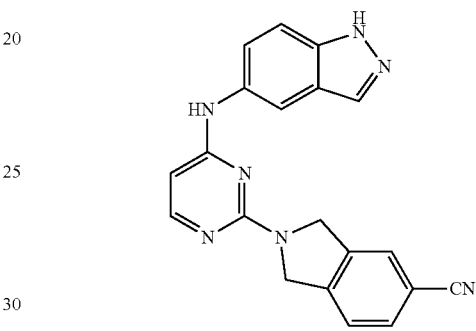

5-Bromoisoindoline

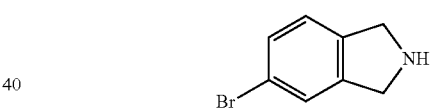

To a solution of 5-bromoisoindoline-1,3-dione (25.0 g, 0.11 mmol) in THF (1000 mL) were added BH$_3$Me$_2$S (100 mL). The resulting mixture was heated at 80° C. for 17 h. After LCMS showed the reaction was completed, the reaction mixture was quenched with MeOH and concentrated. The residue was purified by column chromatograph on silica gel (eluted with PE:EA=20:1) to give the title compound (3.98 g, 18.2%). $^1$H NMR (400 MHz, MeOD) δ 7.62 (1H, s) 7.55 (1H, d, J=8.0 Hz) 7.35 (1H, d, J=8.0 Hz) 4.62 (2H, s) 4.58 (2H, s).

tert-Butyl 5-bromoisoindoline-2-carboxylate

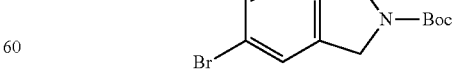

To a solution of 5-bromoisoindoline (3.98 g, 20.2 mmol) in DMF (20 ml) was added DMAP (40.0 mg) and BOC$_2$O (8.81 g, 40.4 mmol). The mixture was stirred at 25° C. for 10 h. After LC-MS showed the reaction was completed. The reaction mixture was concentrated to give the crude product, which was washed with pe to give the title compound (5.00 g, 83.4%). ¹H NMR (400 MHz, CDCl₃) δ 7.39-7.43 (2H, m) 7.09-7.18 (1H, m) 4.61-4.68 (4H, m) 1.53 (9H, s).

tert-Butyl 5-cyanoisoindoline-2-carboxylate

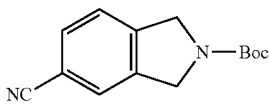 [SMILES: CC(C)(C)OC(=O)N1Cc2ccc(C#N)cc2C1]

To a solution of tert-butyl 5-bromoisoindoline-2-carboxylate (5.00 g, 16.8 mmol) in DMF (150 ml) was added ZN(CN)₂ (3.94 g, 33.5 mmol) and Pd(PPh₃)₄ (3.62 g). The mixture was stirring at 80° C. for 3 h. After LC-MS showed the reaction was completed, the mixture was concentrated and the residue was purified by column chromatograph on silica gel (eluted with PE:EA=30:1) to give the title compound (4.00 g, 97.6%). ¹H NMR (400 MHz, CDCl₃) δ 7.53-7.60 (2H, m) 7.33-7.42 (1H, m) 4.71-4.76 (4H, m) 1.53 (9H, s).

Isoindoline-5-carbonitrile

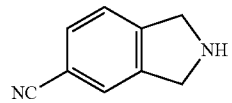 [SMILES: N#Cc1ccc2c(c1)CNC2]

The solution of tert-butyl 5-cyanoisoindoline-2-carboxylate (4.00 g, 16.4 mmol) in TFA/DCM (2M, 100 ml) was stirring at 15° C. for 120 min. After LC-MS showed the reaction was completed, the reaction solution was concentrated to give the title compound (2.36 g, 99.9%), which was used for the next step directly.

2-(4-((1H-Indazol-5-yl)amino)pyrimidin-2-yl)isoindoline-5-carbonitrile

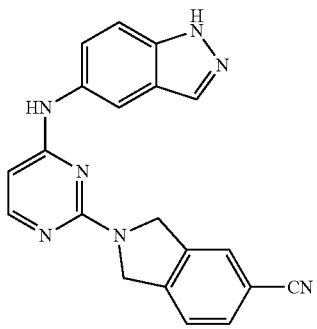 [SMILES: N#Cc1ccc2c(c1)CN(c1nccc(Nc3ccc4[nH]ncc4c3)n1)C2]

To a solution of compound isoindoline-5-carbonitrile (200 mg, 1.39 mmol) in DMF (5 ml) was added TEA (200 mg) and 4-methyl-N,N-di(prop-2-yn-1-yl)benzenesulfonamide (170 mg, 0.694 mmol). The mixture was stirred at 80° C. for 5 h. After LC-MS showed the reaction was completed, the solution was concentrated to give the crude product, which was purified by prep-hplc to give the title compound (130 mg, 53.0%). ¹H NMR (400 MHz, DMSO) δ 10.81 (1H, b), 8.29 (1H, b) 8.17 (1H, s), 8.01 (1H, d, J=8.0 Hz), 7.94 (1H, d, J=6.8 Hz) 7.85 (1H, d, J=6.8 Hz) 7.65-7.67 (1H, m), 7.60 (3H, Br. s.), 6.42 (1H, Br. s.), 4.92-5.03 (4H, m). MS (ES+) M/E 354.1 (M+H)⁺.

Example 27

N-(2-(5-(Methoxymethyl)isoindolin-2-yl)pyrimidin-4-yl)-1H-indazol-5-amine

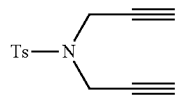

4-Methyl-n,n-di(prop-2-yn-1-yl)benzenesulfonamide

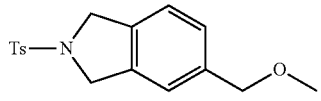 [SMILES: COCc1ccc2c(c1)CN(S(=O)(=O)c1ccc(C)cc1)C2]

To a solution of 4-methylbenzenesulfonamide (10 g, 48.1 mmol), K₂CO₃ (12.7 g, 120 mmol), in CH₃CN (200 mL) was added propargyl bromide (10.4 g, 144 mmol). The mixture was heated to 60° C. and stirred 5 h. After LCMS showed the reaction was completed, the mixture was diluted with EtOAc and water. The aqueous phase was extracted with EtOAc. The organic layer was washed with brine and dried over Na₂SO₄, filtered and concentrated under reduced pressure to get a residue, which was re-crystallized from EtOH to give the title compound (12 g, 83.1%) as yellow solid.

5-(Methoxymethyl)-2-tosylisoindoline

To a solution of 4-methyl-N,N-di(prop-2-yn-1-yl)benzenesulfonamide (5 g, 0.02 mol), 3-methoxyprop-1-yne (3.5 g, 0.05 mmol) in EtOH (100 mL) was added Rh(PPh₃)₄Cl (2.37 g, 2 mmol) at 0° C. Then the mixture was stirred at 20° C. for 18 h. After LCMS showed the reaction was completed and then the reaction was concentrated under reduced pressure to get a residue, which was purified by column chromatography on the silica gel to afford the title compound (2 g, 31.2%). ¹H NMR: (400 MHz, CD₃OD) δ 2.34-2.44 (3H, m), 3.31 (3H, s), 4.39 (2H, s), 4.56 (4H, s), 7.10-7.24 (3H, m), 7.38 (2H, d, J=7.94 Hz), 7.76 (2H, d, J=7.94 Hz).

5-(Methoxymethyl)isoindoline

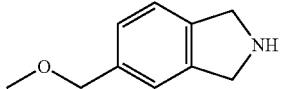

To a solution of 5-(methoxymethyl)-2-tosylisoindoline (2.5 g, 7.89 mmol), Mg (480 mg, 20 mmol) in MeOH (50 mL) was added Et3N (2.0 g, 20 mmol) and stirred at 75° C. for 24 h. The conversion is ~50%, then the reaction was concentrated under reduced pressure to get a residue, which was used directly without further purification.

N-(2-(5-(Methoxymethyl)isoindolin-2-yl)pyrimidin-4-yl)-1H-indazol-5-amine

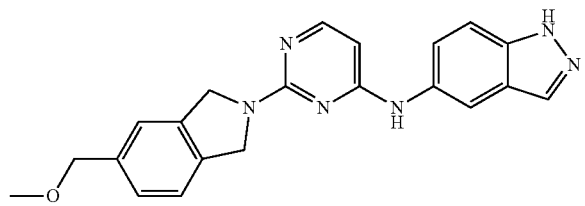 [SMILES: COCc1ccc2c(c1)CN(c1nccc(Nc3ccc4[nH]ncc4c3)n1)C2]

To a solution of 5-(methoxymethyl)isoindoline (1.5 g crude), N-(2-chloropyrimidin-4-yl)-1H-indazol-5-amine (2.5 g, 0.01 mol) in MeCN (50 mL) was added DIEA (5.2 g, 0.04 mmol) and stirred at 120° C. under microwave for 6 h. Then the reaction was concentrated under reduced pressure to get a residue, which was purified by prep-HPLC to give the final compound (94 mg) as a white solid. $^1$H NMR (400 MHz, DMSO-$d_6$) δ 4.43 (2H, s), 4.80 (4H, d, J=18.52 Hz), 6.07 (1H, d, J=5.73 Hz), 7.25 (1H, d, J=7.50 Hz), 7.42 (2H, Br. s.), 7.45-7.59 (2H, m), 7.94 (1H, d, J=5.73 Hz), 8.06 (1H, Br. s.), 8.29 (1H, Br. s.), 9.22 (1H, Br. s.), 12.91 (1H, Br. s.). MS (ES+) m/e 373 (M+H)$^+$.

Example 28

N-(2-(4-Methoxyisoindolin-2-yl)pyrimidin-4-yl)-1H-indazol-5-amine

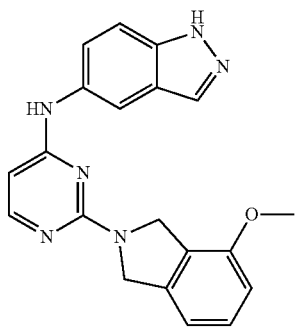 [SMILES: COc1cccc2c1CN(c1nccc(Nc3ccc4[nH]ncc4c3)n1)C2]

tert-Butyl 4-(4,4,5,5-tetramethyl-1,3,2-dioxaborolan-2-yl)isoindoline-2-carboxylate

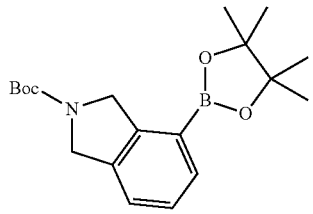 [SMILES: CC(C)(C)OC(=O)N1Cc2cccc(B3OC(C)(C)C(C)(C)O3)c2C1]

A mixture of tert-butyl 4-bromoisoindoline-2-carboxylate (1.00 g, 3.37 mmol), 4,4,4',4',5,5,5',5'-octamethyl-2,2'-bi(1,3,2-dioxaborolane) (1.03 g, 4.04 mmol), AcOK (661 mg, 6.74 mmol) and Pd(dppf)Cl$_2$ (50.0 mg) in dioxane (20 mL) was stirred at 90° C. for 16 h under the nitrogen atmosphere. After cooling down to 20° C. and LCMS showed the reaction was complete, the mixture was filtered and the filtrate was concentrated under reduced pressure to get the title compound (1.2 g, yield 103%) as a brown solid, which was directly to the next step without further purification. $^1$H NMR (CDCl$_3$, 400 MHz) δ 7.69 (d, J=7.2 Hz, 1H) 7.36-7.27 (m, 2H) 4.87-4.63 (m, 4H) 1.52 (s, 9H) 1.31 (s, 12H).

tert-Butyl 4-hydroxyisoindoline-2-carboxylate

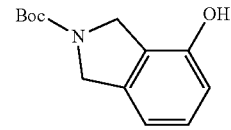

To a mixture of tert-butyl 4-(4,4,5,5-tetramethyl-1,3,2-dioxaborolan-2-yl)isoindoline-2-carboxylate (1.2 g, 3.48 mmol) in THF (20 mL) was added NH$_4$Cl (188 mg, 3.48 mmol) in H$_2$O (10 mL) and H$_2$O$_2$ (20 mL) dropwise, which was stirred at 19° C. for 16 h. After LCMS showed the reaction was complete, the reaction was quenched by aq. Na$_2$SO$_3$ solution and extracted with EtOAc (3×30 mL). The organic layer was dried over Na$_2$SO$_4$, filtered and concentrated under reduced pressure to afford the title compound (800 mg, 97.9%), which was used directly to the next step without further purification. $^1$H NMR (CDCl$_3$, 400 MHz) δ 7.19-7.11 (m, 1H) 6.83-6.68 (m, 2H) 4.78-4.63 (m, 4H) 1.24 (s, 9H).

tert-Butyl 4-methoxyisoindoline-2-carboxylate

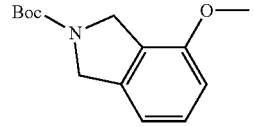 [SMILES: COc1cccc2c1CN(C(=O)OC(C)(C)C)C2]

To a mixture of tert-butyl 4-hydroxyisoindoline-2-carboxylate (750 mg, 3.19 mmol) and K$_2$CO$_3$ (880 mg, 6.38 mmol) in DMF (10 mL) was added MeI (680 mg, 4.79 mmol) dropwise, which was stirred at 100° C. for 6 hrs. After LCMS showed the reaction was complete, the mixture was concentrated, then it was dissolved in EtOAc (20 mL) and filtered, the filtrate was concentrated to give the crude title compound (700 mg, 88.0%) as a brown solid, which was used directly to the next step without further purification. $^1$H NMR (CDCl$_3$, 400 MHz) δ 7.18-7.14 (m, 1H) 6.81-6.64 (m, 2H) 4.62-4.52 (m, 4H) 3.78 (s, 3H) 1.44 (s, 9H).

4-Methoxyisoindoline

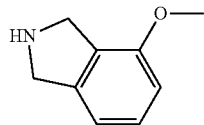

A mixture of tert-butyl 4-methoxyisoindoline-2-carboxylate (700 mg, 2.81 mmol) in HCl/EtOAc (20 mL, 4 M) was stirred at 18° C. for 16 h. After TLC (EtOAc) showed the reaction was complete, the mixture was concentrated, then it was dissolved in EtOAc (20 mL) and filtered, the filter cake was washed with EtOAc (3×10 mL) and concentrated to give the title compound (500 mg, 96.1%) as a brown solid. $^1$H NMR (DMSO-d$_6$, 400 MHz) δ 9.95 (br.s, 2H) 7.35-7.31 (m, 1H) 6.95 (d, J=7.6 Hz, 2H) 4.46-4.45 (m, 2H) 4.37 (t, J=4.8 Hz, 2H) 3.81 (s, 3H).

N-(2-(4-Methoxyisoindolin-2-yl)pyrimidin-4-yl)-1H-indazol-5-amine

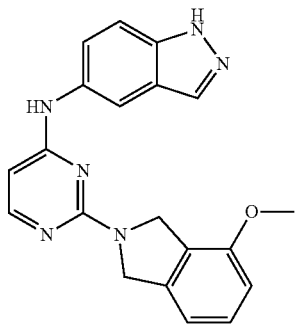 [SMILES: COc1cccc2c1CN(c1nccc(Nc3ccc4[nH]ncc4c3)n1)C2]

A mixture of 4-methoxyisoindoline (200 mg, 1.08 mmol), N-(2-chloropyrimidin-4-yl)-1H-indazol-5-amine (291 mg, 1.19 mmol) and DIPEA (559 mg, 4.32 mmol) in n-BuOH (10 mL) was stirred at 150° C. under microwave for 2 h. After LCMS showed the reaction was complete, the mixture was concentrated and purified on silica gel (PE:EtOAc=10:1~5:1~1:1~0:1) to give the crude product, which was purified by basic prep-HPLC to give the title compound (40 mg, 10.3%) as a yellow solid. $^1$H NMR (DMSO-d$_6$, 400 MHz) δ 12.93 (Br.s, 1H) 9.21 (s, 1H) 8.25 (Br.s, 1H) 7.93 (d, J=5.6 Hz, 2H) 7.49-7.47 (m, 2H) 7.31-7.27 (m, 1H) 7.03-6.97 (m, 1H) 6.90 (d, J=8.4 Hz, 1H) 6.06 (d, J=5.6 Hz, 1H) 4.84-4.68 (m, 4H) 3.84 (Br.s, 3H). MS (ES+) m/e 359.2 (M+H)$^+$.

Example 29

N-(2-(4-Fluoroisoindolin-2-yl)pyrimidin-4-yl)-1H-indazol-5-amine

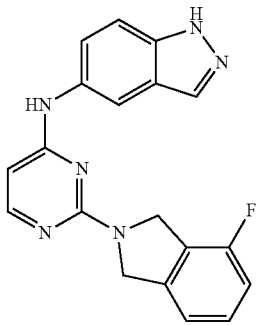 [SMILES: Fc1cccc2c1CN(c1nccc(Nc3ccc4[nH]ncc4c3)n1)C2]

1,2-bis(Bromomethyl)-3-fluorobenzene

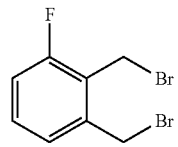 [SMILES: Fc1cccc(CBr)c1CBr]

A mixture of 1-fluoro-2,3-dimethylbenzene (1.00 g, 3.37 mmol), NBS (2.87 g, 16.1 mmol) and BPO (19.5 mg) in CCl$_4$ (50 mL) was stirred at 80° C. for 1 h. After cooling down to r.t., and TLC (PE) showed the reaction was complete, the mixture was filtered, the filtrate was concentrated under reduced pressure to get the crude product, which was purified by column chromatography on silica gel (PE) to give the title compound (1.7 g, 74.9%) as a colorless oil. $^1$H NMR (CDCl$_3$, 400 MHz) δ 7.32-7.26 (m, 1H) 7.17 (d, J=7.6 Hz, 1H) 7.08-7.01 (m, 1H) 4.70 (s, 2H) 4.63 (s, 2H).

2-Benzyl-4-fluoroisoindoline

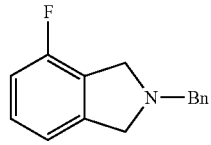 [SMILES: Fc1cccc2c1CN(Cc1ccccc1)C2]

A mixture of 1,2-bis(bromomethyl)-3-fluorobenzene (1.9 g, 6.74 mmol), BnNH$_2$ (1.08 g, 10.1 mmol) and K$_2$CO$_3$ (1.86 g, 13.9 mmol) in toluene (30 mL) was stirred at 100° C. for 12 h. After TLC (PE:EtOAc=10:1) showed the reaction was complete, the mixture was filtered, the filtrate was concentrated and purified by column chromatography on silica gel (PE:EtOAc=1:0~100:1~50:1~30:1~20:1) and prep-TLC (PE:EtOAc=10:1, R$_f$=0.6) to give the title compound (580 mg, 37.9%) as a brown oil. $^1$H NMR (CDCl$_3$, 400 MHz) δ 7.42-7.33 (m, 4H) 7.30-7.27 (m, 1H) 7.20-7.11 (m, 1H) 6.95 (d, J=7.6 Hz, 1H) 6.86 (t, J=8.8 Hz, 1H) 3.99 (s, 2H) 3.95 (s, 2H) 3.91 (s, 2H).

4-Fluoroisoindoline

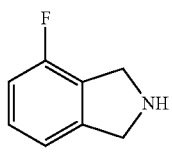

To a mixture of 2-benzyl-4-fluoroisoindoline (580 mg, 2.56 mmol) and Pd—C (200 mg) in MeOH (10 mL) was added HCl (1 mL), then the reaction mixture was stirred at 50° C. under 50 psi of $H_2$ for 16 hrs. After LCMS showed the reaction was complete, the mixture was filtered, the filtrate was concentrated to give the title compound (350 mg, 79.7%) as a light brown solid, which was used directly to the next step without further purification. $^1$H NMR (CDCl$_3$, 400 MHz) δ 7.43-7.37 (m, 1H) 7.22 (d, J=7.6 Hz, 1H) 7.09 (t, J=8.8 Hz, 1H) 4.57 (br.s, 4H).

N-(2-(4-Fluoroisoindolin-2-yl)pyrimidin-4-yl)-1H-indazol-5-amine

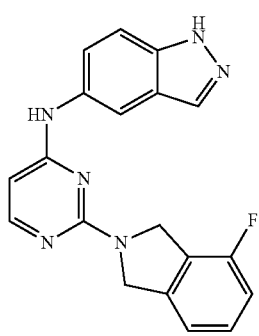

A mixture of 4-fluoroisoindoline (350 mg, 2.02 mmol), N-(2-chloropyrimidin-4-yl)-1H-indazol-5-amine (495 mg, 2.02 mmol) and DIPEA (521 mg, 4.04 mmol) in n-BuOH (5 mL) was stirred at 150° C. for 2 hrs under microwave. After LCMS showed the reaction was complete, the mixture was concentrated, then to it was added MeOH (20 mL), the precipitate was collected by filtration, washed with MeOH (3×10 mL) and dried in vacuo to give the title compound (450 mg, 64.3%) as a light brown solid. $^1$H NMR (DMSO-d$_6$, 400 MHz) δ 12.93 (s, 1H) 9.25 (s, 1H) 8.22 (br.s, 1H) 7.96-7.94 (m, 2H) 7.54-7.47 (m, 2H) 7.38-7.29 (m, 2H) 7.15-7.10 (m, 1H) 6.09 (d, J=5.6 Hz, 1H) 4.85 (br.s, 4H). MS (ES+) m/e 347.2 (M+H)$^+$.

Example 30

2-(5-Fluoroisoindolin-2-yl)-N-(1H-indazol-5-yl)-5,7-dihydrofuro[3,4-d]pyrimidin-4-amine

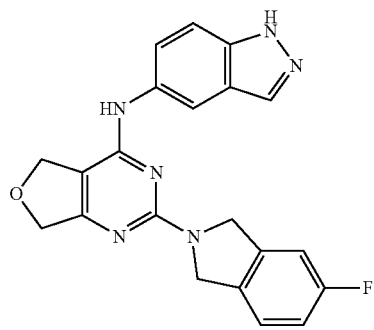 [SMILES: Fc1ccc2c(c1)CN(c1nc3c(c(Nc4ccc5[nH]ncc5c4)n1)COC3)C2]

A mixture of 2-chloro-N-(1H-indazol-5-yl)-5,7-dihydrofuro[3,4-d]pyrimidin-4-amine (0.5 g, 1.3 mmol), TEA (0.4 g, 3.9 mmol) and 5-fluoroisoindoline hydrochloride (0.29 g, 1.3 mmol) in NMP (10 mL) was heated at 150° C. for 1 h. The reaction mixture was cooled to room temperature, filtrated and purified by HPLC to give the title compound (54 mg, 8.05%). $^1$H NMR (400 MHz, METHANOL-d$_4$) δ 8.18 (1H, s) 8.04 (1H, s), 7.65 (1H, d, J=8.10 Hz), 7.52 (1H, d, J=8.40 Hz), 7.34 (1H, m), 7.10 (1H, d, J=7.60 Hz), 7.02 (1H, m), 4.79-4.91 (8H, m). MS (ES+) m/e 389 (M+H)$^+$.

Example 31

2-(5-Chloroisoindolin-2-yl)-N-(1H-indazol-5-yl)-5,7-dihydrofuro[3,4-d]pyrimidin-4-amine

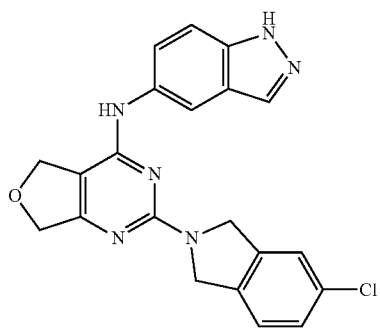 [SMILES: Clc1ccc2c(c1)CN(c1nc3c(c(Nc4ccc5[nH]ncc5c4)n1)COC3)C2]

A mixture of 2-chloro-N-(1H-indazol-5-yl)-5,7-dihydrofuro[3,4-d]pyrimidin-4-amine (1.0 g, 2.6 mmol), TEA (0.8 g, 7.8 mmol) and 5-chloroisoindoline hydrochloride (0.58 g, 2.6 mmol) in NMP (20 mL) was heated at 150° C. for 1 h. The reaction mixture was cooled to room temperature, filtrated and purified by HPLC to give the title compound (110 mg, 9.12%). $^1$H NMR (400 MHz, DMSO-d$_6$) δ 12.95 (1H, s), 8.83 (1H, s), 8.26 (1H, s), 8.08 (1H, s), 7.62 (1H, d, J=8.80 Hz), 7.49 (1H, d, J=8.80 Hz), 7.34 (1H, d, J=7.60 Hz), 4.86-4.71 (8H, m). MS (ES+) m/e 405 (M+H)$^+$.

Example 32

N-(2-(Isoindolin-2-yl)-5,6-dimethoxypyrimidin-4-yl)-1H-indazol-5-amine

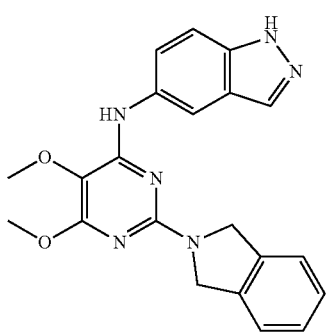 [SMILES: COc1nc(N2Cc3ccccc3C2)nc(Nc2ccc3[nH]ncc3c2)c1OC]

5-Methoxy-2-thioxodihydropyrimidine-4,6(1H,5H)-dione

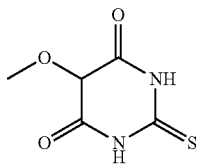

To MeOH (30 mL) was added Na (2.4 g, 104.3 mmol) at r.t. After Na disappeared, the mixture of dimethyl 2-methoxymalonate (6.8 g, 41.9 mmol) and thiourea (4.8 g, 61.3 mmol) was added. The resulting mixture was stirred for 10 h at 80° C. After TLC showed the reaction was complete, the solvent was evaporated. Water was added and washed with EtOAc (3×30 mL). The aqueous layer was acidified to pH=1 with HCl, The precipitate was collected by filtration and dried in vacuo to give the title compound (5 g, 64.1%). $^1$H NMR (400 MHz, DMSO) δ 10.41 (s, 2H) 3.75 (s, 3H).

5-Methoxy-2-(methylthio)pyrimidine-4,6(1H,5H)-dione

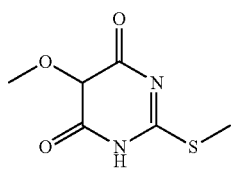

MeI (4.45 g, 31.3 mmol) was added dropwise to the mixture of 5-methoxy-2-(methylthio)pyrimidine-4,6(1H,5H)-dione (5 g, 28.6 mmol) and NaOH (1.36 g, 34 mmol) in water (40 mL). After addition, the resulting mixture was stirred for 16 hrs. The mixture was filtered and the filtrate was acidified to pH=1 and the precipitate was collected by filtration, washed with water and dried in vacuo to give the title compound (2 g, 37%). $^1$H NMR (400 MHz, MeOD) δ 3.71 (s, 3H) 2.52 (s, 3H)

4,6-Dichloro-5-methoxy-2-(methylthio)pyrimidine

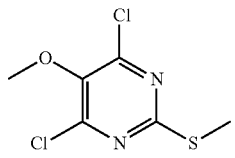

A mixture of 5-methoxy-2-(methylthio)pyrimidine-4,6(1H,5H)-dione (2 g, 10.6 mmol) and N,N-diethylaniline (1 mL) in phosphorus oxychloride (15 mL) was heated at 100° C. for 3 h. The reaction was complete detected by LCMS. The excess reagent was removed by vacuum and the residue poured onto ice and extracted with MTBE. The organic phase was washed with water (2×10 mL), dried over Na$_2$SO$_4$ and concentrated by vacuum to give crude product. The crude product was purified by column chromatography on silica gel (PE:EtOAc=10:1) to give the title compound (2.3 g, 96%) as a white solid. $^1$H NMR (400 MHz, MeOD) δ 3.90 (s, 3H) 2.53 (s, 3H).

N-(6-Chloro-5-methoxy-2-(methylthio)pyrimidin-4-yl)-1H-indazol-5-amine

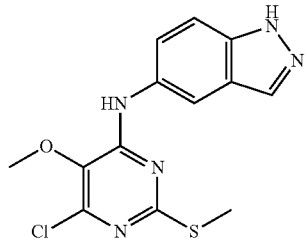 [SMILES: COc1c(Cl)nc(SC)nc1Nc1ccc2[nH]ncc2c1]

A mixture of 4,6-dichloro-5-methoxy-2-(methylthio)pyrimidine (2.0 g, 89 mmol) and 1H-indazol-5-amine (1.54 g, 11.6 mmol) in ethanol (15 mL) was heated under reflux for 16 h, then the solvent was removed under reduced pressure. The crude product was purified by column chromatography on silica gel (PE:EtOAc=1:1) to give the title compound (2.3 g, 82%) as a white solid. $^1$HNMR (400 MHz, DMSO) δ 9.44 (s, 1H) 8.02 (d, J=8.0 Hz, 1H) 7.58 (d, J=7.6 Hz, 1H) 7.50 (d, J=8.8 Hz, 1H) 3.80 (s, 1H) 2.38 (s, 1H).

N-(5,6-Dimethoxy-2-(methylthio)pyrimidin-4-yl)-1H-indazol-5-amine

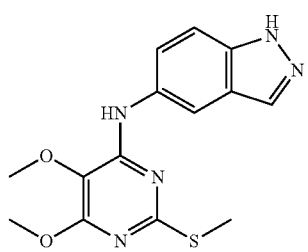 [SMILES: COc1nc(SC)nc(Nc2ccc3[nH]ncc3c2)c1OC]

To MeOH (30 mL) was added Na (0.36 g, 15.5 mmol) at room temperature. After Na disappeared, N-(6-chloro-5-methoxy-2-(methylthio)pyrimidin-4-yl)-1H-indazol-5-amine (1.0 g, 3.1 mmol) was added. The resulting mixture was stirred for 10 h at 80° C. After TLC showed the reaction was complete, the solvent was concentrated under reduced pressure, the residue was dissolved in CH$_2$Cl$_2$, washed with water (2×10 mL), dried over Na$_2$SO$_4$ and evaporated by vacuum to give the title compound (0.9 g, 92%).

N-(5,6-Dimethoxy-2-(methylsulfonyl)pyrimidin-4-yl)-1H-indazol-5-amine

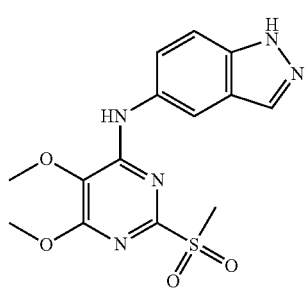 [SMILES: COc1nc(S(C)(=O)=O)nc(Nc2ccc3[nH]ncc3c2)c1OC]

A mixture of N-(5,6-dimethoxy-2-(methylthio)pyrimidin-4-yl)-1H-indazol-5-amine (0.9 g, 3.1 mmol) and 3-chloroperoxybenzoic acid (2.03 g, 9.3 mmol) in dichloromethane (30 mL) was stirred at 25° C. for 3 h. TLC showed the reaction was complete, the mixture was washed with aq. Na$_2$SO$_3$ (2×20 mL), aq. NaHCO$_3$ (2×20 mL), H$_2$O (20 mL), dried over Na$_2$SO$_4$ and evaporated by vacuum to give the tile compound (0.9 g, 90%) as a white solid.

N-(2-(Isoindolin-2-yl)-5,6-dimethoxypyrimidin-4-yl)-1H-indazol-5-amine

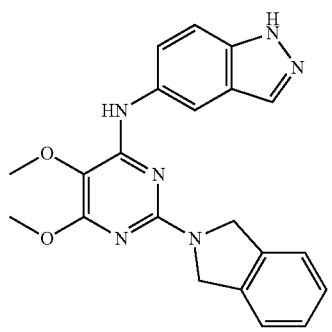 [SMILES: COc1nc(N2Cc3ccccc3C2)nc(Nc2ccc3[nH]ncc3c2)c1OC]

A mixture of N-(5,6-dimethoxy-2-(methylsulfonyl)pyrimidin-4-yl)-1H-indazol-5-amine (0.9 g, 2.5 mmol) and isoindoline (0.58 g, 3.75 mmol) in 1,4-dioxane (30 mL) was reacted under microwave at 140° C. for 5 h. LCMS showed most of the starting material was consumed, and then the solvent was removed under reduced pressure. The crude product was purified by neutral prep-HPLC to give the title compound (175 mg, 18%) as a brown solid. $^1$H NMR (MeOD, 400 MHz) δ 12.88 (s, 1H) 8.50 (s, 1H) 8.28 (s, 1H) 8.02 (s, 1H) 7.74 (d, J=8.8 Hz, 1H) 7.46-7.41 (m, 3H) 7.29-7.27 (m, 2H), 4.77 (s, 4H) 3.91 (s, 3H) 3.64 (s, 3H). MS (ES+) m/e 389 (M+H)$^+$.

Example 33

ROCK2 siRNA, but not ROCK1 siRNA Inhibits, IL-17 and IL-21 Secretion

Figure 2:
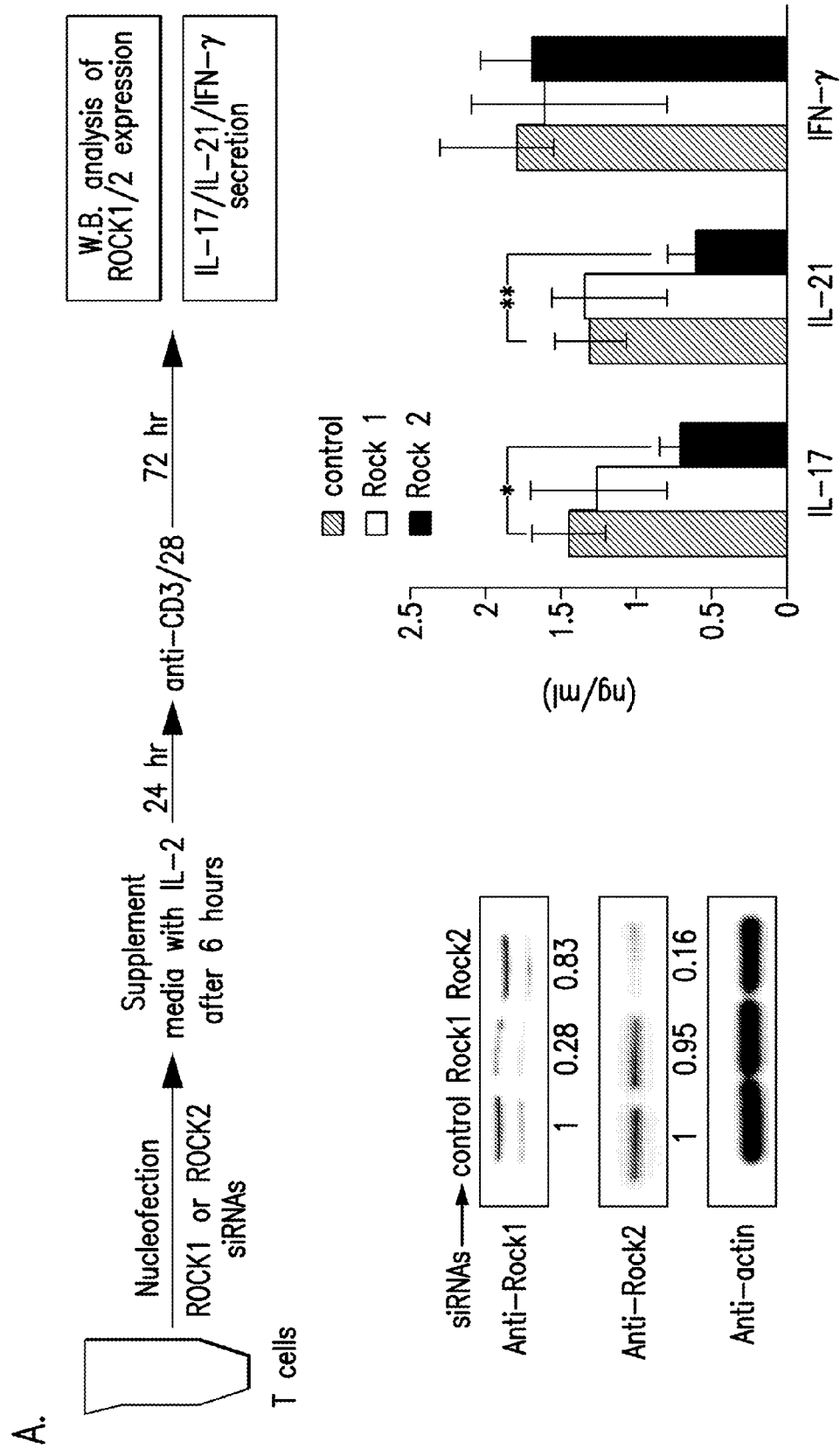
FIG. 2 shows ROCK2 siRNA, but not ROCK1 siRNA, inhibits IL-17 and IL-21 secretion. Panel A, left: Anti-ROCK1 siRNA reduced Rock1 expression by about 75%. Anti-ROCK2 siRNA reduced Rock2 expression by about 85%. Panel A, right: ROCK2 siRNA, but not ROCK1 siRNA, inhibited IL-17 and IL-21 expression. No inhibition of IFN-γ was observed. Panel B: ROCK2 siRNA, but not ROCK1 siRNA, inhibited phosphorylation of Stat3, IRF4, and RORγt. Panel C: ROCK2 siRNA, but not ROCK1 siRNA, inhibited phosphorylation of MLC.
Figure 3:
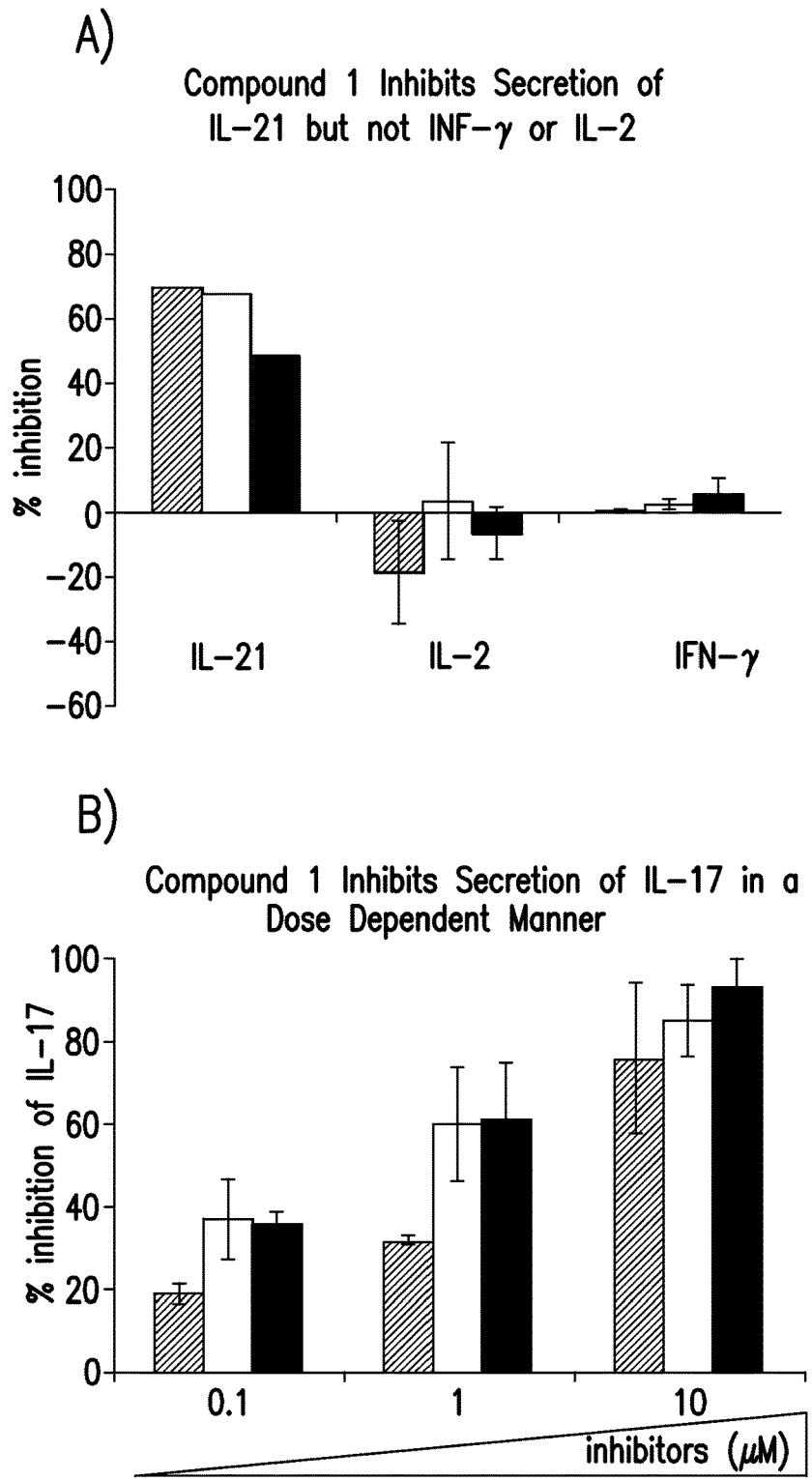
FIG. 3 shows compounds of the invention regulate cytokine secretion. Panel A shows the compound of Example 1 inhibits secretion of IL-21, but not INF-γ or IL-2. Panel B shows inhibition of IL-17 secretion is dose-dependent. Legend (A and B): left bars 1: KD025 (a ROCK2 selective inhibitor); center bar: compound of Example 1 dissolved in HCL; right bar; compound of Example 1 dissolved in DMSO.

To confirm the role of ROCK2 in regulation of IL-17 and IL-21 secretion in human T cells we specifically silenced ROCK1 and ROCK2 expression by RNA interference. Specific ROCK1 and ROCK2 small interfering RNA (siRNA) reduced the protein expression levels by 72% and 84% respectively. Silencing of ROCK2, but not of ROCK1 significantly reduced the IL-17 and IL-21, with minimal effect on IFN-γ secretion in human T cells (FIG. 2).

Example 34

ROCK1 and ROCK2 Compound Selectivity

Dose response curves for Rho-kinase inhibition were derived from a Invitrogen Z'-LYTE™ Kinase Assay Kit (Invitrogen catalog number PV3793). Purified active ROCK1 and ROCK2 were obtained from Invitrogen (catalog numbers ROCK1, PV3691 and ROCK2, PV3759). The kit components include a coumarin and fluorescein labeled peptide based on myosin light chain 2 (KKRPQRRYSNVF), a proprietary protease containing development reagent and a proprietary Stop buffer used to terminate the development reaction. The inhibitory activities of compounds are measured according to the manufactures protocol. Briefly, decreasing concentrations of test compounds or the known ROCK inhibitor Y-27963, are added, from 10 uM to 2.56× 10$^{-5}$ uM to reaction buffer containing 50 mM HEPES pH 7.5, 10 mM MgCl$_2$, 5 mM EGTA, and 0.05% Brij-35 and of ROCK1 at 0.18 ug/mL or ROCK2 at 0.8 ug/mL in assay dilution buffer. This mixture is overlayed into a white 96-well half area plate and the reaction is initiated with the addition of 5 uM ATP for ROCK1 or 12 uM ATP for ROCK2. The assay proceeds at room temperature for 1 hour followed by the addition of development reagent, and further incubation for 1 hour at room temperature. STOP reagent is then added and the reaction and immediately the coumarin and fluorescein emission signals are read on a Tecan Infinite M1000 fluorescence plate reader (excitation: 400 nm; emission 445 and 520 nm, respectively). By comparing the emission ratios of the test samples against control samples, percent phosphorylation values are calculated and the concentration of inhibitor that produces ½ inhibition of kinase activity (IC$_{50}$) is determined using Prism. Table 1 provides IC$_{50}$ concentrations for compounds of the above examples. Several of the compounds also demonstrated activity in a preliminary assay that measured inhibition of myosin light chain phosphorylation (pMLC). For compounds marked ND, activity was not determinable under the test conditions employed. Data showing inhibition of ROCK1 and ROCK2, and selectivity of certain compounds for ROCK2 inhibition, is presented in Table 1.

TABLE 1

| | ROCK Inhbition | | |
|---|---|---|---|
| Ex. # | ROCK2 IC$_{50}$ (nM) | ROCK1 IC$_{50}$ (nM) | pMLC inhibition |
| 1 | 10 | 893 | + |
| 1 | 2 | 434 | |
| 2 | 60 | >10000 | + |
| 3 | 30 | 8340 | ++ |
| 4 | 190 | | |
| 4 | 140 | | |
| 5 | 50 | 8570 | + |
| 6 | 30 | 2370 | + |
| 7 | 10 | 3750 | ++ |
| 8 | 1170 | >10000 | ND |
| 9 | 40 | 2930 | ND |
| 10 | 110 | >10000 | ND |
| 11 | 700 | >10000 | + |
| 12 | 1060 | >10000 | + |
| 13 | 130 | >10000 | + |
| 14 | 130-180 | >10000 | + |
| 15 | 340 | >10000 | + |
| 16 | >10 | | + |
| 17 | | >10000 | |
| 18 | 2 | >10000 | |
| 19 | >10000 | >10000 | |
| 20 | 35 | >10000 | |
| 20 | 40 | >10000 | |
| 21 | 185 | >10000 | |
| 22 | 24330 | 3500 | + |
| 22 | 24000 | >10000 | + |
| 24 | ND | 2500 | ++ |
| 25 | 130 | >10000 | + |
| 26 | 123 | >10000 | ++ |
| 27 | 100 | 6730 | ++ |
| 28 | 100 | | ++ |
| 29 | 880 | | ++ |
| 30 | | >10000 | |
| 32 | 607 | >10000 | ++ |

Example 35

The ROCK2 Selective Inhibitor of Example 1 Inhibits IL-17 and IL-21 Secretion, But Not INF-γ or IL-2 Secretion, in Human CD4+ T Cells in vitro.

Activation of resting T cells, resulting in cytokine secretion and proliferation, involves two distinct signals from antigen-presenting cells (APCs), mimicked by co-stimulation of the T cell receptor (TCR)/CD3 complex and the CD28 receptor. Using freshly purified CD4+ human T cells and stimulatory antibodies against CD3 and CD28 to stimulate IL-17 and IL-21 secretion in response to TCR activation, it was found that the treatment with the ROCK2 selective inhibitor of Example 1, significantly inhibited IL-17 and IL-21 secretion in a dose-dependent manner. Under the same conditions, the inhibition of IFN-γ and IL-2 was not observed (FIG. 2).

Example 36

The ROCK2 Inhibitor of Example 1 Reduces Paralysis Associated with Experimental Autoimmune Encephalomyelitis (EAE).

Figure 5:
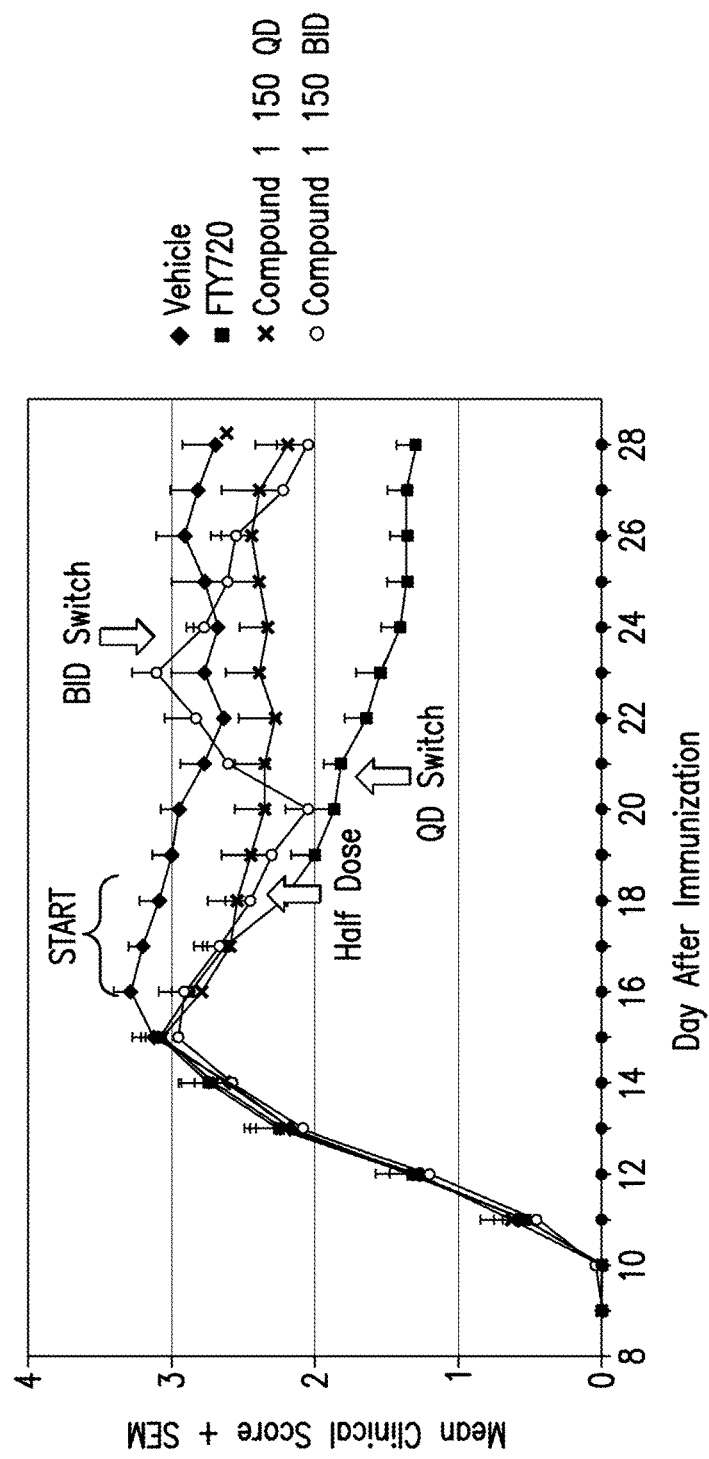
FIG. 5 shows a ROCK inhibitor (the compound of Example 1) reduces paralysis associated with experimental autoimmune encephalomyelitis (EAE). C57BL/6 mice were immunized with MOG$_{35-55}$ peptide in complete Freund's Adjuvant (CFA). Mice were then treated with the indicated compounds (FTY720 at 10 mg/kg and Compound 1 at 150 mg/kg once [QD] or twice a day [BID]) when they individually had signs of paralysis for three days. Dosage changes of Compound 1 during the course of treatment are indicated for the 150 BID group. FTY720 is a sphingosine 1-phosphate receptor modulator.

For induction of EAE, mice were immunized subcutaneously on day 0 with 150 mg/mouse MOG 35-55 peptide (Molecular Biology Core Facilities, Dana-Farber Cancer Institute, Harvard University), emulsified in CFA (CFA supplemented with 400 mg/ml Mycobacterium tuberculosis) Mice were then treated with the indicated compounds (FTY720 at 10 mg/kg and Compound 1 at 150 mg/kg once [QD] or twice a day [BID]) when they individually had signs of paralysis for three days. Dosage changes of Compound 1 treatment are indicated for the 150 BID group only. FTY720 is a sphingosine 1-phosphate receptor modulator. FTY720 induces a decrease in the number of peripheral blood lymphocytes and exerts immunomodulating activity in various experimental allograft and autoimmune disease models. EAE scoring was based on Ivanov, et al., 2006. Briefly: 0—no disease, 1—limp tat 2—weak/partially paralyzed hind legs, 3—completely paralyzed hind legs, 4—complete hind and partial front leg paralysis, 5—complete paralysis/death. Mean clinical scores of treated mice are depicted in FIG. 5. Subjects treated with compound 1 demonstrated a substantial improvement in their clinical scores.

Example 36

VEGFR2 Antibodies

Non-limiting examples of VEGFR2-binding antibody sequences are provided. As described herein, from human Fab phage display libraries, two neutralizing antibodies were identified that bind to human VEGFR2, block binding of the ligand VEGFA to hVEGFR2, and inhibit the VEGFR2 phosphorylation and downstream signal transduction stimulated by VEGFA. Table 1 indicates amino acid sequences of the CDRs and variable domains of antibodies of the antibodies. The $K_d$s of Mab 101 and Mab 102 are about 6.6 mM and 1.7 nM, respectively.

The heavy chain of Mab 101 was reshuffled with κ light chain genes (κ-library) and λ light chain genes (λ-library). 20 unique λ light chain variants were found by panning the λ-library against both human VEGFR2 and mouse VEGFR2. 22 unique κ light chain variants were found by panning the κ-library against both human VEGFR2 and mouse VEGFR2. Table 2 indicates amino acid sequences of the CDRs and variable domains of the light chains. The KDs of Mabs 105, 106, and 107 were increased about 10 fold (0.24 nM, 0.22 nM, and 0.12 nM, respectively).

Mab 138 (Table 2), containing the Mab 4 heavy chain, was selected for affinity maturation. Mutations were introduced into CDR3 of the light chan and CDR1, CDR2, and CDR3 of the heavy chain. The resulting library was panned on human and murine VEGFR2. Table 3 indicates amino acid sequences of the heavy and light chain CDRs and variable domains of four of the resulting antibodies. FIG. 6 shows a comparison of the sequences to the Mab 4 heavy chain and Mab 138 kappa chain (i.e. SEQ ID NO:160).

TABLE 3

Antibody Amino Acid Sequences by SEQ ID NO

| Mab # | CDR-H1 | CDR-H2 | CDR-H3 | $V_H$ domain | CDR-L1 | CDR-L2 | CDR-L3 | $V_L$ domain |
|---|---|---|---|---|---|---|---|---|
| 147 | 197 | 198 | 199 | 200 | 201 | 202 | 203 | 204 |
| 148 | 205 | 206 | 207 | 208 | 209 | 210 | 211 | 212 |
| 149 | 213 | 214 | 215 | 216 | 217 | 218 | 219 | 220 |
| 150 | 221 | 222 | 223 | 224 | 225 | 226 | 227 | 228 |
| 151 | 229 | 230 | 231 | 232 | 233 | 234 | 235 | 236 |

The binding constants of Mab 147 and Mab 149 as well as the parent Mab 160 for human, murine, and rat VEGFR2 were determined by Biacore analysis (Table 4).

TABLE 4

Biacore Analysis of Binding to Human, Murine, and Rat VEGFR2

| Mab | antigen | $k_a$ | $k_d$ | $K_D$ |
|---|---|---|---|---|
| 138 | rat | 4.30E+04 | 1.34E−03 | 3.12E−08 |
|  | murine | 2.86E+04 | 2.33E−03 | 8.17E−08 |
|  | human | 8.98E+04 | 6.00E−04 | 6.68E−09 |
| 147 | rat | 6.45E+04 | 8.99E−04 | 1.39E−08 |
|  | murine | 4.38E+04 | 1.28E−03 | 2.94E−08 |
|  | human | 1.13E+05 | 2.82E−04 | 2.51E−09 |
| 149 | rat | 3.32E+04 | 1.43E−03 | 4.31E−08 |
|  | murine | 2.29E+04 | 1.81E−03 | 7.92E−08 |
|  | human | 8.62E+04 | 6.59E−04 | 7.65E−09 |

Figure 7:
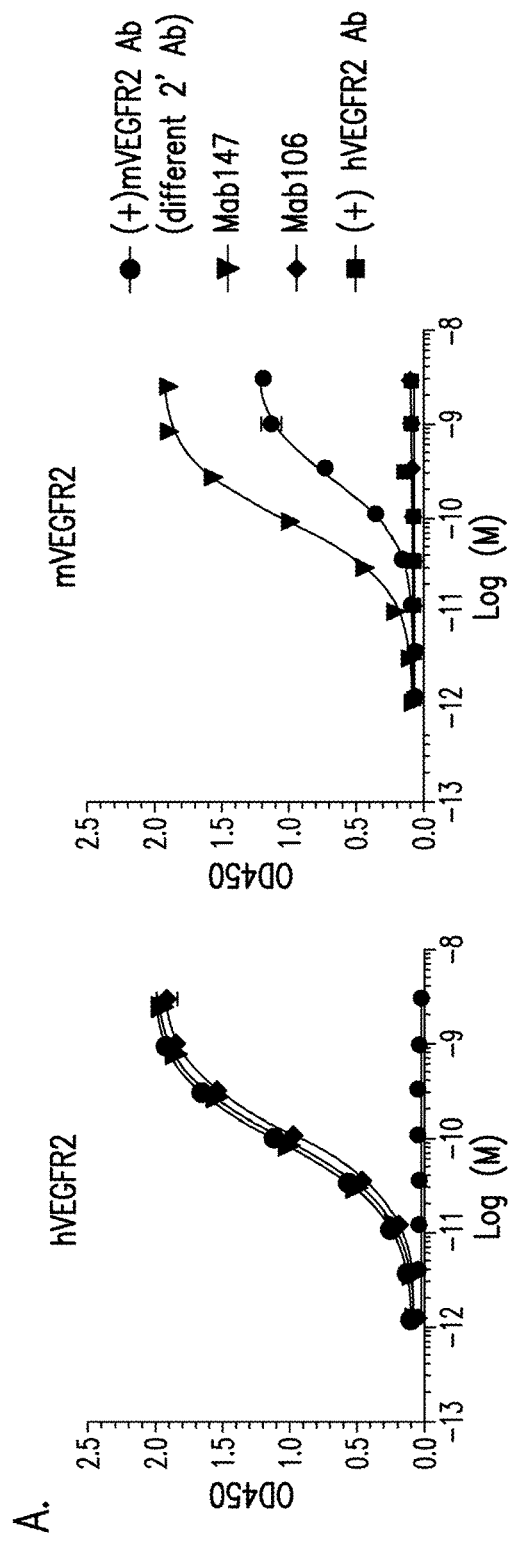
FIG. 7A depicts binding of antibodies of the invention to human and murine VEGFR2 compared to DC 101 (a murine monoclonal Ab that binds to murine VEGFR2) and a control antibody that binds only to human VEGFR2. Mab 147 binds to both human and murine VEGFR2. Mab 106 binds to human VEGFR2 but not murine VEGFR2.
FIG. 7B depicts ligand blocking Mab 147 blocks the binding of human VEGF with human VEGFR2 and the binding of murine VEGF with murine VEGFR2. Mab 106 blocks the binding of human VEGF with human VEGFR2 but not the binding of murine VEGF with murine VEGFR2.
Figure 7:
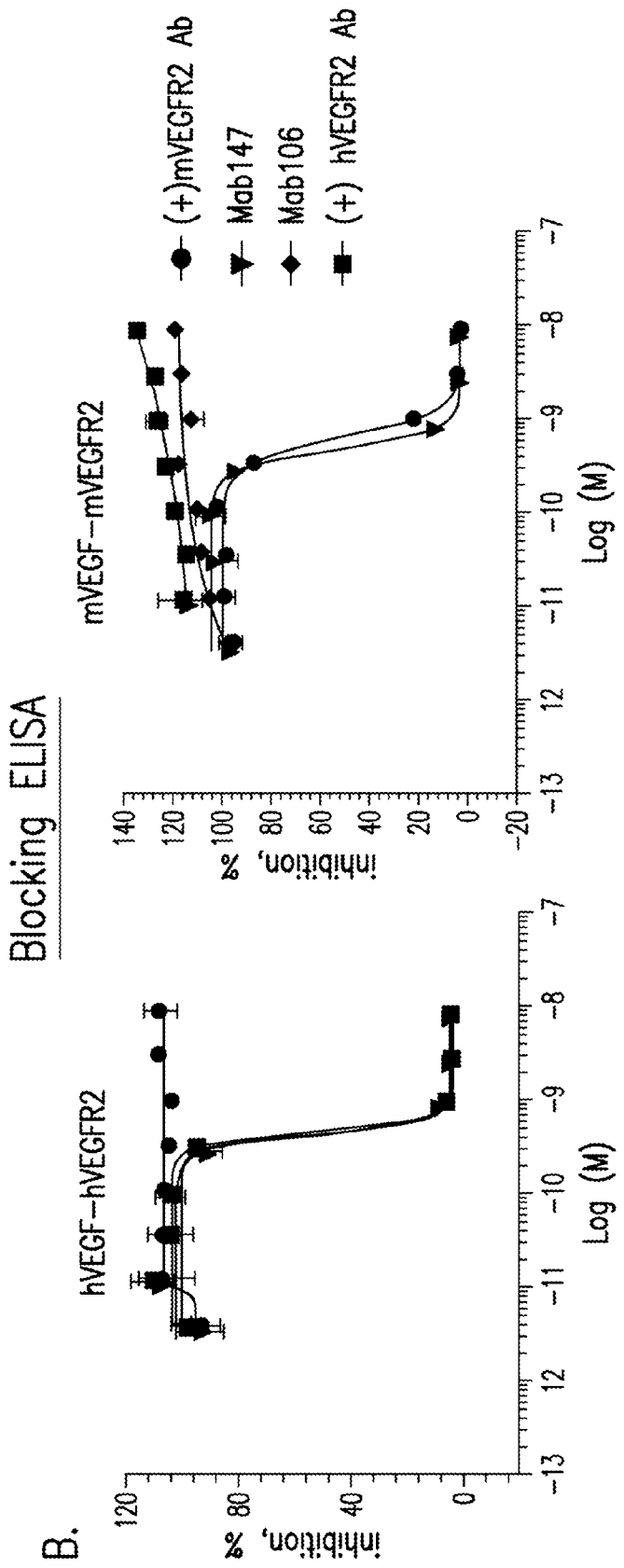

Mab 147 was examined by ELISA for its receptor binding and ligand blocking properties. Mab 147 block binds to both hVEGFR2 and mVEGFR2 with similar affinity (FIG. 7A). Mab 147 blocks ligand binding to hVEGFR2 similar to an hVEGFR specific control antibody and also blocks ligand binding to mVEGFR2 similar to an mVEGFR2-specific control antibody (FIG. 7B).

Binding of Mab 147 to hVEGFR2 and mVEGFR2 expressed on cell membranes was also confirmed. FIG. 8A shows binding to hVEGR2 expressed by human umbilical vein entothelial cells (HUVEC) as well as procine aortic endothelial (PAE) cells overexpressing KDR (i.e., human VEGFR2). Mab 147 also bound to mVEGFR expressed by MS1 murine endothelial cells (FIG. 8B).

Figure 9:
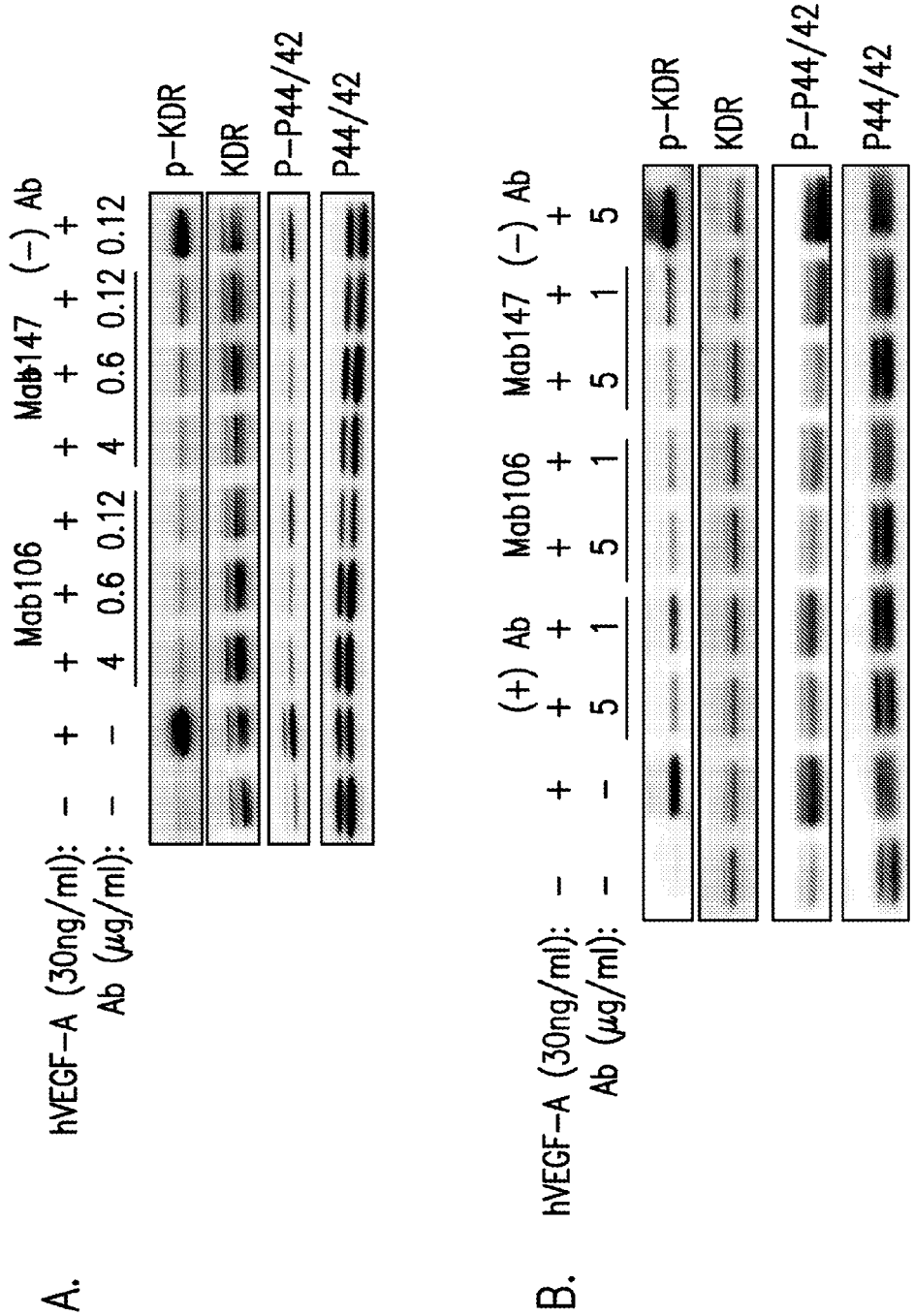
FIG. 9 shows inhibition of VEGFR2-mediated signal transduction by Mab 106 and Mab 147. Mab 106 and Mab 147 inhibit phosphorylation of KDR and p44/42 in KDR-PAE (FIG. 9A) cells and in HUVEC (FIG. 9B) in a dose dependent manner.
Figure 10B:
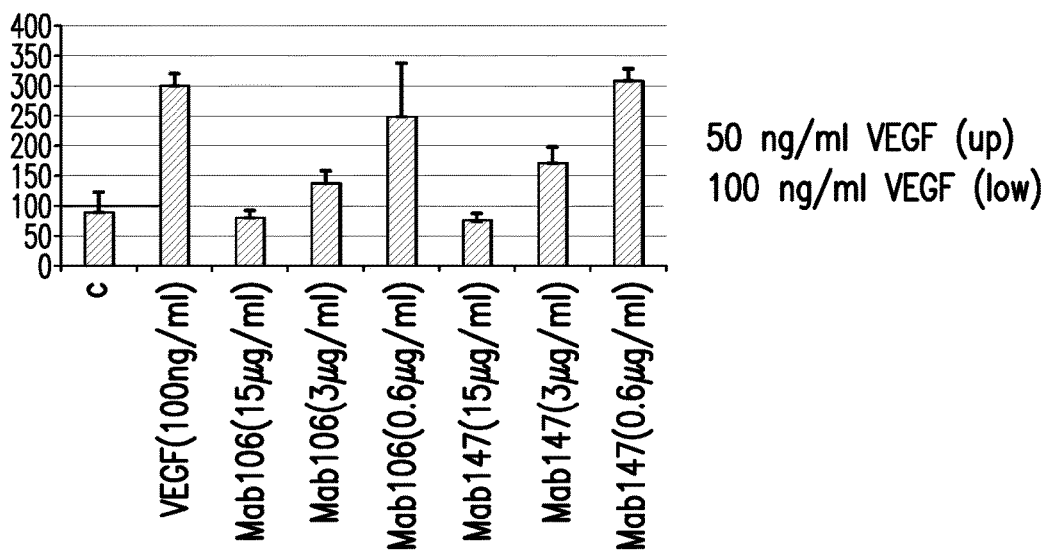
FIG. 10B shows inhibition of induced cell migration. Migration of KDR-PAE cells was induced with a VEGF gradient (50 ng/ml VEGF (up), 100 ng/ml VEGF (low)). The plot depicts cell counts in the presence of 0.6 μg/ml, 3 μg/ml, or 15 μg/ml of Mab 106 or Mab 147 antibody.

Mab-147 inhibits VEGFR-2 mediated signal transduction in KDR-PAE cells, as indicated by reduced phosphorylation of KDR and p42/44 in KDR-PAE cells (FIG. 9A) and in HUVEC (FIG. 9B). Mab-106 and Mab-147 inhibit proliferation of KDR-PAE cells (FIG. 10A), as well as inhibiting VEGF-induced migration of KDR-PAE cells (FIG. 10B).

We claim:
1. A compound having the formula II:

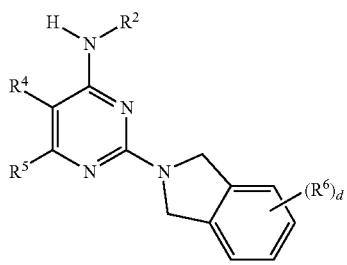

(II)

wherein
R² is selected from the group consisting of indazol-5-yl, cyclohexylpyridine, phenylpyridine, 4-(1H-pyrazol-4-yl)phenyl, 1H-pyrrolo[2,3-b]pyridine, pyridine, isoquinoline, quinoline, and 1,3-thiazolyl pyridine;
R⁴ and R⁵ are independently selected from the group consisting of H, halo, $C_1$-$C_8$ alkyl, $C_2$-$C_8$ alkenyl, $C_2$-$C_8$ alkynyl, $C_1$-$C_6$ alkoxy, —($C_1$-$C_6$ alkyl)-O—($C_1$-$C_6$ alkyl), —NR⁴¹R⁴², —(CH₂)ₓNR⁴¹R⁴² and —O—($C_1$-$C_6$ alkyl)-O—($C_1$-$C_6$ alkyl);
R⁴¹ and R⁴² are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);
or R⁴¹ and R⁴² may be taken together to form a three to twelve membered cycloalkyl or heterocyclic ring having up to 3 heteroatoms which is optionally substituted from 1 to 3 substituents independently selected from halo, $C_1$-$C_6$ alkyl, and $C_1$-$C_6$ alkoxy;
x is selected from 0 to 6;
or R⁴ and R⁵ may be taken together to form a three to twelve membered heterocyclic or aromatic ring having up to 3 heteroatoms which is optionally substituted from 1 to 3 substituents independently selected from halo and $C_1$-$C_6$ alkyl and $C_1$-$C_6$ alkoxy;
each R⁶ is independently selected from the group consisting of halo, $C_1$-$C_6$ alkyl, $C_2$-$C_6$ alkenyl, $C_1$-$C_6$ alkoxy, —($C_1$-$C_6$ alkyl)-O—($C_1$-$C_6$ alkyl), $C_3$-$C_7$ cycloalkyl, oxo, acyl, —S—($C_1$-$C_6$ alkyl), OH, NH₂, CN and $C_1$-$C_3$ perfluroalkyl; and
d is selected from 0 to 3.

2. The compound of claim 1, having the formula III:

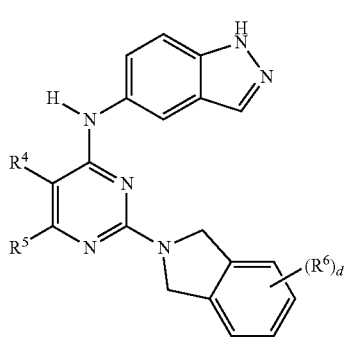

(III)

R⁴ and R⁵ are independently selected from the group consisting of H, halo, $C_1$-$C_8$ alkyl, $C_2$-$C_8$ alkenyl, $C_2$-$C_8$ alkynyl, $C_1$-$C_6$ alkoxy, —($C_1$-$C_6$ alkyl)-O—($C_1$-$C_6$ alkyl), —NR⁴¹R⁴², —(CH₂)ₓNR⁴¹R⁴² and —O—($C_1$-$C_6$ alkyl)-O—($C_1$-$C_6$ alkyl;
R⁴¹ and R⁴² are independently selected from the group consisting of H, $C_1$-$C_8$ alkyl, $C_2$-$C_8$ alkenyl, $C_2$-$C_8$ alkynyl, and —($C_1$-$C_6$ alkyl)-O—($C_1$-$C_6$ alkyl);
or R⁴¹ and R⁴² may be taken together to form a three to twelve membered cycloalkyl or heterocyclic ring having up to 3 heteroatoms which is optionally substituted from 1 to 3 substituents independently selected from halo, $C_1$-$C_6$ alkyl, and $C_1$-$C_6$ alkoxy;
x is selected from 0 to 6;
or R⁴ and R⁵ may be taken together to form a three to twelve membered heterocyclic or aromatic ring having up to 3 heteroatoms which is optionally substituted from 1 to 3 substituents independently selected from halo and $C_1$-$C_6$ alkyl and $C_1$-$C_6$ alkoxy;
each R⁶ is independently selected from the group consisting of halo, $C_1$-$C_6$ alkyl, $C_2$-$C_6$ alkenyl, $C_1$-$C_6$ alkoxy, —(C$_1$-C$_6$ alkyl)-O—(C$_1$-C$_6$ alkyl), C$_3$-C$_7$ cycloalkyl, oxo, acyl, —S—(C$_1$-C$_6$ alkyl), OH, NH$_2$, CN and C$_1$-C$_3$ perfluroalkyl; and d is selected from 0 to 3.

3. The compound of claim 1, wherein R$^2$ is selected from:

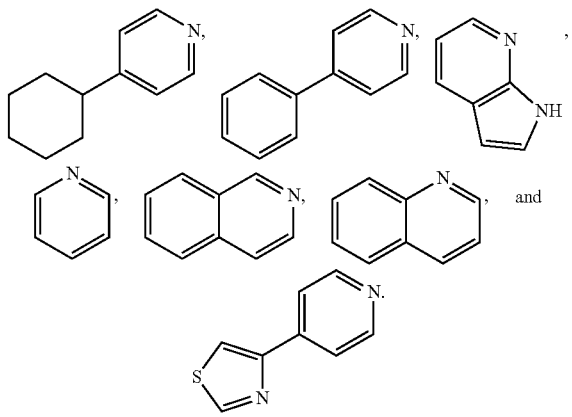

4. The compound of claim 1, wherein R$^4$ and R$^5$ are taken together to form a five-membered ring.

5. The compound of claim 1, having the chemical name:
N-(2-(5-Methoxyisoindolin-2-yl)pyrimidin-4-yl)-1H-indazol-5-amine,
N-(2-(Isoindolin-2-yl)pyrimidin-4-yl)-1H-indazol-5-amine,
N-(5-Fluoro-2-(5-methoxyisoindolin-2-yl)pyrimidin-4-yl)-1H-indazol-5-amine,
N-(5-Chloro-2-(5-methoxyisoindolin-2-yl)pyrimidin-4-yl)-1H-indazol-5-amine,
N-(2-(5-Methoxyisoindolin-2-yl)-5-methylpyrimidin-4-yl)-1H-indazol-5-amine,
N-(2-(5-Methoxyisoindolin-2-yl)-6-methylpyrimidin-4-yl)-1H-indazol-5-amine,
N-(2-(5-Fluoroisoindolin-2-yl)pyrimidin-4-yl)-1H-indazol-5-amine,
N-(2-(5-Chloroisoindolin-2-yl)pyrimidin-4-yl)-1H-indazol-5-amine,
N-(2-(5-(Methoxymethyl)isoindolin-2-yl)pyrimidin-4-yl)-1H-indazol-5-amine, or
N-(2-(4-Methoxyisoindolin-2-yl)pyrimidin-4-yl)-1H-indazol-5-amine.

6. The compound of claim 1, having the chemical name:
N-(2-(5-Methoxyisoindolin-2-yl)pyrimidin-4-yl)-1H-indazol-5-amine.

7. The compound of claim 1, having the chemical name:
N-(4-(1H-pyrazol-4-yl)phenyl)-2-(5-methoxyisoindolin-2-yl)pyrimidin-4-amine, or
2-(5-Methoxyisoindolin-2-yl)-N-(4-(pyridin-4-yl)phenyl)pyrimidin-4-amine.

8. The compound of claim 1, having the chemical name:
N-(6-(5-Methoxyisoindolin-2-yl)pyrimidin-4-yl)-1H-indazol-5-amine, or
N-(6-(5-Methoxyisoindolin-2-yl)-2-methylpyrimidin-4-yl)-1H-indazol-5-amine.

* * * * *